US012729169B2

(12) United States Patent
Li et al.

(10) Patent No.: US 12,729,169 B2
(45) Date of Patent: Sep. 8, 2026

(54) DIRECT AROMATIC CARBON-OXYGEN AND CARBON-HYDROGEN BOND FUNCTIONALIZATION VIA ORGANIC PHOTOREDOX CATALYST

(71) Applicant: THE UNIVERSITY OF NORTH CAROLINA AT CHAPEL HILL, Chapel Hill, NC (US)

(72) Inventors: Zibo Li, Chapel Hill, NC (US); David Nicewicz, Durham, NC (US); Wei Chen, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 1067 days.

(21) Appl. No.: 17/434,677

(22) PCT Filed: Feb. 27, 2020

(86) PCT No.: PCT/US2020/020232

§ 371 (c)(1),
(2) Date: Aug. 27, 2021

(87) PCT Pub. No.: WO2020/176804

PCT Pub. Date: Sep. 3, 2020

(65) Prior Publication Data

US 2022/0169581 A1 Jun. 2, 2022

Related U.S. Application Data

(60) Provisional application No. 62/812,179, filed on Feb. 28, 2019.

(51) Int. Cl.

| | |
|---|---|
| *C07C 17/12* | (2006.01) |
| *B01J 31/00* | (2006.01) |
| *B01J 35/39* | (2024.01) |
| *C07B 59/00* | (2006.01) |
| *C07C 17/361* | (2006.01) |
| *C07C 41/22* | (2006.01) |
| *C07C 45/63* | (2006.01) |
| *C07C 67/287* | (2006.01) |
| *C07C 67/307* | (2006.01) |
| *C07C 231/12* | (2006.01) |
| *C07C 253/30* | (2006.01) |
| *C07C 269/06* | (2006.01) |

(Continued)

(52) U.S. Cl.

CPC .......... *C07B 59/001* (2013.01); *B01J 31/006* (2013.01); *B01J 35/39* (2024.01); *C07C 17/12* (2013.01); *C07C 41/22* (2013.01); *C07C 45/63* (2013.01); *C07C 67/307* (2013.01); *C07C 231/12* (2013.01); *C07C 253/30* (2013.01); *C07C 269/06* (2013.01); *C07D 213/69* (2013.01); *C07D 215/20* (2013.01); *C07D 231/56* (2013.01); *C07D 235/24* (2013.01); *C07D 239/96* (2013.01); *C07D 263/58* (2013.01); *C07D 311/22* (2013.01); *B01J 2231/46* (2013.01); *C07B 2200/05* (2013.01)

(58) Field of Classification Search

CPC ......... C07C 17/12; C07C 41/22; C07C 45/63; C07C 67/307; C07C 231/12; C07C 253/30; C07C 269/06; C07C 17/361; C07C 67/287; C07C 303/30; C07C 43/29; C07C 49/84; C07C 47/575; C07C 69/92; C07C 69/736; C07C 69/738; C07C 55/54; C07C 235/60; C07C 309/66; C07C 43/225; C07C 25/13; C07C 25/18; C07C 25/22; C07D 213/69; C07D 215/20; C07D 235/24; C07D 239/96; C07D 263/58; C07D 311/22; C07D 263/56; C07B 59/001; C07B 2200/05; B01J 31/006; B01J 35/39; B01J 2231/46; C07J 1/0059; C07J 11/00

See application file for complete search history.

(56) References Cited

U.S. PATENT DOCUMENTS

| | | | |
|---|---|---|---|
| 4,483,757 | A | 11/1984 | Gardner et al. |
| 9,452,959 | B2 | 9/2016 | Hartwig et al. |

(Continued)

FOREIGN PATENT DOCUMENTS

| | | |
|---|---|---|
| CN | 2020800318516 | 2/2020 |
| JP | 2002-114735 | 4/2002 |

(Continued)

OTHER PUBLICATIONS

Tay, N. and D. Nicewicz, "Cation Radical Accelerated Nucleophilic Aromatic Substitution via Organic Photoredox Catalysis", J Am Chem Soc (2017), 139: pp. 16100-16104. (Year: 2017).*

(Continued)

*Primary Examiner* — Kamal A Saeed
*Assistant Examiner* — Sagar Patel
(74) *Attorney, Agent, or Firm* — J. Clinton Wimbish; Maynard Nexsen PC

(57) ABSTRACT

The invention generally relates to methods of making substituted arenes via direct C—H, C—O, C—S, or C—N bond conversion and methods of synthesizing isotopically-labeled substituted arenes via direct carbon-halogen bond conversion. The invention also relates to anaerobic catalyst systems comprising an acridinium photocatalyst and a nucleophile selected from a halide, a cyanide, and an isotopically-labeled amine. This abstract is intended as a scanning tool for purposes of searching in the particular art and is not intended to be limiting of the present invention.

12 Claims, 22 Drawing Sheets

(51) Int. Cl.

| | |
|---|---|
| *C07C 303/30* | (2006.01) |
| *C07D 213/69* | (2006.01) |
| *C07D 215/20* | (2006.01) |
| *C07D 231/56* | (2006.01) |
| *C07D 235/24* | (2006.01) |
| *C07D 239/96* | (2006.01) |
| *C07D 263/56* | (2006.01) |
| *C07D 263/58* | (2006.01) |
| *C07D 311/22* | (2006.01) |
| *C07J 1/00* | (2006.01) |
| *C07J 11/00* | (2006.01) |

(56) References Cited

U.S. PATENT DOCUMENTS

2012/0171111 A1 7/2012 Ohkubo et al.
2018/0148414 A1* 5/2018 Nicewicz ............. C07D 231/38

FOREIGN PATENT DOCUMENTS

JP 2005-145853 6/2005
WO WO-2016/196816 A1 12/2016
WO PCT/US2020/020232 2/2020

OTHER PUBLICATIONS

U.S. Appl. No. 62/170,632, filed Jun. 3, 2015, David Nicewicz (The University of North Carolina at Chapel Hill).

U.S. Appl. No. 15/826,092 (U.S. Pat. No. 10,399,947), filed Jun. 2, 2016 (Sep. 3, 2019), David Nicewicz (The University of North Carolina at Chapel Hill).

U.S. Appl. No. 16/506,901 (2020/0002284 A1), filed Jun. 2, 2016 (Jan. 2, 2020), David Nicewicz (The University of North Carolina at Chapel Hill).

U.S. Appl. No. 62/812,179, filed Feb. 28, 2019, Zubo Li (The University of North Carolina at Chapel Hill).

Allen et al., N-Acyloxyphthalimides as Nitrogen Radical Precursors in the Visible Light Photocatalyzed Room Temperature C—H Amination of Arenes and Heteroarenes. J Am Chem Soc. 2014; 136(15):5607-10.

Almarasson, Ö. et al., Crystal Engineering of the Composition of Pharmaceutical Phases. Do Pharmaceutical Co-crystals Represent a New Path to Improved Medicines? The Royal Soc Chem. 2004; 1889-96.

Antonchick et al., Organocatalytic, Oxidative, Intramolecular C—H Bond Amination and Metal-free Cross-Amination of Unactivated Arenes at Ambient Temperature. Angew Chem Int Ed Engl. 2011; 50(37): 8605-8.

Belfield et al., Recent synthetic advances in the nucleophilic amination of benzenes. Tetrahedron. 1999; 55(38):11399-428.

Benniston, et al. (2005) "Charge Shift and Triplet State Formation in the 9-Mesityl-10-methylacridinium Cation," J. Am. Chem. Soc. 127: 16054-16064.

Benniston, et al. (2008) "Comment: Electron-transfer reactions in the 9-mesityl-10-methylacridinium ion: impurities, triplet states and infinitely long-lived charge-shift states?" Phys Chem Chem Phys. 10(33):5156-8.

Brachet et al., Visible light C—H amidation of heteroarenes with benzoyl azides. Chem Sci., 2015; 6: 987-92.

Fukuzumi, et al. (2004) "Electron-Transfer State of 9-Mesityl-10-methylacridinium Ion with a Much Longer Lifetime and Higher Energy Than That of the Natural Photosynthetic Reaction Center" J. Am. Chem. Soc. 126: 1600-1601.

Fukuzumi, et al. (2014) "Long-Lived Charge Separation and Applications in Artificial Photosynthesis, "Acc. Chem. Res. 47: 1455-1464.

Gendron, et al. (2018), "Ring-Closing Synthesis of Dibenzothiophene Sulfonium Salts and Their Use as Leaving Groups for Aromatic 18F-Fluorination" J. Am. Chem. Soc. (2018), doi:10.1021/jacs.8b06730.

Hamilton, D.S. and Nicewicz, D.A. et al., Direct Catalytic Anti-Markovnikov Hydroetherification of Alkenols. J Am Chem Soc. 2012; 134(45): 18577-80.

Hartwig, Evolution of a Fourth Generation Catalyst for the Amination and Thioetherification of Aryl Halides. Acc Chem Res. 2008; 41(11):1534-44.

Ichiishi, et al. (2014) "Copper-Catalyzed [18F]Fluorination of (Mesityl)(aryl)iodonium Salts," Org. Lett. 16, 3224-3227 (2014).

Lee, et al. (2012) "Flouride-Derived Electrophilic Late-Stage Fluorination Reagent for PET Imaging," *Science* 334: 639-642.

Lee, et al. (2012) "Nickel-Mediated Oxidative Fluorination for PET Aqueous [$^{18}$F] Flouride," *J. Am. Chem. Soc.,* 134: 17456-17458.

Lee, et al. (2015) "Virtually instantaneous, room-temperature [(11)C]-cyanation using biaryl phosphine Pd(0) complexes," J. Am. Chem. Soc. 137: 648-651.

Liwosz, T. et al., Copper-Catalyzed Synthesis of N-Aryl and N-Sulfonyl Indoles from 2-Vinylanilines with 02 as Terminal Oxidant and TEMPO as Co-Catalyst. Synlett. 2014; 26(3):33.

Makaravage, et al. (2016) "Copper-Mediated Radiofluorinationof Arylstannanes with [$^{18}$F]KF," Org. Lett. 18: 5440-5443.

Matsubara et al., Synthesis of Anthranilic Acid Derivatives through Iron-Catalyzed Ortho Amination of Aromatic Carboxamides with N-Chloroamines. J Am Chem Soc. 2014; 136(2): 646-9.

McCammant, et al. (2017), "Cu-Mediated C—H 18F-Fluorination of Electron-Rich (Hetero)arenes," Org. Lett. 19, 3939-3942.

McManus, et al., Direct C—H Cyanation of Arenes via Organic Photoredox Catalysis, J Am Chem Soc 2017; 139: 2880-2883.

Morofuji et al., Direct C—N Coupling of Imidazoles with Aromatic and Benzylic Compounds via Electrooxidative C—H Functionalization. J Am Chem Soc. 2014; 136(12): 4496-9.

Mossine, et al. (2015) "Synthesis of [$^{18}$F]Arenes via the Cooper-Mediated [$^{18}$F]Fluorination of Boronic Acids," Org. Lett. 17: 5780-5783.

Narayanam (2017) "Synthesis of [18F]Fluoroarenes via Nucleophilic Radiofluorination of N-Arylsydnones," Angew. Chem. Int. Ed. 56, 13006-13010.

Neumann, et al. (2016) "Concerted nucleophilic aromatic substitution with 19F- and 18F-" Nature 534: 369-373.

Nguyen et al., Anti-Markovnikov hydroamination of alkenes catalyzed by a two-component organic photoredox system: direct access to phenethylamine derivatives. Angew Chem Int Ed Engl. 2014; 53(24):6198-201.

Nguyen et al., Anti-Markovnikov Hydroamination of Alkenes Catalyzed by an Organic Photoredox System. J Am Chem Soc. 2013; 135(26): 9588-91.

Nicewicz et al., Recent Applications of Organic Dyes as Photoredox Catalysts in Organic Synthesis. ACS Catal. 2014; 4(1): 355-60.

Ohkubo, et al. Selective photocatalytic aerobic bromination with hydrogen bromidevia an electron-transfer state of 9-mesityl-10-methylacridinium ion. Chem Sci. 2011; 2(4): 715-22.

Ohkubu et al., Oxygenation and chlorination of aromatic hydrocarbons with hydrochloric acid photosensitized by 9-mesityl-10-methylacridinium under visible light irradiation. Res Chem Intermed. 2013; 39:205-20.

Pan, et al. (1993) "Hydroxyl-radical-induced oxidation of cyclohexa-1,4-diene by O2 in aqueous solution. A pulse radiolysis and product study," J. Chem. Soc. Perkin Trans. 2: 9.

Perkowshi et al., Direct Catalytic Anti-Markovnikov Addition of Carboxylic Acids to Alkenes. J Am Chem Soc. 2013; 135(28):10334-7.

Preshlock, et al. (2016) "$^{18}$F-Labeling of Arenes and Heteroarenes for Application in Positron Emission Tomography," Chem. Rev. 116: 719-766.

Prier et al., Visible Light Photoredox Catalysis with Transition Metal Complexes: Applications in Organic Synthesis. Chem Rev. 2013; 113(7): 5322-63 (141 pages).

PubChem-SID 184611234, "9-Mesityl-2, 7-dimethyl-10-phenylacridin-10-ium tetrafluoroborate" (2014); p. 3.

Romero, et al. (2014) "Mechanistic insight into the photoredox catalysis of anti-markovnikov alkene hydrofunctionalization reactions," J. Am. Chem. Soc. 136: 17024-17035.

(56) References Cited

OTHER PUBLICATIONS

Schimler, et al. (2017) "Nucleophilic Deoxyfluorination of Phenols via Aryl Fluorosulfonate Intermediates," Journal of the American Chemical Society 139: 1452-1455.

Shrestha et al., Sterically Controlled, Palladium-Catalyzed Intermolecular Amination of Arenes. J Am Chem Soc. 2013; 135(23): 8480-3.

Simon M. Ametamey, et al. (2008) "Molecular imaging with PET," Chem. Rev. 108: 1501-1516.

Surry and Buchwald et al., Dialkylbiaryl phosphines in Pd-catalyzed amination: a user's guide. Chem Soc. 2011; 2(1): 27-50 (70 pages).

Tay, et al., Cation Radical Accelerated Nucleophilic Aromatic Substitution via Organic Photoredox Catalysis, J Am Chem Soc 2017; 139: 16100-16104.

Teare, et al. (2010) "Radiosynthesis and Evaluation of [$^{18}$F]Selectfluor bis(triflate)" Angew. Chem. Int. Ed. 49, 6821-6824.

Tran, L.D. et al., Directed Amination of Non-Acidic Arene C—H Bonds by a Copper-Silver Catalytic System. Angew Chem Int Ed Engl. 2013; 52(23):6043-6.

Tredwell, et al. (2012) 18F Labeling of Arenes, Angew Chem Int Ed 2012; 51: 11426-11437.

Tedwell, et al. (2014) "A General Copper-Mediated Nucleophilic 18F Fluorination of Arenes," Angew. Chem. Int. Ed. 53, 7751-7755.

Truong, et al. (2013) "Copper-catalyzed, directing group-assisted fluorination of arene and heteroarene C—H bonds," Journal of the American Chemical Society 135: 9342-9345.

Tsang et al., Combined C—H Functionalization/C—N Bond Formation Route to Carbazoles. J Am Chem Soc. 2005; 127:14560-1.

Wang (2009) Versatile $Pd(OTf)_2$ $2H_2O$-Catalyzed ortho-Fluorination Using NMP as a Promoter, Am Chem Soc. 131(22):7520-7521.

Xue, D. et al., Direct arylation of N-Heteroarenes with Aryldiazonium salts by Photoredox Catalysis in Water. Chem Eur J. 2014; 20(10):2960-5.

Yan, et al., Recent advances in radical-mediated florination through C—H and C—C bond cleavage, Science China Chemistry, 2017; 60(2): 214-222.

Yamamoto, et al. (2018) "Palladium-Catalysed Electrophilic aromatic C—H Fluorination," Nature 554(7693): 511-514.

Fessenden, Ralph J. et al., Organic Chemistry, 5th edition, Brooks/Cole Publishing Co., 3 pages, ISBN 0-534-20028-1.

* cited by examiner

OTHER SUBSTRATES 34.4% RCY tyrosine 70.4% RCY estrone 32.2% RCY

| *Acridinium Catalysts (X = N; $R^3$ = Me):* | $E_{1/2}^{red}$ | $^*E_{1/2}^{red}$ |
|---|---|---|
| 2.1; R = Me; $R^1$ = $R^2$ = H | −0.55 V | +2.12 V |
| 2.2; R = Ph; $R^1$ = H; $R^2$ = Me | −0.58 V | +2.09 V |
| 2.3; R = Ph; $R^1$ = *t*-Bu; $R^2$ = H | −0.54 V | +2.15 V |
| 2.4; R = Ph; $R^1$ = $R^2$ = H | −0.50 V | +2.17 V |
| 2.5; R = 4-$FC_6H_4$; $R^1$ = $R^2$ = H | −0.46 V | +2.21 V |
| 2.6; R = Me; $R^1$ = $C_6F_5$; $R^2$ = H | −0.24 V | +2.43 V |

| *Xanthenylium Catalysts (X = O):* | $E_{1/2}^{red}$ | $^*E_{1/2}^{red}$ |
|---|---|---|
| 2.7; $R^1$ = H; $R^3$ = Me | +0.12 V | +2.79 V |
| 2.8; $R^1$ = *t*-Bu; $R^3$ = Me | −0.07 V | +2.60 V |
| 2.9; $R^1$ = *t*-Bu; $R^3$ = F | −0.07 V | +2.46 V |

1
Diphenyl ether
CsF
(10eq)
1a
1b
Catalyst A

Catalyst A

Catalyst B

Catalyst C

Catalyst D

Catalyst E

Catalyst F

Catalyst G

Catalyst H

Catalyst I

Catalyst J

Catalyst K

Catalyst L

A. Prior method: transition metal-catalyzed (hetero)arene radiolabeled (hetero)arene X = Halogen, OTf

[M] = Pd(IV), Ni(II), $B(OR)_2$, $I(OR)_3$,...

B. This work: organic photoredox catalysis (hetero)arene radiolabeled (hetero)arene

[O]:

organic photoredox catalyst

Cat-1

Cat-2

Cat-3

Cat-4

Cat-5

Cat-6

Cat-7

Cat-8

Cat-9

Cat-10

Cat-11

Cat-12

Cat-13

Cat-14

Cat-15

Cat-16

Cat-17

Cat-18

$Ru(bpy)_3(PF_5)_2$

Cat-19

Cat-20

Cat-21

Cat-22

Cat-23

Cat-24

Cat-25

Cat-26

Cat-27

Cat-28

Cat-29

Cat-30

Cat-31

Cat-32

Cat-33

Cat-34

Cat-35

Cat-36

Cat-37

Cat-38

Cat-39

Cat-40

Cat-41

Cat-42

Cat-43

Cat-44

Cat-45

Cat-46

Cat-47

Cat-48

Substrate Scope 1 8.6% (39.3%)
2 2.9% (15.1%)
3 23% (20.9%)
4 14.5% (50.0%)
5 5.5% (3.7%)
6 16.2% (11.1%)
7 7.6% (6.6%)
8 2.1% (3.9%)
9 2.6% (5.7%)
10 6.0% (8.3%)
11 10.6% (5.6%)
12 20.2% (23.5%)
13 25.4% (24.6%)
14 15.6% (13.8%)
15 19.8% (23.5%)
16 20.0% (-)
17 27.5% (17.9%)
18 7.8% (7.1%)
19 16.6% (11.1%)
20 19.5% (38.2%)
21 33.8% (39.6%)
22 14.5% (8.7%)

DIRECT AROMATIC CARBON-OXYGEN AND CARBON-HYDROGEN BOND FUNCTIONALIZATION VIA ORGANIC PHOTOREDOX CATALYST

CROSS-REFERENCE TO RELATED APPLICATIONS

This Application is a national phase application under 35 U.S.C. § 371 of International Application No. PCT/US2020/020232, filed on Feb. 27, 2020, which claims the benefit of U.S. Application No. 62/812,179, filed on Feb. 28, 2019, the contents of which are hereby incorporated by reference in their entireties.

STATEMENT REGARDING FEDERALLY SPONSORED RESEARCH

This invention was made with government support under Grant Nos. GM120186 and EB014354 awarded by the National Institutes of Health. The government has certain rights in the invention.

BACKGROUND

Aromatic fluorination has attracted extensive attention in pharmaceutical and agrochemical drug development, leading to a significant need to develop simple fluorination methods. While a variety of cross-coupling methods for [$^{19}$F]C—F bond formation from aryl halides, triflates, boronic acids and stannanes has been recently developed (Lee et al. (2011) *Science* 334: 639-642; Lee et al. (2012) *J. Am. Chem. Soc.* 134: 17456-17458; Mossine et al. (2014) *Org. Lett.* 17: 5780-5783; Makaravage et al. (2016) *Org. Lett.* 18: 5440-5443), only a limited number of examples of direct ortho C—H fluorination of aromatics have been reported. However, such ortho C—H fluorination methods rely on non-removable templating groups to direct reactivity and require electrophilic fluorination sources (Wang et al. (2009) *J Am Chem Soc.* 131(22):7520-7521; Yamamoto et al. (2018) *Nature* 554(7693): 511-514). Recently, the development of one of the first C—H fluorination reactions of aromatics was reported; however, an electrophilic fluorinating agent (i.e., Selectfluor or NFSI) is required (Lee et al. (2011) *Science* 334(6056): 639-642).

The generation of $^{18}$F-labeled pharmaceutical compounds is of particular interest. Such compounds could quantitatively measure site-specific chemical reactions, including their spatial distributions and metabolic perturbations, and the ensuing biological processes in vivo through positron emission tomography (PET). Despite the exceptional promise of PET imaging, the availability of PET agents is limited in many situations due to the lack of efficient and simple labeling methods to modify biologically active molecules. [$^{18}$F]-fluoride is the most widely used PET isotope in the clinic; however, the efficient introduction of fluorine into inactivated aromatic molecules remains a significant challenge, which limits the development of novel tracers. Several arene precursors such as triarylsulfonium and trimethylanilinium triflates salts, diarylsulfoxides, diarylselenones, and spirocyclic iodonium ylides have been successfully applied to the arene $^{18}$F-fluoritation via $S_NAr$ reaction (Preshlock et al. (2016) *Chem. Rev.* 116: 719-766). Most recently, $^{18}$F-deoxyfluorination of phenol by a concerted $S_NAr$ reaction via uronium intermediates and nucleophilic aromatic substitution via N-arylsydnone intermediates were reported and act as practical tools in late stage labeling (Neumann et al. (2016) *Nature* 534: 369-373). Rarer still are [$^{18}$F] aromatic fluorination reactions. Indeed, the state of the art methods require either preformed palladium or nickel arene complexes from the requisite aromatic halides or the corresponding aryl boronic acids (Lee et al. (2011) *Science* 334: 639-642; Lee et al. (2012) *J. Am. Chem. Soc.* 134: 17456-17458). Unfortunately, these approaches are highly impractical for clinic technicians, either because special $O_2$-free handling techniques of arylpalladium and nickel complexes are required or because the boronic esters or other related precursors are not readily available. Moreover, the involvement of metal catalyst may also complicate the quality control process when the agents are used in humans. Further analysis needs to be done in order to demonstrate whether the residue metal is at acceptable range for translation.

In sum, despite the growing importance of fluorine-containing agents in pharmaceutical drug discovery, the development of simple direct conversion processes to access C—F bonds has remained elusive. Thus, there remains a need for direct aryl fluorination methods that occur under mild conditions and are tolerant to a wide range of substrates. In addition, the value of such methods would be significantly enhanced if the methods were applicable towards conversion using other nucleophiles, as well. These needs and others are met by the present invention.

SUMMARY

In accordance with the purpose(s) of the invention, as embodied and broadly described herein, the invention, in one aspect, relates to methods of synthesizing a substituted arene via direct C—H, C—O, C—S, or C—N bond conversion and methods of synthesizing isotopically-labeled substituted arenes via direct carbon-halogen bond conversion.

Thus, disclosed are methods of making a compound having a structure represented by a formula:

$$Ar^1—Z,$$

wherein Z is selected from halogen, —CN, —$NH_2$, C1-C4 alkylamino, and (C1-C4)(C1-C4) dialkylamino, provided that when Z is —$NH_2$, C1-C4 alkylamino, or (C1-C4)(C1-C4) dialkylamino that Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{15b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{30}$ and $R^{32}$, when present, is independently selected from hydrogen and C1-C4 alkyl; wherein each of $R^{31a}$ and $R^{31b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

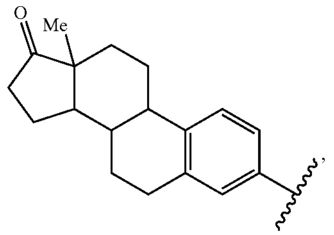 [SMILES: *c1ccc2c(c1)CCC1C2CCC2(C)C(=O)CCC12]

the method comprising the step of reacting an arene having a structure represented by a formula:

$Ar^1$-E, wherein E is an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, and under anaerobic conditions, thereby forming the compound.

Also disclosed are catalyst systems comprising an acridinium photocatalyst and a nucleophile selected from a halide, a cyanide, and an isotopically-labeled amine, wherein the catalyst system is anaerobic.

Also disclosed are methods of making a compound having a structure represented by a formula:

$Ar^1$—Z, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

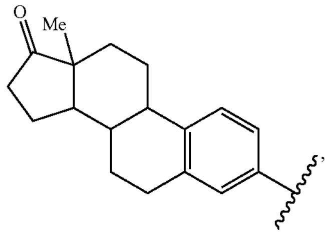 [SMILES: *c1ccc2c(c1)CCC1C2CCC2(C)C(=O)CCC12]

the method comprising the step of reacting an arene having a structure represented by a formula:

$Ar^1$-E, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, thereby forming the compound.

Also disclosed are methods of making a compound having a structure represented by a formula:

$Ar^1$—Z, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

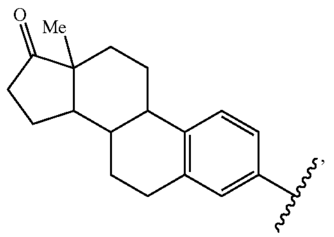

the method comprising the step of reacting an arene having a structure represented by a formula:

$Ar^1$-E, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)O$R^{20}$, —OC(═O)S$R^{20}$, —OC(═O)NH$R^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, thereby forming the compound.

Also disclosed are methods of making a compound having a structure represented by a formula:

$Ar^1$—Z, wherein Z is halogen and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)O$R^{11}$, —C(═O)N$R^{12a}R^{12b}$, $Ar^2$, —O$Ar^2$, —C(═O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

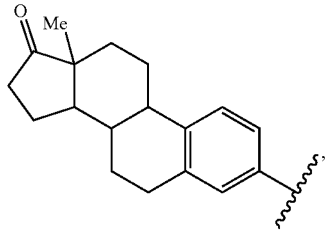 [SMILES: *c1ccc2c(c1)CCC1C2CCC2(C)C(=O)CCC12]

the method comprising the step of reacting an arene having a structure represented by a formula:

$Ar^1$—H, with a halide, in the presence of a LED having a wavelength of about 425 nm, TBPA, and a catalytically effective amount of an acridinium photocatalyst having a structure:

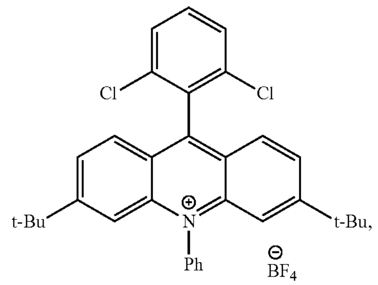

thereby forming the compound.

Also disclosed are methods of making a compound having a structure represented by a formula:

$Ar^1$—X, wherein X is halogen and wherein X contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)O$R^{11}$, —C(═O)N$R^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

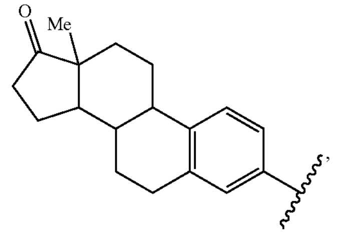 [SMILES: *c1ccc2c(c1)CCC1C2CCC2(C)C(=O)CCC12]

the method comprising the step of reacting an arene having a structure represented by a formula:

$Ar^1$—X', wherein X' is halogen and wherein X' does not contain a radioisotope, with a nucleophile selected from a halide, a cyanide, and an amine, in the presence of a catalytically effective amount of an acridinium photocatalyst, thereby forming the compound.

Also disclosed are catalyst systems comprising an acridinium photocatalyst and a nucleophile selected from a halide, a cyanide, and an isotopically-labeled amine, wherein the catalyst system is anaerobic.

Also disclosed are catalyst systems comprising an acridinium photocatalyst, an isotopically-labeled halide, and an oxidant.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1:
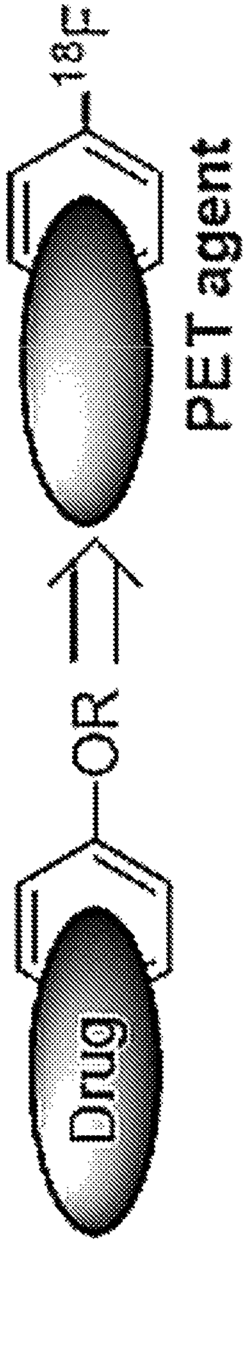
FIG. 1 shows a representative schematic illustrating the direct conversion of phenol derivatives to aromatic fluorides for PET imaging purposes.

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an", and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "catalytically effective" refers to the amount of a catalyst that is sufficient to facilitate a reaction (e.g., C—H and/or C—O functionalization) as disclosed herein).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, for example, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized $\pi$ electrons above and below the plane of the molecule, where the $\pi$ clouds contain $(4n+2)$ $\pi$ electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C-A^2-C(O)O)_a—$ or $-(A^1O(O)C-A^2-OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, I, or At.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo [c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2, or 3 ring heteroatoms or wherein a pyridine ring is fused to a 5- or a 6-membered ring containing 1, 2, or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-4}O(CH_2)_{0-1}Ph$ which may be substituted with $R^o$; —CH═CHPh, which may be substituted with $R^o$; $—(CH_2)_{0-4}O(CH_2)_{0-1}$-pyridyl which may be substituted with $R^o$; $—NO_2$; —CN; $—N_3$; $—(CH_2)_{0-4}N(R^o)_2$; $—(CH_2)_{0-4}N(R^o)C(O)R^o$; $—N(R^o)C(S)R^o$; $—(CH_2)_{0-4}N(R^o)C(O)NR^o_2$; $—N(R^o)C(S)NR^o_2$; $—(CH_2)_{0-4}N(R^o)C(O)OR^o$; $—N(R^o)N(R^o)C(O)R^o$; $—N(R^o)N(R^o)C(O)NR^o_2$; $—N(R^o)N(R^o)C(O)OR^o$; $—(CH_2)_{0-4}C(O)R^o$; $—C(S)R^o$; $—(CH_2)_{0-4}C(O)OR^o$; $—(CH_2)_{0-4}C(O)SR^o$; $—(CH_2)_{0-4}C(O)OSiR^o_3$; $—(CH_2)_{0-4}OC(O)R^o$; $—OC(O)(CH_2)_{0-4}SR—$, $SC(S)SR^o$; $—(CH_2)_{0-4}SC(O)R^o$; $—(CH_2)_{0-4}C(O)NR^o_2$; $—C(S)NR^o_2$; $—C(S)SR^o$; $—SC(S)SR^o$, $—(CH_2)_{0-4}OC(O)NR^o_2$; $—C(O)N(OR^o)R^o$; $—C(O)C(O)R^o$; $—C(O)CH_2C(O)R^o$; $—C(NOR^o)R^o$; $—(CH_2)_{0-4}SSR^o$; $—(CH_2)_{0-4}S(O)_2R^o$; $—(CH_2)_{0-4}S(O)_2OR^o$; $(CH_2)_{0-4}OS(O)_2R^o$; $—S(O)_2NR^o_2$; $—(CH_2)_{0-4}S(O)R^o$; $—N(R^o)S(O)_2NR^o_2$; $—N(R^o)S(O)_2R^o$; $—N(OR^o)R^o$; $—C(NH)NR^o_2$; $—P(O)_2R^o$; $—P(O)R^o_2$; $—OP(O)R^o_2$; $—OP(O)(OR^o)_2$; $SiR^o_3$; $—(C_{1-4}$ straight or branched alkylene$)O—N(R^o)_2$; or $—(C_{1-4}$ straight or branched alkylene$)C(O)O—N(R^o)_2$, wherein each $R^o$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), is independently halogen, $—(CH_2)_{0-2}R^•$, $-(haloR^•)$, $—(CH_2)_{0-2}OH$, $—(CH_2)_{0-2}OR$, $—(CH_2)_{0-2}CH(OR^•)_2$; $—O(haloR^•)$, —CN, $—N_3$, $—(CH_2)_{0-2}C(O)R^•$, $—(CH_2)_{0-2}C(O)OH$, $—(CH_2)_{0-2}C(O)OR^•$, $—(CH_2)_{0-2}SR^•$, $—(CH_2)_{0-2}SH$, $—(CH_2)_{0-2}NH_2$, $—(CH_2)_{0-2}NHR^•$, $—(CH_2)_{0-2}NR^•_2$, $—NO_2$, $—SiR^•_3$, $—OSiR^•_3$, $—C(O)SR^•$, $—(C_{1-4}$ straight or branched alkylene$)C(O)OR^*$, or $—SSR^•$ wherein each $R^•$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include ═O and ═S.

Suitable divalent substituents on a saturated carbon atom of an "optionally substituted" group include the following: ═O, ═S, $═NNR^*_2$, $═NNHC(O)R^*$, $═NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $R^•$, -(halo$R^•$), —OH, $—OR^•$, —O(halo$R^•$), —CN, —C(O)OH, $—C(O)OR^•$, $—NH_2$, $—NHR^•$, $—NR^•_2$, or $—NO_2$, wherein each $R^•$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^†$, $—NR^†_2$, $—C(O)R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, $—R^•$, -(halo$R^•$), —OH, $—OR^•$, —O(halo$R^•$), —CN, —C(O)OH, $—C(O)OR^•$, $—NH_2$, $—NHR^•$, $—NR^•_2$, or $—NO_2$, wherein each $R^•$ is unsubstituted or where preceded by "halo" is substituted only with one or more halogens, and is independently C4 aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

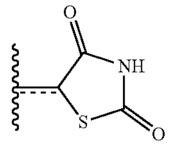

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

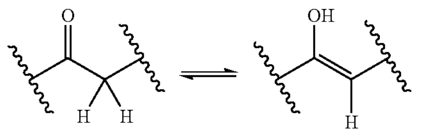

keto form enol form

-continued

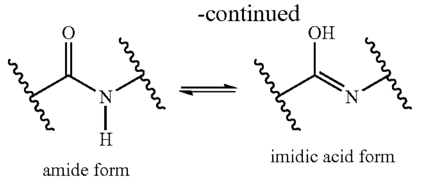

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

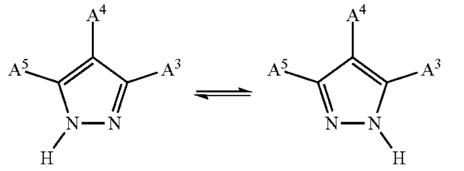

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

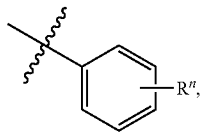

which is understood to be equivalent to a formula:

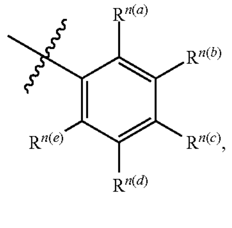

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are compounds that can be prepared by the disclosed methods (e.g., compounds prepared by converting a carbon-hydrogen, carbon-oxygen, carbon-sulfur, or carbon-nitrogen bond into a carbon-carbon, carbon-halogen, or isotopically-labeled carbon-nitrogen bond and compounds prepared by converting a carbon-halogen bond into an isotopically-labeled carbon-halogen bond). It is contemplated that each disclosed derivative can be optionally further substituted. It is also contemplated that any one or more derivative can be optionally omitted from the invention. It is understood that a disclosed compound can be provided by the disclosed methods.

1. Structure

In one aspect, disclosed are compounds having a structure represented by a formula:

$Ar^1$—Z, wherein Z is selected from halogen, —CN, —$NH_2$, C1-C4 alkylamino, and (C1-C4)(C1-C4) dialkylamino, provided that when Z is —$NH_2$, C1-C4 alkylamino, or (C1-C4)(C1-C4) dialkylamino that Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-$C_4$ alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, $C_1$-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

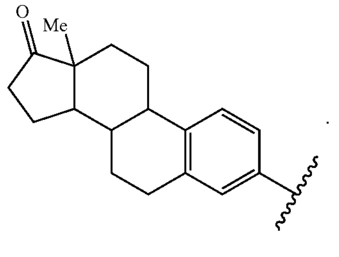 [SMILES: *c1ccc2c(c1)CCC1C2CCC2(C)C(=O)CCC12]

In one aspect, disclosed are compounds having a structure represented by a formula:

$Ar^1$—Z, wherein Z is selected from halogen, —CN, —$NH_2$, C1-C4 alkylamino, and ($C_1$-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

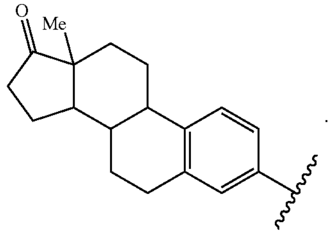 [SMILES: *c1ccc2c(c1)CCC1C2CCC2(C)C(=O)CCC12]

In one aspect, disclosed are compounds having a structure represented by a formula:

$Ar^1$—Z, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

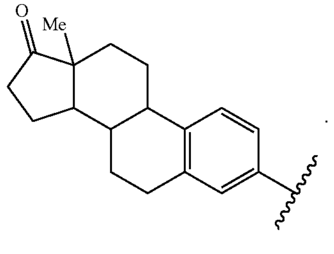 [SMILES: *c1ccc2c(c1)CCC1C2CCC2(C)C(=O)CCC12]

In one aspect, disclosed are compounds having a structure represented by a formula:

$Ar^1$—Z, wherein Z is halogen and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(=O)$R^{10}$, —C(=O)$OR^{11}$, —C(=O)$NR^{12a}R^{12b}$, $Ar^2$, —$OAr^2$, —C(=O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

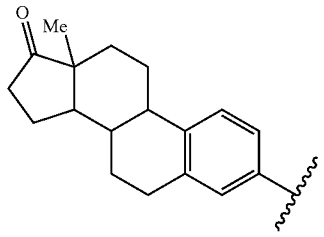

.

In one aspect, disclosed are compounds having a structure represented by a formula:

$Ar^1$—X, wherein X is halogen and wherein X contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(=O)$R^{10}$, —C(=O)$OR^{11}$, —C(=O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

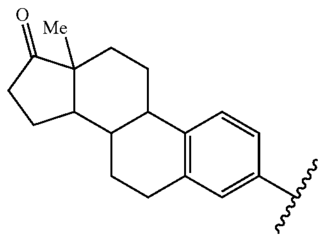

.

In a further aspect, the compound has a structure represented by a formula:

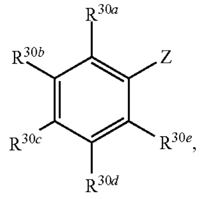

wherein each of $R^{30a}$, $R^{30b}$, $R^{30c}$, $R^{30d}$, and $R^{30e}$, is independently selected from hydrogen, halogen, —CN, —$NO_2$, C1-C8 alkyl, C1-C8 alkoxy, —O—(C1-C8 alkyl)-$CO_2$—(C1-C8 alkyl), —C(=O)$R^{10}$, —C(=O)$OR^{11}$, —C(=O)$NR^{12a}R^{12b}$, $Ar^2$, and —$CH_2CR^{13}(NR^{14a}R^{14b})CO_2R^{15}$, or wherein any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, —C(=O)$R^{10}$, —C(=O)$OR^{11}$, —C(=O)$NR^{12a}R^{12b}$, $Ar^2$, and —$CH_2CR^{13}(NR^{14a}R^{14b})CO_2R^{15}$.

In a further aspect, a compound has a structure represented by a formula selected from:

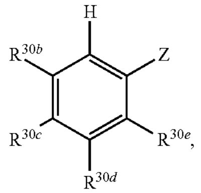

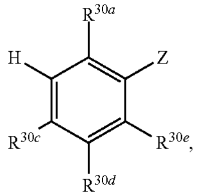

and

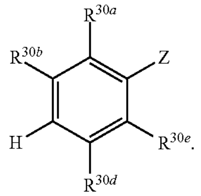

In a further aspect, a compound has a structure represented by a formula:

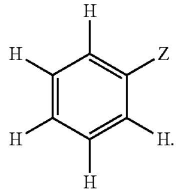

In a further aspect, the compound has a structure represented by a formula:

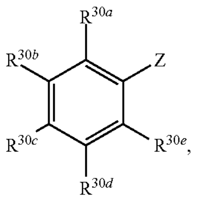

wherein Z is selected from —CN and halogen.

In a further aspect, the compound has a structure represented by a formula:

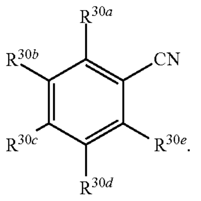

In a further aspect, the compound has a structure represented by a formula:

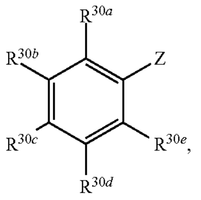

wherein Z is halogen.

In a further aspect, a compound has a structure represented by a formula selected from:

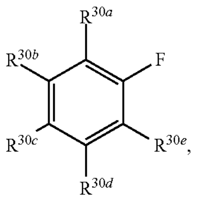 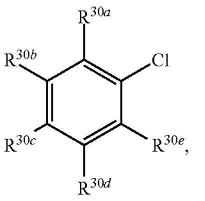 and

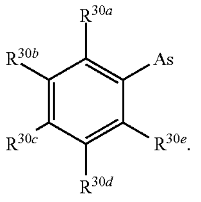

In a further aspect, the compound has a structure represented by a formula:

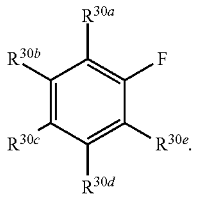

In a further aspect, the compound has a structure represented by a formula:

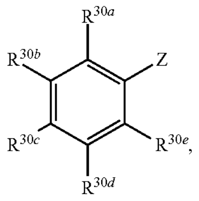

wherein Z is selected from —$NH_2$, C1-C4 alkylamino, and (C1-C4)(C1-C4) dialkylamino.

In a further aspect, the compound has a structure represented by a formula selected from:

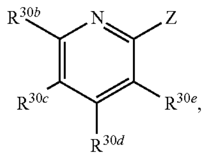 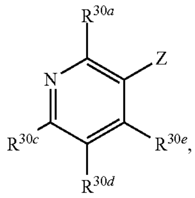 and

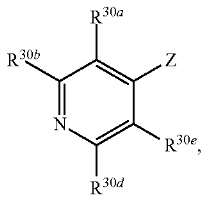

wherein each of $R^{30a}$, $R^{30b}$, $R^{30c}$, $R^{30d}$, and $R^{30e}$, when present, is independently selected from hydrogen, halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$, or wherein any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$.

In a further aspect, a compound has a structure represented by a formula selected from:

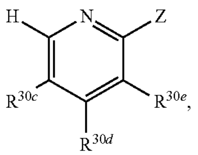
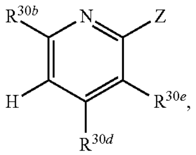
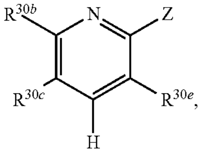
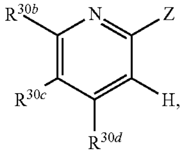
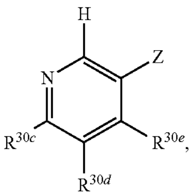
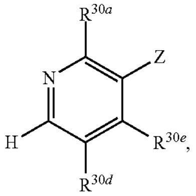
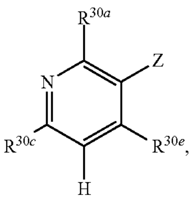
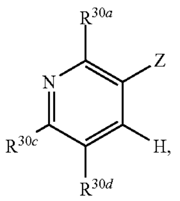
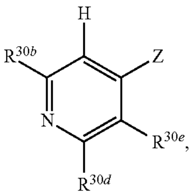
and
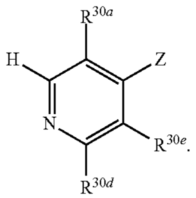

In a further aspect, a compound has a structure represented by a formula selected from:

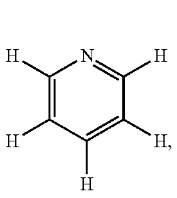
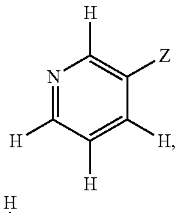
and
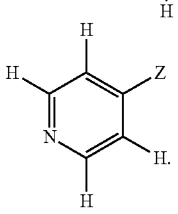

In a further aspect, the compound has a structure represented by a formula selected from:

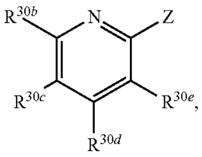
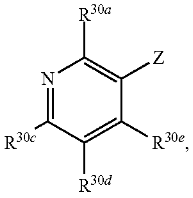
and
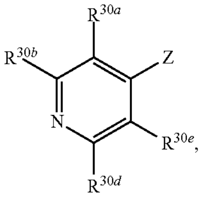

wherein Z is selected from —CN and halogen.

In a further aspect, the compound has a structure represented by a formula:

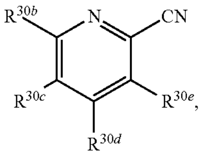
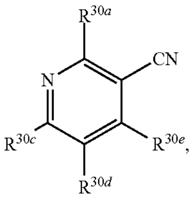
and
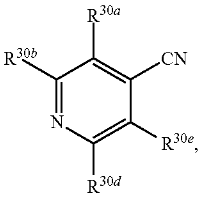

In a further aspect, the compound has a structure represented by a formula:

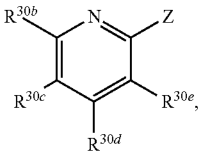
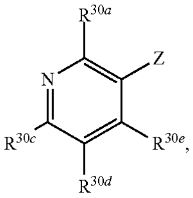
and
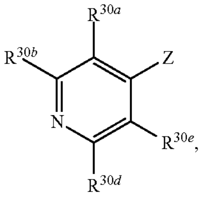

wherein Z is halogen.

In a further aspect, a compound has a structure represented by a formula selected from:

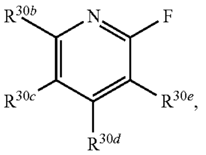
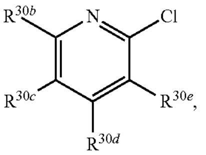
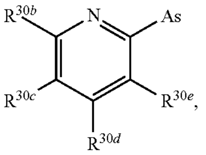
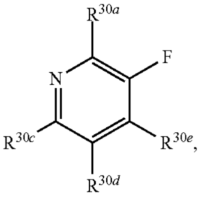
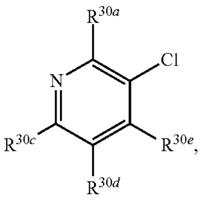
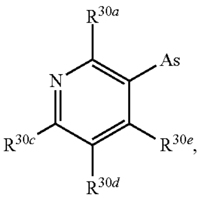
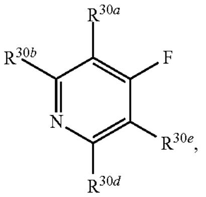
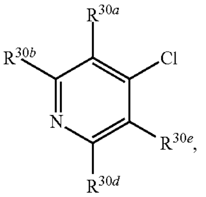
and
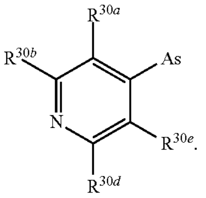

In a further aspect, the compound has a structure represented by a formula:

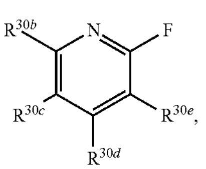
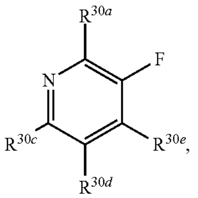
and
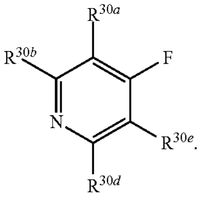

In a further aspect, the compound has a structure represented by a formula:

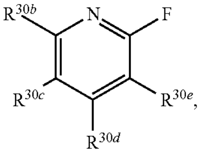
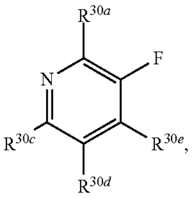
and
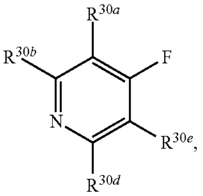

wherein Z is selected from —$NH_2$, C1-C4 alkylamino, and (C1-C4)(C1-C4) dialkylamino.

In a further aspect, the compound has a structure selected from:

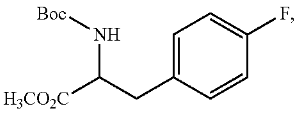
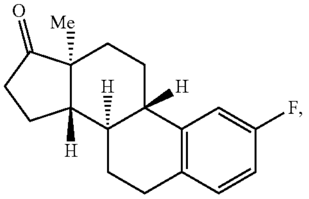
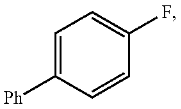
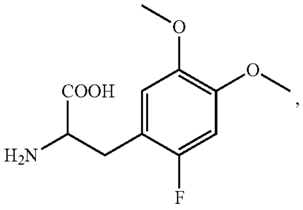
and
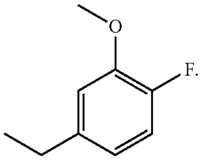

In a still further aspect, the fluorine is $^{18}F$.

In a further aspect, the compound has a structure selected from:

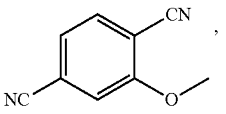
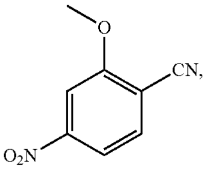
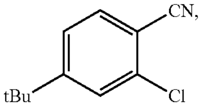
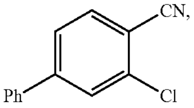

-continued
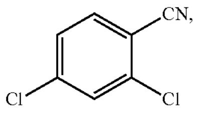 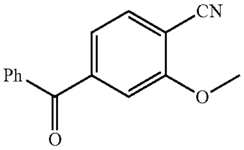 ,
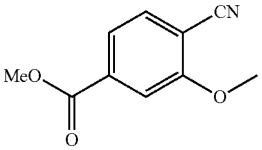 ,
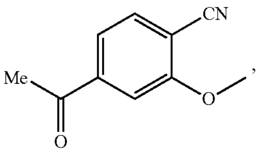 , 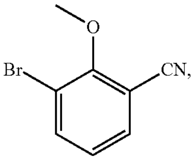
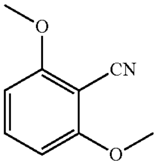 , 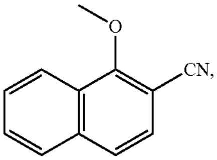
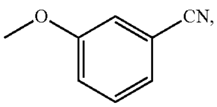 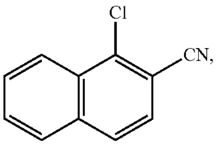
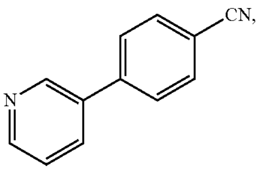 and
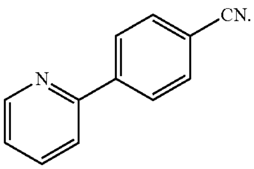
In a still further aspect, the cyanide is $^{11}CN$.
In a further aspect, the compound is selected from:
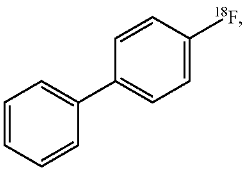 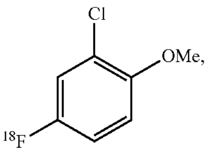
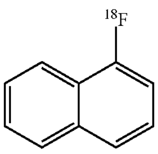 , 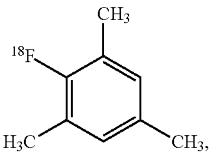
-continued
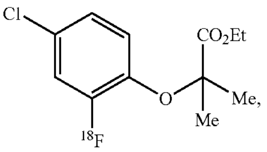 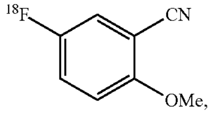
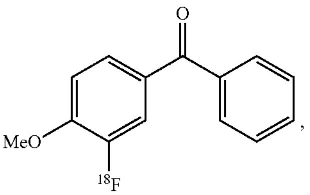
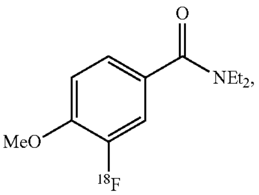 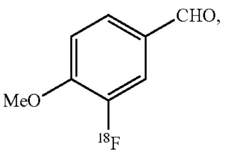
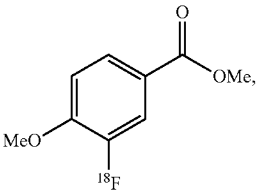
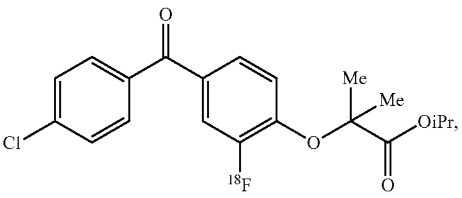
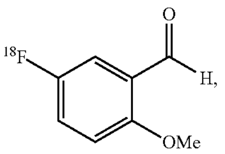 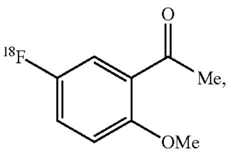
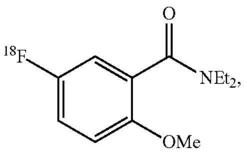 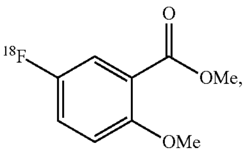
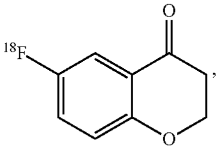 , 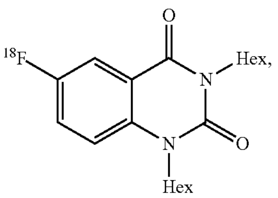
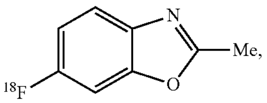
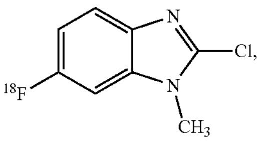

-continued

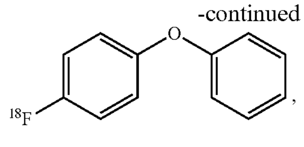

,

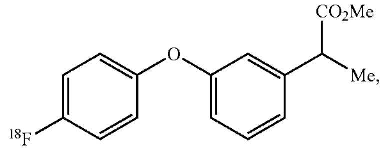

and

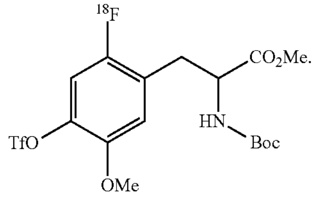

I, Z is halogen and wherein the nucleophile is a halide. In a still further aspect, Z is $^{18}F$ and wherein the nucleophile is $^{18}F$-TBAF.

a. Z Groups

In one aspect, Z is selected from halogen, —CN, —$NH_2$, C1-C4 alkylamino, and (C1-C4)(C1-C4) dialkylamino, provided that when Z is —$NH_2$, C1-C4 alkylamino, or (C1-C4)(C1-C4) dialkylamino that Z contains a radioisotope.

In one aspect, Z is selected from halogen, —CN, —$NH_2$, C1-C4 alkylamino, and (C1-C4)(C1-C4) dialkylamino and wherein Z contains a radioisotope.

In a further aspect, Z contains a radioisotope, for example, a radioisotope useful for imaging and therapy. Examples of radioisotopes include, but are not limited to, $^{18}F$, $^{11}C$, $^{34}Cl$, $^{76}Br$, $^{123}I$, $^{124}I$, $^{131}I$, $^{125}I$, and $^{211}At$, although other radioisotopes useful in imaging and therapy are also envisioned. In a still further aspect, the radioisotope is selected from $^{18}F$, $^{11}C$, $^{34}Cl$, $^{76}Br$, $^{123}I$, $^{124}I$, $^{131}I$, $^{125}I$, and $^{211}At$. In yet a further aspect, the radioisotope is selected from $^{18}F$ and $^{11}C$. In yet a further aspect, the radioisotope is $^{18}F$. In an even further aspect, the radioisotope is $^{11}C$.

In a further aspect, Z is selected from halogen and —CN. In a still further aspect, Z is selected from fluorine, chlorine, iodine, astatine, and —CN. In yet a further aspect, Z is selected from fluorine, chlorine, astatine, and —CN. In an even further aspect, Z is selected from fluorine, chlorine, and —CN. In a still further aspect, Z is selected from fluorine and —CN.

In yet a further aspect, Z is selected from fluorine, chlorine, —CN, —$NH_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, Z is selected from fluorine, chlorine, —CN, —$NH_2$, —OH, —$NHCH_3$, —$NHCH_2CH_3$, —$N(CH_3)_2$, and —$N(CH_3)(CH_2CH_3)$. In a still further aspect, Z is selected from fluorine, chlorine, —CN, —$NH_2$, —$NHCH_3$, and —$N(CH_3)_2$.

In a further aspect, Z is selected from C1-C4 alkylamino and (C1-C4)(C1-C4) dialkylamino. In yet a further aspect, Z is selected from —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, Z is selected from —$NHCH_3$, —$NHCH_2CH_3$, —$N(CH_3)_2$, and —$N(CH_3)(CH_2CH_3)$. In a still further aspect, Z is selected from —$NHCH_3$ and —$N(CH_3)_2$.

In a further aspect, Z is selected from —$NH_2$, C1-C4 alkylamino, and (C1-C4)(C1-C4) dialkylamino. In yet a further aspect, Z is selected from —$NH_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, Z is selected from —$NH_2$, —$NHCH_3$, —$NHCH_2CH_3$, —$N(CH_3)_2$, and —$N(CH_3)(CH_2CH_3)$. In a still further aspect, Z is selected from —$NH_2$, —$NHCH_3$, and —$N(CH_3)_2$.

In a further aspect, Z is selected from halogen, —CN, and —$NH_2$. In a still further aspect, Z is selected from fluorine, chlorine, —CN, and —$NH_2$.

In a further aspect, Z is selected from —CN and —$NH_2$. In an even further aspect, Z is —CN. In yet a further aspect, Z is —$NH_2$.

In a further aspect, Z is a halogen. In a still further aspect, Z is selected from fluorine, chlorine, iodine, and astatine. In yet a further aspect, Z is selected from fluorine, chlorine, and astatine. In an even further aspect, Z is selected from fluorine and chlorine. In yet a further aspect, Z is chlorine. In an even further aspect, Z is fluorine. In a still further aspect, Z is astatine.

b. $R^{10}$, $R^{11}$, $R^{12A}$, $R^{12B}$, $R^{13}$, and $R^{15}$ Groups

In one aspect, each of $R^{10}$, $R^{11}$, $R^{12a}$, $R^{12b}$, $R^{13}$, and $R^{15}$, when present, is independently selected from hydrogen and C1-C4 alkyl. In a further aspect, each of $R^{10}$, $R^{11}$, $R^{12a}$, $R^{12b}$, $R^{13}$, and $R^{15}$, when present, is independently selected from hydrogen, methyl, ethyl, n-propyl, and iso-propyl. In a still further aspect, each of $R^{10}$, $R^{11}$, $R^{12}$, $R^{12b}$, $R^{13}$, and $R^{15}$, when present, is independently selected from hydrogen, methyl, and ethyl. In yet a further aspect, each of $R^{10}$, $R^{11}$, $R^{12a}$, $R^{12b}$, $R^{13}$, and $R^{15}$, when present, is independently selected from hydrogen and ethyl. In an even further aspect, each of $R^{10}$, $R^{11}$, $R^{12a}$, $R^{12b}$, $R^{13}$, and $R^{15}$, when present, is independently selected from hydrogen and methyl. In a still further aspect, each of $R^{10}$, $R^{11}$, $R^{12a}$, $R^{12b}$, $R^{13}$, and $R^{15}$, when present, is hydrogen.

In a further aspect, each of $R^{10}$, $R^{11}$, $R^{12a}$, $R^{12b}$, $R^{13}$, and $R^{15}$, when present, is independently selected from C1-C4 alkyl. In a still further aspect, each of $R^{10}$, $R^{11}$, $R^{12a}$, $R^{12b}$, $R^{13}$, and $R^{15}$, when present, is independently selected from methyl, ethyl, n-propyl, and iso-propyl. In yet a further aspect, each of $R^{10}$, $R^{11}$, $R^{12a}$, $R^{12b}$, $R^{13}$, and $R^{15}$, when present, is independently selected from methyl and ethyl. In an even further aspect, each of $R^{10}$, $R^{11}$, $R^{12a}$, $R^{12b}$, $R^{13}$, and $R^{15}$, when present, is ethyl. In a still further aspect, each of $R^{10}$, $R^{11}$, $R^{12}$, $R^{12b}$, $R^{13}$, and $R^{15}$, when present, is methyl.

In a further aspect, $R^{11a}$ is hydrogen and $R^{11b}$ is C1-C4 alkyl. In a still further aspect, $R^{11a}$ is hydrogen and $R^{11b}$ is selected from methyl, ethyl, n-propyl, and iso-propyl. In yet a further aspect, $R^{11a}$ is hydrogen and $R^{11b}$ is selected from methyl and ethyl. In an even further aspect, $R^{11a}$ is hydrogen and $R^{11b}$ is ethyl. In a still further aspect, $R^{11a}$ is hydrogen and $R^{11b}$ is methyl.

c. $R^{14A}$ and $R^{14B}$ Groups

In one aspect, each of $R^{14a}$ and $R^{14b}$, when present, is independently selected from hydrogen, C1-C4 alkyl, and amine protecting group. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. Thus, in a further aspect, each of $R^{14a}$ and $R^{14b}$, when present, is independently selected from hydrogen, methyl, ethyl, n-propyl, iso-propyl, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. In a still further aspect, each of $R^{14a}$ and $R^{14b}$, when present, is independently selected from hydrogen, methyl, ethyl, and t-butyloxycarbonyl. In yet a further aspect, each of $R^{14a}$ and $R^{14b}$, when present, is independently selected from hydrogen and t-butyloxycarbonyl.

In a further aspect, each of $R^{14a}$ and $R^{14b}$, when present, is independently selected from hydrogen and C1-C4 alkyl. In a still further aspect, each of $R^{14a}$ and $R^{14b}$, when present, is independently selected from hydrogen, methyl, ethyl, n-propyl, and iso-propyl. In yet a further aspect, each of $R^{14a}$ and $R^{14b}$, when present, is independently selected from hydrogen, methyl, and ethyl. In an even further aspect, each of $R^{14a}$ and $R^{14b}$, when present, is independently selected from hydrogen and ethyl. In a still further aspect, each of $R^{14a}$ and $R^{14b}$, when present, is independently selected from hydrogen and methyl. In yet a further aspect, each of $R^{14a}$ and $R^{14b}$, when present, is hydrogen.

In a further aspect, each of $R^{14a}$ and $R^{14b}$, when present, is independently selected from C1-C4 alkyl. In a still further aspect, each of $R^{14a}$ and $R^{14b}$, when present, is independently selected from methyl, ethyl, n-propyl, and iso-propyl. In yet a further aspect, each of $R^{14a}$ and $R^{14b}$, when present, is independently selected from methyl and ethyl. In an even further aspect, each of $R^{14a}$ and $R^{14b}$, when present, is ethyl. In a still further aspect, each of $R^{14a}$ and $R^{14b}$, when present, is methyl.

In a further aspect, $R^{14a}$ is hydrogen and $R^{14b}$ is C1-C4 alkyl. In a still further aspect, $R^{14a}$ is hydrogen and $R^{14b}$ is selected from methyl, ethyl, n-propyl, and iso-propyl. In yet a further aspect, $R^{14a}$ is hydrogen and $R^{14b}$ is selected from methyl and ethyl. In an even further aspect, $R^{14a}$ is hydrogen and $R^{14b}$ is ethyl. In a still further aspect, $R^{14a}$ is hydrogen and $R^{14b}$ is methyl.

d. $R^{16}$ Groups

In one aspect, $R^{16}$, when present, is hydroxy protecting group. Examples of hydroxy protecting groups include, but are not limited, to acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, tetrahydrfuran, trityl, silyl ethers, methyl ethers, and triflate. Thus, in various aspects, $R^{16}$, when present, is triflate.

e. $R^{30A}$, $R^{30B}$, $R^{30C}$, $R^{30D}$, and $R^{30E}$ Groups

In one aspect, each of $R^{30a}$, $R^{30b}$, $R^{30c}$, $R^{3d}$, and $R^{30e}$, when present, is independently selected from hydrogen, halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$, or wherein any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$.

In a further aspect, each of $R^{30a}$, $R^{30b}$, $R^{30c}$, $R^{30d}$, and $R^{30e}$, when present, is independently selected from hydrogen, halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, each of $R^{30a}$, $R^{30b}$, $R^{30c}$, $R^{30d}$, and $R^{30e}$, when present, is independently selected from hydrogen, halogen, —CN, —$NO_2$, C1-C4 alkyl, C1-C4 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, each of $R^{30a}$, $R^{30b}$, $R^{30c}$, $R^{30d}$, and $R^{30e}$, when present, is independently selected from hydrogen, halogen, —CN, —$NO_2$, methyl, ethyl, n-propyl, isopropyl, methoxy, ethoxy, n-propoxy, isopropoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, each of $R^{30a}$, $R^{30b}$, $R^{30c}$, $R^{30d}$, and $R^{30e}$, when present, is independently selected from hydrogen, halogen, —CN, —$NO_2$, methyl, ethyl, methoxy, ethoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, each of $R^{30a}$, $R^{30b}$, $R^{30c}$, $R^{30d}$, and $R^{30e}$, when present, is independently selected from hydrogen, halogen, —CN, —$NO_2$, methyl, methoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, each of $R^{30a}$, $R^{30b}$, $R^{30c}$, $R^{30d}$, and $R^{30e}$, when present, is hydrogen.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$, are optionally covalently bonded and, together with the intermediate atoms, comprise a 5- to 6-membered cycle or heterocycle having 0, 1, or 2 heteroatoms and monosubstituted with a group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and unsubstituted.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle monosubstituted with a group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered unsubstituted cycle.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered cycle substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered cycle substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered cycle substituted with 0 or 1 group selected from halogen, —CN, —$NO_2$, C1-C8 alkyl, C1-C8 alkoxy, —C(═O)$R^{10}$, —C(═O)$OR^{11}$, C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered cycle monosubstituted with a group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered unsubstituted cycle.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered cycle substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered cycle substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered cycle substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{3a}$, $R^{30b}$, $R^{30c}$, $R^{30d}$, and $R^{30e}$ are optionally covalently bonded and, together with the intermediate atoms, comprise a 6-membered cycle monosubstituted with a group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered unsubstituted cycle.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered heterocycle having 0, 1, or 2 heteroatoms and substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered heterocycle having 0, 1, or 2 heteroatoms and substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered heterocycle having 0, 1, or 2 heteroatoms and monosubstituted with a group selected from halogen, —CN, —$NO_2$, C1-C8 alkyl, C1-C8 alkoxy, —C(═O)$R^{10}$, —C(═O)$OR^{1}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5- to 6-membered heterocycle having 0, 1, or 2 heteroatoms and unsubstituted.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered heterocycle having 0, 1, or 2 heteroatoms and substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered heterocycle having 0, 1, or 2 heteroatoms and substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered heterocycle having 0, 1, or 2 heteroatoms and monosubstituted with a group selected from halogen, —CN, —$NO_2$, C1-C8 alkyl, C1-C8 alkoxy, —C(═O)$R^{10}$, —C(═O)$OR^{11}$, C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 5-membered heterocycle having 0, 1, or 2 heteroatoms and unsubstituted.

In a further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered heterocycle having 0, 1, or 2 heteroatoms and substituted with 0, 1, or 2 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered heterocycle having 0, 1, or 2 heteroatoms and substituted with 0 or 1 group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered heterocycle having 0, 1, or 2 heteroatoms and monosubstituted with a group selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, any adjacent two of $R^{30a}$, $R^{30b}$, $R^{30c}$, $R^{30d}$, and $R^{30e}$ are optionally covalently bonded and, together with the intermediate atoms, comprise a 6-membered heterocycle having 0, 1, or 2 heteroatoms and unsubstituted.

f. $AR^1$ Groups

In one aspect, $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; or wherein $Ar^1$ is a structure represented by a formula:

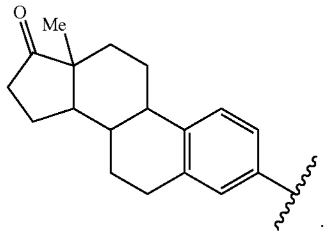 [SMILES: *c1ccc2c(c1)CCC1C2CCC2(C)C(=O)CCC12]

Examples of aryl and heteroaryl groups include, but are not limited to, phenyl, naphthyl, furanyl, pyridinyl, pyrazinyl, pyrrolyl, imidazolyl, pyrazolyl, oxazolyl, thiophenyl, benzimidazolyl, purinyl, indolyl, quinolinyl, isoquinolinyl, phthalazinyl, and quinazolinyl. Additional examples of aryl and heteroaryl groups are disclosed elsewhere herein. In a further aspect, $Ar^1$ is selected from aryl and heteroaryl and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; or wherein $Ar^1$ is a structure represented by a formula:

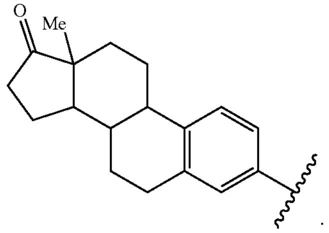 [SMILES: *c1ccc2c(c1)CCC1C2CCC2(C)C(=O)CCC12]

In one aspect, $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a further aspect, $Ar^1$ is selected from aryl and heteroaryl and substituted with 0-6 groups independently selected from halogen, —CN, —$NO_2$, C1-C4 alkyl, C1-C4 alkoxy, —O—(C1-C4 alkyl)-$CO_2$—(C1-C4 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a still further aspect, $Ar^1$ is selected from aryl and heteroaryl and substituted with 0-6 groups independently selected from halogen, —CN, —$NO_2$, methyl, ethyl, n-propyl, isopropyl, methoxy, ethoxy, n-propoxy, isopropoxy, —$OCH_2CO_2CH_3$, —$OCH_2CH_2CO_2CH_2CH_3$, —$OCH_2CO_2CH(CH_3)_2$, —$OCH_2CO_2CH_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In yet a further aspect, $Ar^1$ is selected from aryl and heteroaryl and substituted with 0-6 groups independently selected from halogen, —CN, —$NO_2$, methyl, ethyl, methoxy, ethoxy, —$OCH_2CO_2CH_3$, —$OCH_2CH_2CO_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In an even further aspect, $Ar^1$ is selected from aryl and heteroaryl and substituted with 0-6 groups independently selected from halogen, —CN, —$NO_2$, methyl, methoxy, —$OCH_2CO_2CH_3$, —$OCH_2CH_2CO_2CH_2CH_3$, —$OCH_2CO_2CH(CH_3)_2$, —$OCH_2CO_2CH_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$.

In a further aspect, $Ar^1$ is selected from aryl and heteroaryl and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a further aspect, $Ar^1$ is selected from aryl and heteroaryl and substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is selected from aryl and heteroaryl and substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is selected from aryl and heteroaryl and monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, $Ar^1$ is selected from aryl and heteroaryl and is unsubstituted.

In various aspects, $Ar^1$ is selected from aryl and heteroaryl and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a further aspect, $Ar^1$ is selected from aryl and heteroaryl and substituted with 0, 1, 2, or 3 groups independently selected from halogen, —CN, —$NO_2$, C1-C4 alkyl, C1-C4 alkoxy, —O—(C1-C4 alkyl)-C02-(C1-C4 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a still further aspect, $Ar^1$ is selected from aryl and heteroaryl and substituted with 0, 1, 2, or 3 groups independently selected from halogen, —CN, —$NO_2$, methyl, ethyl, n-propyl, isopropyl, methoxy, ethoxy, n-propoxy, isopropoxy, —$OCH_2CO_2CH_3$, —$OCH_2CH_2CO_2CH_2CH_3$, —$OCH_2CO_2CH(CH_3)_2$, —$OCH_2CO_2CH_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In yet a further aspect, $Ar^1$ is selected from aryl and heteroaryl and substituted with 0, 1, 2, or 3 groups independently selected from halogen, —CN, —$NO_2$, methyl, ethyl, methoxy, ethoxy, —$OCH_2CO_2CH_3$, —$OCH_2CH_2CO_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In an even further aspect, $Ar^1$ is selected from aryl and heteroaryl and substituted with 0, 1, 2, or 3 groups independently selected from halogen, —CN, —$NO_2$, methyl, methoxy, —$OCH_2CO_2CH_3$, —$OCH_2CH_2CO_2CH_2CH_3$, —$OCH_2CO_2CH(CH_3)_2$, —$OCH_2CO_2CH_2CH_2CH_3$, —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$.

In a further aspect, $Ar^1$ is aryl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is aryl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is aryl substituted with 0 or 1 group selected from halogen, —CN, —$NO_2$, C1-C8 alkyl, C1-C8 alkoxy, —C(═O)$R^{10}$, —C(═O)$OR^{11}$, C(═O)$NR^{12a}R^{12b}$, $Ar^2$, and —$CH_2CR^{13}(NR^{14a}R^{14b})CO_2R^{15}$. In an even further aspect, $Ar^1$ is aryl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is unsubstituted aryl.

In a further aspect, $Ar^1$ is aryl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a still further aspect, $Ar^1$ is aryl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In yet a further aspect, $Ar^1$ is aryl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In an even further aspect, $Ar^1$ is aryl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$.

In a further aspect, $Ar^1$ is phenyl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is phenyl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is phenyl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, $Ar^1$ is phenyl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is unsubstituted phenyl.

In a further aspect, $Ar^1$ is phenyl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In a still further aspect, $Ar^1$ is phenyl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In yet a further aspect, $Ar^1$ is phenyl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$. In an even further aspect, $Ar^1$ is phenyl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$.

In a further aspect, $Ar^1$ is naphthyl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and -$CH_2CR^{13}(NR^{14a}R^{14b})CO_2R^{15}$. In a still further aspect, $Ar^1$ is naphthyl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{75}$. In yet a further aspect, $Ar^1$ is naphthyl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{4a}R^{14b})CO_2R^{15}$. In an even further aspect, $Ar^1$ is naphthyl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is unsubstituted naphthyl.

In a further aspect, $Ar^1$ is heteroaryl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is heteroaryl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is heteroaryl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, $Ar^1$ is heteroaryl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is unsubstituted heteroaryl.

In a further aspect, $Ar^1$ is pyridinyl substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is pyridinyl substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is pyridinyl substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, $Ar^1$ is pyridinyl monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is unsubstituted pyridinyl.

In a further aspect, $Ar^1$ is selected from 5-membered aryl, 6-membered aryl, 5-membered heteroaryl, and 6-membered heteroaryl, and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a further aspect, $Ar^1$ is selected from 5-membered aryl, 6-membered aryl, 5-membered heteroaryl, and 6-membered heteroaryl, and substituted with 0, 1, or 2 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In a still further aspect, $Ar^1$ is selected from 5-membered aryl, 6-membered aryl, 5-membered heteroaryl, and 6-membered heteroaryl, and substituted with 0 or 1 group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In yet a further aspect, $Ar^1$ is selected from 5-membered aryl, 6-membered aryl, 5-membered heteroaryl, and 6-membered heteroaryl, and monosubstituted with a group selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$. In an even further aspect, $Ar^1$ is selected from 5-membered aryl, 6-membered aryl, 5-membered heteroaryl, and 6-membered heteroaryl, and unsubstituted.

In a further aspect, Ar is a structure represented by a formula:

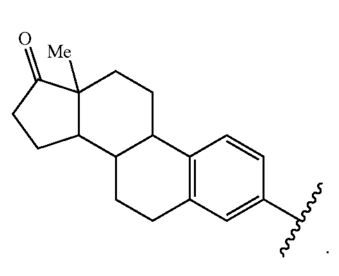 [SMILES: *c1ccc2c(c1)CCC1C2CCC2(C)C(=O)CCC12]

g. $AR^2$ Groups

In one aspect, $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a further aspect, $Ar^2$, when present, is selected from aryl and heteroaryl and substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is selected from aryl and heteroaryl and substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is selected from aryl and heteroaryl and monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is selected from aryl and heteroaryl and unsubstituted.

In one aspect, $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino. In a further aspect, $Ar^2$, when present, is selected from aryl and heteroaryl and substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is selected from aryl and heteroaryl and substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is selected from aryl and heteroaryl and monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino.

In a further aspect, $Ar^2$, when present, is aryl substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is aryl substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is aryl substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is aryl monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is unsubstituted aryl.

In a further aspect, $Ar^2$, when present, is phenyl substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is phenyl substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is phenyl substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is phenyl monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is unsubstituted phenyl.

In a further aspect, $Ar^2$, when present, is naphthyl substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is naphthyl substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is naphthyl substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is naphthyl monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is unsubstituted naphthyl.

In a further aspect, $Ar^2$, when present, is pyridinyl substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is pyridinyl substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is pyridinyl substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is pyridinyl monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is unsubstituted pyridinyl.

In a further aspect, $Ar^2$, when present, is selected from 5-membered aryl, 6-membered aryl, 5-membered heteroaryl, and 6-membered heteroaryl, and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a further aspect, $Ar^2$, when present, is selected from 5-membered aryl, 6-membered aryl, 5-membered heteroaryl, and 6-membered heteroaryl, and substituted with 0, 1, or 2 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^2$, when present, is selected from 5-membered aryl, 6-membered aryl, 5-membered heteroaryl, and 6-membered heteroaryl, and substituted with 0 or 1 group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^2$, when present, is selected from 5-membered aryl, 6-membered aryl, 5-membered heteroaryl, and 6-membered heteroaryl, and monosubstituted with a group selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^2$, when present, is selected from 5-membered aryl, 6-membered aryl, 5-membered heteroaryl, and 6-membered heteroaryl, and unsubstituted.

2. Example Structures

In one aspect, a compound can be present as:

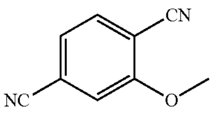

,

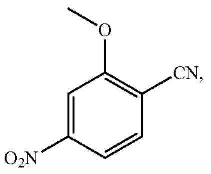

-continued

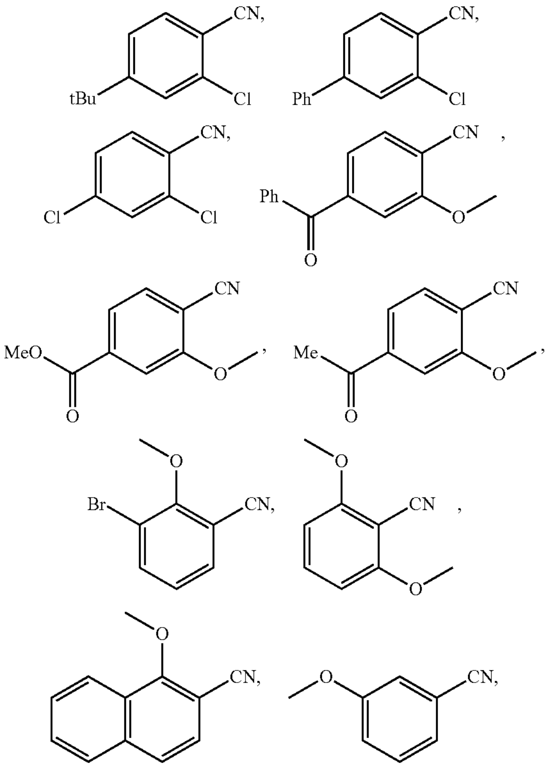

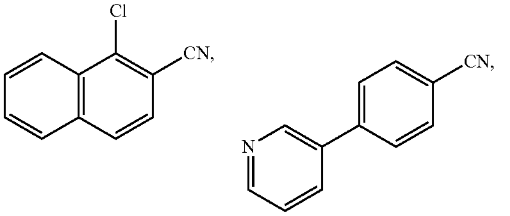

and

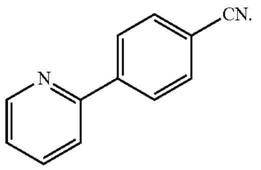

In one aspect, a compound can be present as:

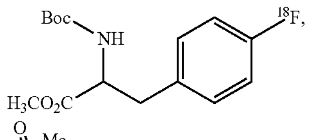

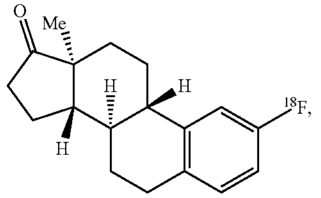

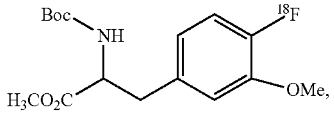

-continued
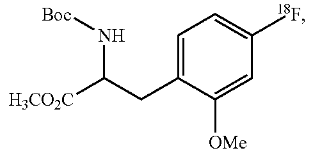
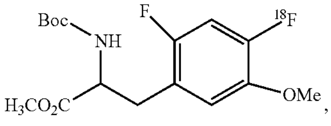
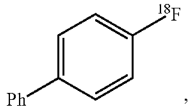
and
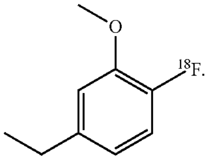
In one aspect, a compound can be present as:
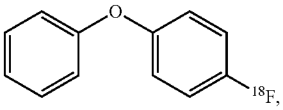
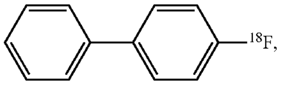
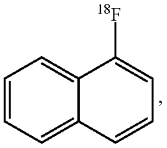
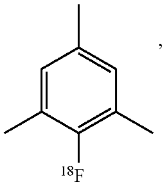
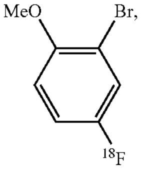
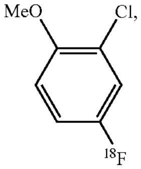
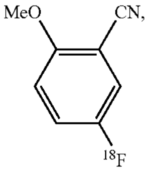
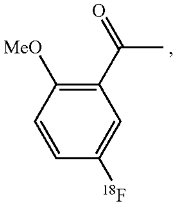
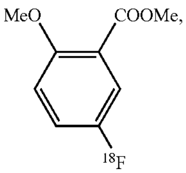
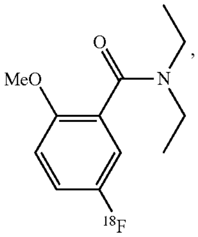
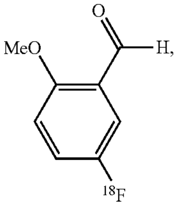
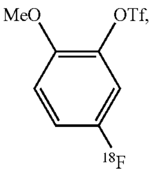
-continued
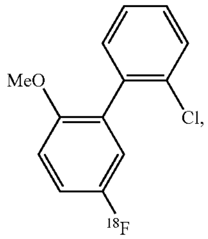
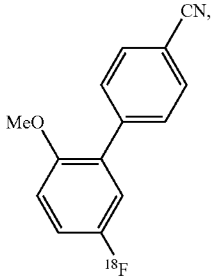
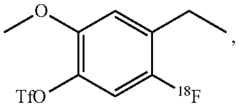
and
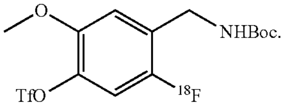
In one aspect, a compound can be present as:
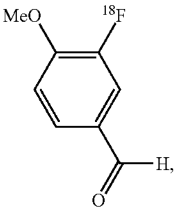
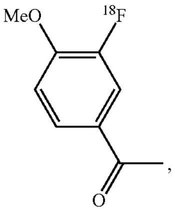
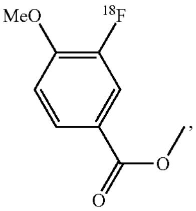
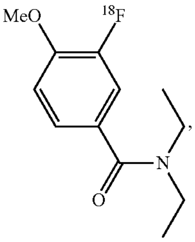
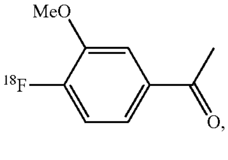
and
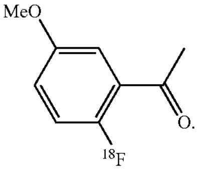
In one aspect, a compound can be present as:
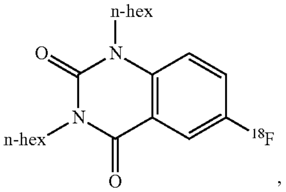
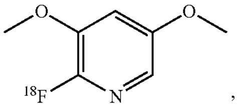

-continued
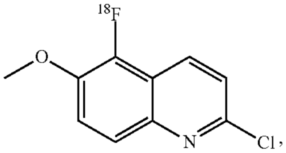
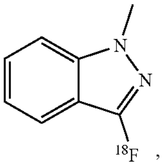
, and
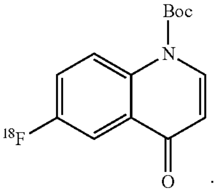
.
In one aspect, a compound can be present as:
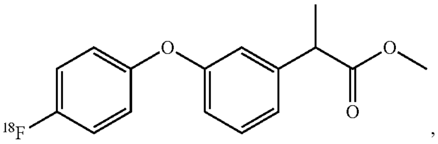
,
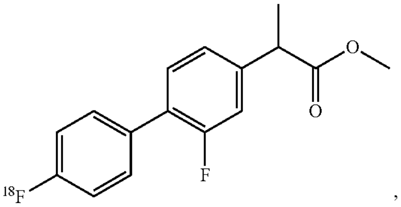
,
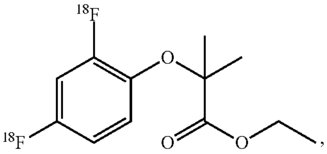
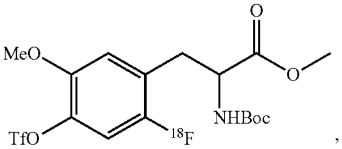
, and
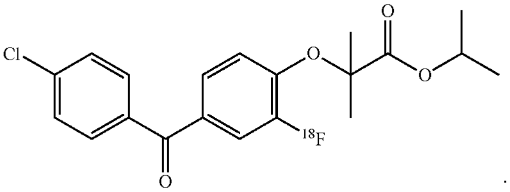
.
In one aspect, a compound can be present as:
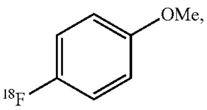
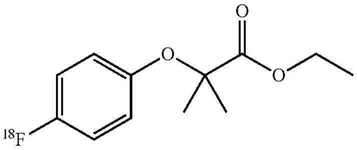
, and
-continued
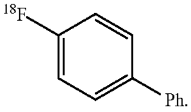
In one aspect, a compound can be present as:
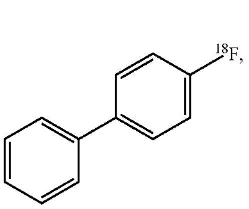
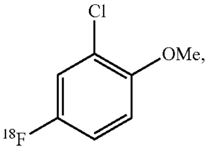
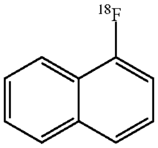
,
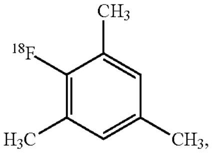
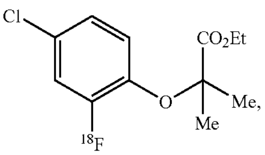
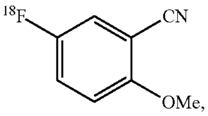
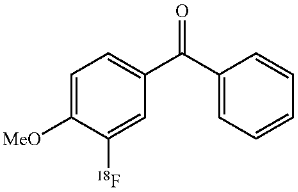
,
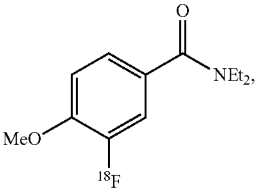
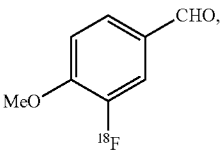
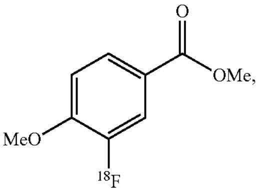
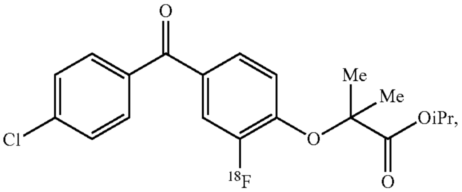
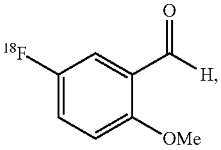
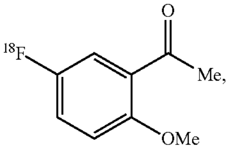

-continued
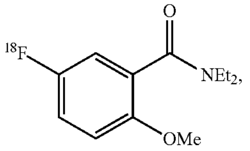
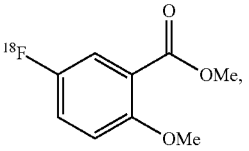
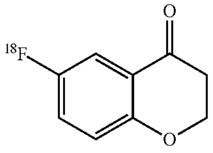,
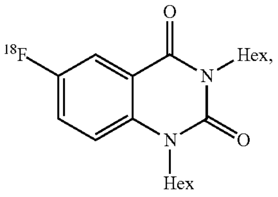
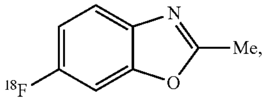
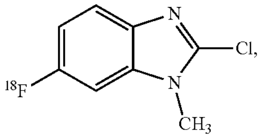
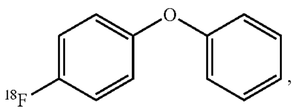,
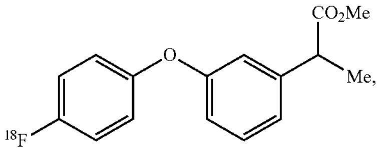 and
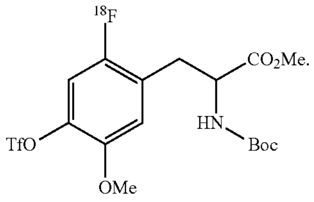
3. Prophetic Examples
The following compound examples are prophetic, and can be prepared using the synthesis methods described herein above and other general methods as needed as would be known to one skilled in the art. Thus, in one aspect, a compound can be:
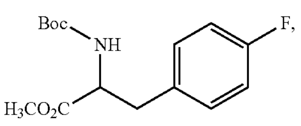
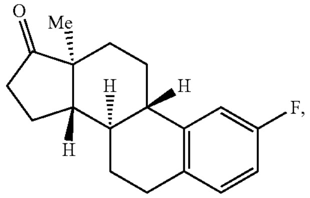
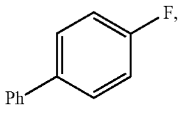 and
-continued
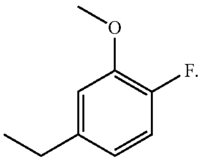
In one aspect, a compound can be:
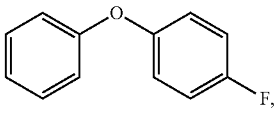
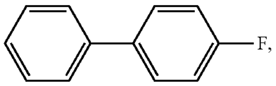
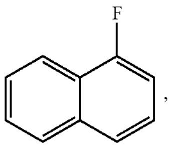,
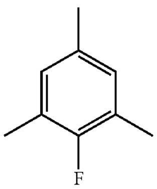,
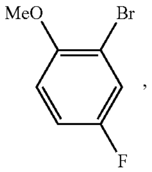,
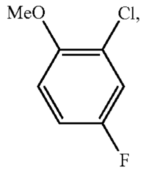
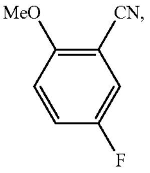
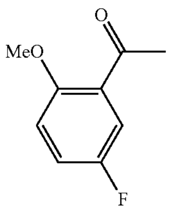,
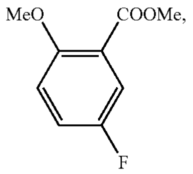
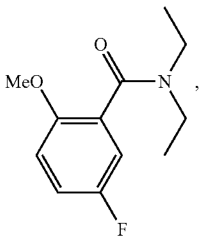
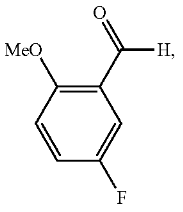
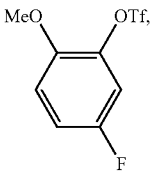
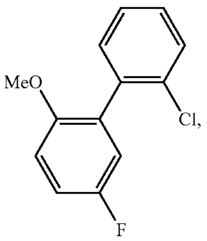
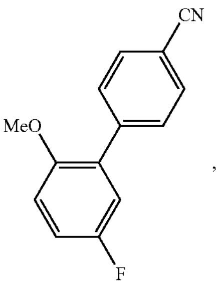,
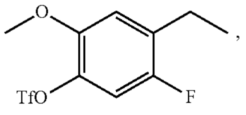, or
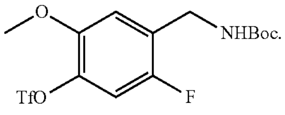

In one aspect, a compound can be:
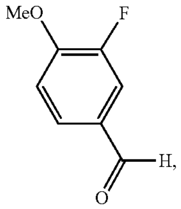
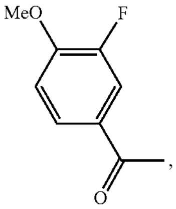
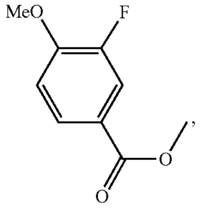
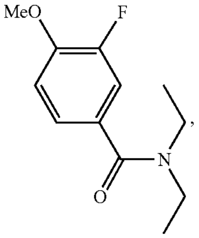
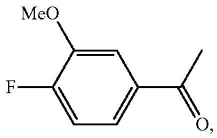
or
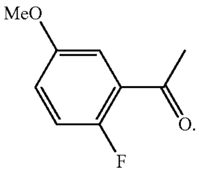
In one aspect, a compound can be:
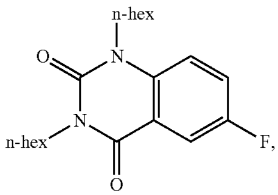
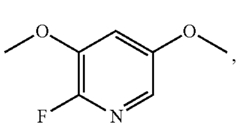
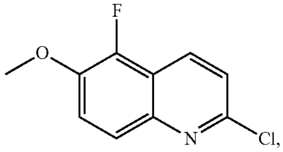
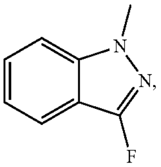
or
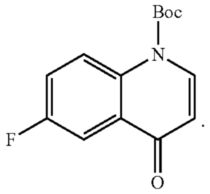
In one aspect, a compound can be:
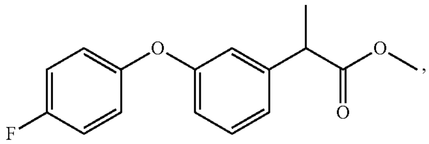
-continued
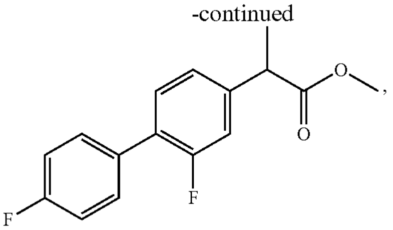
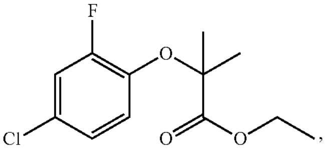
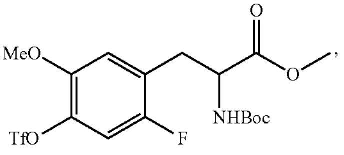
or
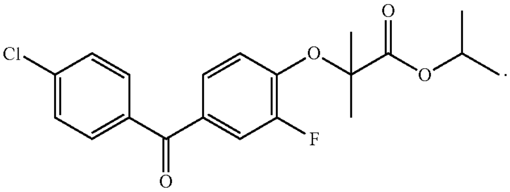
In one aspect, a compound can be:
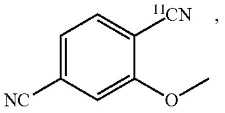
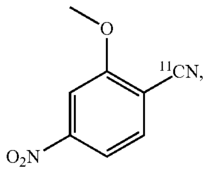
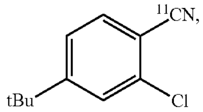
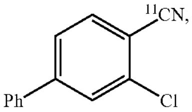
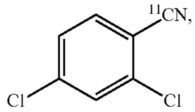
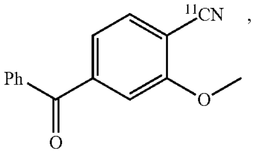
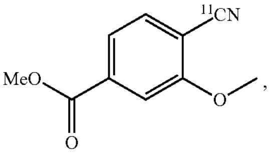
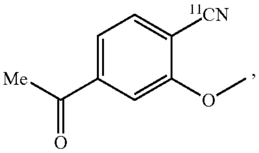
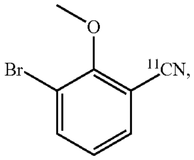
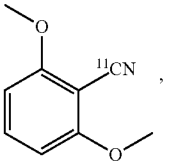
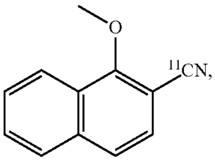

-continued

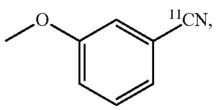
,
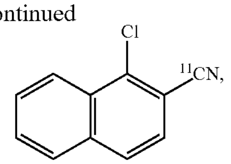
,
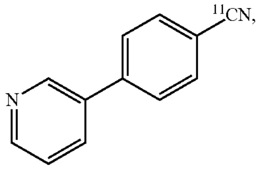
, or
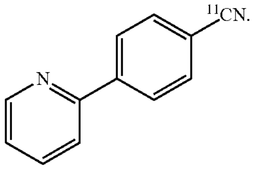
.

C. Arene Compounds

In one aspect, disclosed are arenes useful in the disclosed methods. It is contemplated that each disclosed derivative can be optionally further substituted. It is also contemplated that any one or more derivative can be optionally omitted from the invention. It is understood that a disclosed compound can be provided by the disclosed methods.

1. Structure

In one aspect, disclosed are arenes having a structure represented by a formula:

$Ar^1$-E, wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}$($NR^{14a}R^{14b}$)$CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

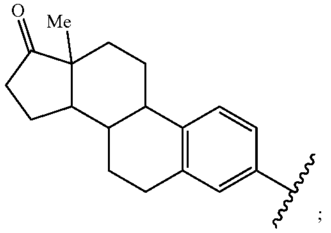 [SMILES: *c1ccc2c(c1)CCC1C2CCC2(C)C(=O)CCC12]
;

and wherein E is an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino.

In one aspect, disclosed are arenes having a structure represented by a formula:

$Ar^1$-E, wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}$($NR^{14a}R^{14b}$)$CO_2R^{15}$; wherein each of $R^{10}$, $R^{11}$, $R^{12a}R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

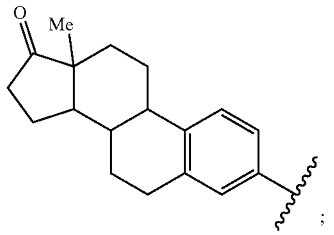 [SMILES: *c1ccc2c(c1)CCC1C2CCC2(C)C(=O)CCC12]
;

and wherein E is hydrogen or an electron donating group selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino.

In one aspect, disclosed are arenes having a structure represented by a formula:

$Ar^1$-E, wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

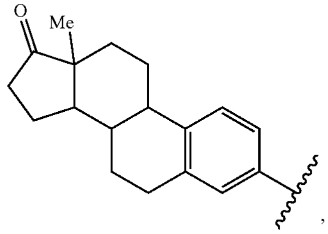

, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino.

Also disclosed are arenes having a structure represented by a formula:

$Ar^1$—H, wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a

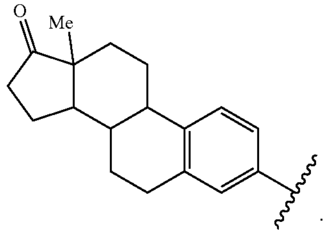 [SMILES: *c1ccc2c(c1)CCC1C2CCC2(C)C(=O)CCC12]

.

In one aspect, disclosed are arenes having a structure represented by a formula:

$Ar^1$—X', wherein X' is halogen and wherein X' does not contain a radioisotope; and wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

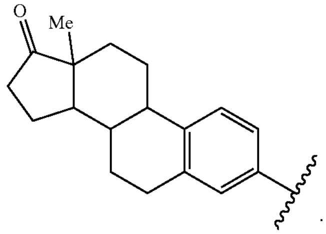 [SMILES: *c1ccc2c(c1)CCC1C2CCC2(C)C(=O)CCC12]

.

In a further aspect, the arene has a structure represented by a formula:

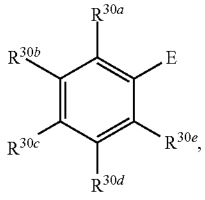

wherein each of $R^{30a}$, $R^{30b}$, $R^{30c}$, $R^{30d}$, and $R^{30e}$ is independently selected from hydrogen, halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$, or wherein any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$.

In a further aspect, the arene has a structure represented by a formula selected from:

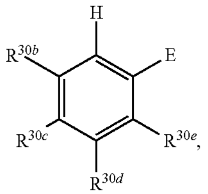
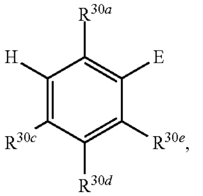
and
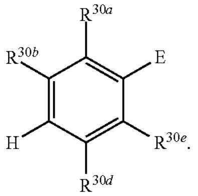

In a further aspect, the arene has a structure represented by a formula:

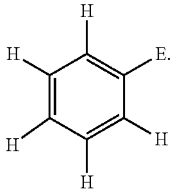

In a further aspect, the arene has a structure represented by a formula selected from:

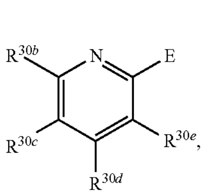
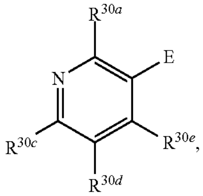
and
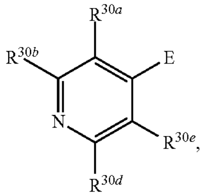

wherein each of $R^{30a}$, $R^{30b}$, $R^{30c}$, $R^{30d}$, and $R^{30e}$, when present, is independently selected from hydrogen, halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$, or wherein any adjacent two of $R^{30a}$, $R^{30b}$, $R^{30c}$, $R^{30d}$, and $R^{30e}$ are optionally covalently bonded and, together with the intermediate atoms, comprise a 5- to 6-membered cycle or heterocycle having 0, 1, or 2 heteroatoms and substituted with 0, 1, 2, or 3 groups independently selected from halogen, —CN, —$NO_2$, C1-C8 alkyl, C1-C8 alkoxy, —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$.

In a further aspect, the arene has a structure represented by a formula selected from:

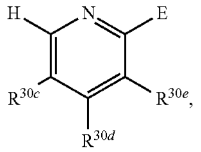
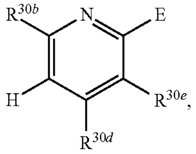
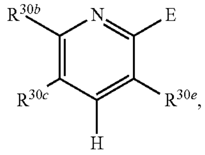
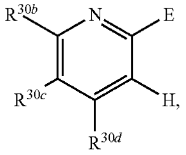
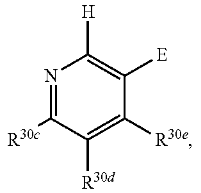
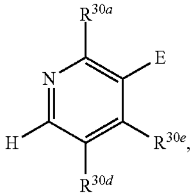
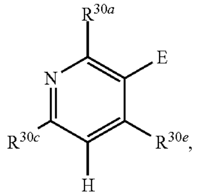
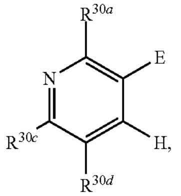
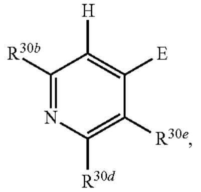
and
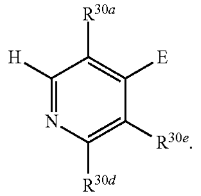

In a further aspect, the arene has a structure represented by a formula selected from:

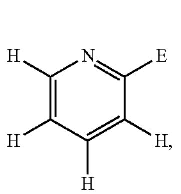
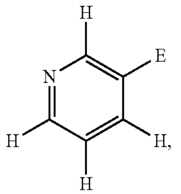
and
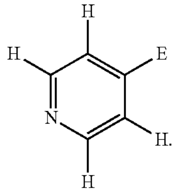

In a further aspect, the arene has a structure represented by a formula:

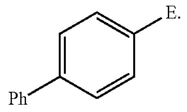

In a further aspect, the arene has a structure represented by a formula:

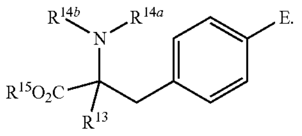

In a further aspect, the arene has a structure represented by a formula:

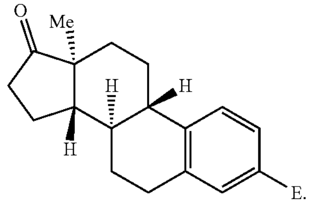

a. E Groups

In one aspect, E is an electron donating group. Exemplary electron donating groups are well known by those skilled in the art and include, but are not limited to, alkyl, alcohol, thioalcohol, alkoxy, thioalkoxy, silyloxy, amine, ester, amide, and aryl groups. Thus, in one aspect, E is an electron donating group selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$.

In one aspect, E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, —OC(═O)$NHR^{20}$. In a further aspect, E is hydrogen.

In a further aspect, the electron donating group is selected from —$OR^{20}$, —OC(═O)$R^{20}$, and —OC(═O)$OR^{20}$. In a still further aspect, the electron donating group is selected from —$OR^{20}$ and —OC(═O)$R^{20}$. In yet a further aspect, the electron donating group is selected from —$OR^{20}$ and —OC(═O)$OR^{20}$. In an even further aspect, the electron donating group is selected from —OC(═O)$R^{20}$ and —OC(═O)$OR^{20}$. In a still further aspect, the electron donating group is —$OR^{20}$. In yet a further aspect, the electron donating group is —OC(═O)$R^{20}$. In an even further aspect, the electron donating group is —OC(═O)$OR^{20}$.

In a further aspect, the electron donating group is selected from —$SO_3R^{20}$, —$SR^{20}$, and —OC(═O)$SR^{20}$. In a still further aspect, the electron donating group is selected from —$SO_3R^{20}$ and —$SR^{20}$. In yet a further aspect, the electron donating group is selected from —$SO_3R^{20}$ and —OC(═O)$SR^{20}$. In an even further aspect, the electron donating group is selected from —$SR^{20}$ and —OC(═O)$SR^{20}$. In a still further aspect, the electron donating group is —$SO_3R^{20}$. In yet a further aspect, the electron donating group is —$SR^{20}$. In an even further aspect, the electron donating group is —OC(═O)$SR^{20}$.

In a further aspect, the electron donating group is selected from —$NR^{21a}R^{21b}$ and —OC(═O)$NHR^{20}$. In a still further aspect, the electron donating group is —$NR^{21a}R^{21b}$. In yet a further aspect, the electron donating group is —OC(═O)$NHR^{20}$.

In a further aspect, the electron donating group is selected from —OH, —SH, —$NH_2$, C1-C8 alkyl, C1-C8 alkoxy, C1-C8 thioalkoxy, C1-C8 silyloxy, C1-C8 alkylamino, (C1-C8)(C1-C8) dialkylamino, —OC(═O)$R^6$, —NHC(═O)$R^7$, —$OAr^2$, and $Ar^2$. In a still further aspect, the electron donating group is selected from —OH, —SH, —$NH_2$, C1-C8 alkyl, C1-C8 alkoxy, C1-C4 thioalkoxy, C1-C4 silyloxy, C1-C4 alkylamino, (C1-C4)(C1-C4) dialkylamino, —OC(═O)$R^6$, —NHC(═O)$R^7$, —$OAr^2$, and $Ar^2$.

In a further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, —NHC(═O)$R^7$, and $Ar^2$. In a still further aspect, the electron donating group is selected from —OH, —SH, —$NH_2$, C1-C8 alkyl, C1-C8 alkoxy, C1-C4 thioalkoxy, C1-C4 alkylamino, (C1-C4)(C1-C4) dialkylamino, —OC(═O)$R^6$, —NHC(═O)$R^7$, and $Ar^2$.

In a further aspect, the electron donating group is selected from —OH, —SH, —$NH_2$, C1-C8 alkyl, C1-C8 alkoxy, C1-C8 thioalkoxy, C1-C8 alkylamino, (C1-C8)(C1-C8) dialkylamino, —OC(═O)$R^6$, and —NHC(═O)$R^7$. In a still further aspect, the electron donating group is selected from —OH, —SH, —$NH_2$, C1-C8 alkyl, C1-C4 alkoxy, C1-C4 thioalkoxy, C1-C4 alkylamino, (C1-C4)(C1-C4) dialkylamino, —OC(═O)$R^6$, and —NHC(═O)$R^7$. In yet a further aspect, the electron donating group is selected from —OH, —SH, —$NH_2$, methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, —$N(CH(CH_3)_2)_2$, —OC(═O)$R^6$, and —NHC(═O)$R^7$. In an even further aspect, the electron donating group is selected from —OH, —SH, —$NH_2$, methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, —$N(CH_2CH_3)_2$, —OC(═O)$R^6$, and —NHC(═O)$R^7$. In a still further aspect, the electron donating group is selected from —OH, —SH, —$NH_2$, methyl, —$OCH_3$, —$SCH_3$, —$NHCH_3$, —$N(CH_3)_2$, —OC(═O)$R^6$, and —NHC(═O)$R^7$.

In a further aspect, the electron donating group is a C1-C8 silyloxy. In a still further aspect, the electron donating group is selected from trimethylsilyloxy, triisopropylsilyloxy, and tert-butyldimethylsilyloxy. In yet a further aspect, the electron donating group is selected from trimethylsilyloxy and triisopropylsilyloxy. In an even further aspect, the electron donating group is tert-butyldimethylsilyloxy. In a still further aspect, the electron donating group is triisopropylsilyloxy. In yet a further aspect, the electron donating group is trimethylsilyloxy.

In a further aspect, the electron donating group is selected from —OH, —SH, —$NH_2$, C1-C8 alkyl, C1-C8 alkoxy, C1-C8 thioalkoxy, C1-C8 alkylamino, and (C1-C8)(C1-C8) dialkylamino. In a still further aspect, the electron donating group is selected from —OH, —SH, —$NH_2$, C1-C8 alkyl, C1-C4 alkoxy, C1-C4 thioalkoxy, C1-C4 alkylamino, and (C1-C4)(C1-C4) dialkylamino. In yet a further aspect, the electron donating group is selected from —OH, —SH, —$NH_2$, methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, the electron donating group is selected from —OH, —SH, —$NH_2$, methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, and —$N(CH_2CH_3)_2$. In a still further aspect, the electron donating group is selected from —OH, —SH, —$NH_2$, methyl, —$OCH_3$, —$SCH_3$, —$NHCH_3$, and —$N(CH_3)_2$.

In a further aspect, the electron donating group is selected from —OH, —SH, —$NH_2$, —OC(═O)$R^6$, —NHC(═O)$R^7$, —$OAr^2$, and $Ar^2$. In a still further aspect, the electron donating group is selected from —OC(═O)$R^6$, —NHC(═O)$R^7$, —$OAr^2$, and $Ar^2$. In yet a further aspect, the electron donating group is —$OAr^2$.

In a further aspect, the electron donating group is selected from —OH, —SH, —$NH_2$, —OC(═O)$R^6$, —NHC(═O)$R^7$, and $Ar^2$. In a still further aspect, the electron donating group is selected from —OC(═O)$R^6$, —NHC(═O)$R^7$, and $Ar^2$. In yet a further aspect, the electron donating group is selected from —OC(═O)$R^6$ and —NHC(═O)$R^7$. In an even further aspect, the electron donating group is —OC(═O)$R^6$. In a still further aspect, the electron donating group is —NHC(═O)$R^7$. In yet a further aspect, the electron donating group is $Ar^2$.

In a further aspect, the electron donating group is selected from C1-C8 alkyl, C1-C8 alkoxy, C1-C8 thioalkoxy, C1-C8 alkylamino, and (C1-C8)(C1-C8) dialkylamino. In a still further aspect, the electron donating group is selected from C1-C8 alkyl, C1-C4 alkoxy, C1-C4 thioalkoxy, C1-C4 alkylamino, and (C1-C4)(C1-C4) dialkylamino. In yet a further aspect, the electron donating group is selected from methyl, ethyl, n-propyl, iso-propyl, —$OCH_3$, —$OCH_2CH_3$, —$OCH_2CH_2CH_3$, —$OCH(CH_3)_2$, —$SCH_3$, —$SCH_2CH_3$, —$SCH_2CH_2CH_3$, —$SCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In an even further aspect, the electron donating group is selected from methyl, ethyl, —$OCH_3$, —$OCH_2CH_3$, —$SCH_3$, —$SCH_2CH_3$, —$NHCH_3$, —$NHCH_2CH_3$, —$N(CH_3)_2$, —$N(CH_3)(CH_2CH_3)$, and —$N(CH_2CH_3)_2$. In a still further aspect, the electron donating group is selected from methyl, —$OCH_3$, —$SCH_3$, —$NHCH_3$, and —$N(CH_3)_2$.

In a further aspect, the electron donating group is selected from —OH, —SH, and —$NH_2$. In a still further aspect, the electron donating group is selected from —OH and —SH. In yet a further aspect, the electron donating group is selected from —OH and —$NH_2$. In an even further aspect, the electron donating group is selected from —SH and —$NH_2$. In a still further aspect, the electron donating group is —OH. In yet a further aspect, the electron donating group is —SH. In an even further aspect, the electron donating group is $NH_2$.

In a further aspect, the electron donating group is —$OR^{20}$.

In a further aspect, the electron donating group is —$OCH_3$.

In a further aspect, E is hydrogen.

b. $R^{20}$, $R^{21A}$, and $R^{21B}$ Groups

In one aspect, each of $R^{20}$, $R^{21a}$, and $R^{21b}$, when present, is independently selected from hydrogen, C1-C8 alkyl, C1-C8 alkenyl, and $Ar^3$. In a further aspect, each of $R^{20}$, $R^{21a}$, and $R^{21b}$, when present, is independently selected from hydrogen, C1-C4 alkyl, C1-C4 alkenyl, and $Ar^3$. In a still further aspect, each of $R^{20}$, $R^{21a}$, and $R^{21b}$, when present, is hydrogen.

In a further aspect, each of $R^{20}$, $R^{21a}$, and $R^{21b}$, when present, is independently selected from hydrogen, C1-C8 alkyl, and C1-C8 alkenyl. In a still further aspect, each of $R^{20}$, $R^{21a}$, and $R^{21b}$, when present, is independently selected from hydrogen, C1-C4 alkyl, and C1-C4 alkenyl. In yet a further aspect, each of $R^{20}$, $R^{21a}$, and $R^{21b}$, when present, is independently selected from hydrogen, methyl, ethyl, n-propyl, isopropyl, ethenyl, n-propenyl, and isopropenyl. In an even further aspect, each of $R^{20}$, $R^{21a}$, and $R^{21b}$, when present, is independently selected from hydrogen, methyl, ethyl, and ethenyl. In a still further aspect, each of $R^{20}$, $R^{21a}$, and $R^{21b}$, when present, is independently selected from hydrogen and methyl.

In a further aspect, each of $R^{20}$, $R^{21a}$, and $R^{21b}$, when present, is independently selected from C1-C8 alkyl and C1-C8 alkenyl. In a still further aspect, each of $R^{20}$, $R^{21a}$, and $R^{21b}$, when present, is independently selected from C1-C4 alkyl and C1-C4 alkenyl. In yet a further aspect, each of $R^{20}$, $R^{21a}$, and $R^{21b}$, when present, is independently selected from methyl, ethyl, n-propyl, isopropyl, ethenyl, n-propenyl, and isopropenyl. In an even further aspect, each of $R^{20}$, $R^{21a}$, and $R^{21b}$, when present, is independently selected from methyl, ethyl, and ethenyl. In a still further aspect, each of $R^{20}$, $R^{21a}$, and $R^{21b}$, when present, is methyl.

In a further aspect, each of $R^{20}$, $R^{21a}$, and $R^{21b}$, when present, is independently selected from hydrogen and $Ar^3$. In a still further aspect, each of $R^{20}$, $R^{21a}$, and $R^{21b}$, when present, is $Ar^3$.

c. $AR^3$ Groups

In one aspect, $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a further aspect, $Ar^3$, when present, is selected from aryl and heteroaryl and substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is selected from aryl and heteroaryl and substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is selected from aryl and heteroaryl and monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is selected from aryl and heteroaryl and unsubstituted.

In a further aspect, $Ar^3$, when present, is aryl substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is aryl substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is aryl substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is aryl monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is unsubstituted aryl.

In a further aspect, $Ar^3$, when present, is phenyl substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is phenyl substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is phenyl substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is phenyl monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is unsubstituted phenyl.

In a further aspect, $Ar^3$, when present, is naphthyl substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is naphthyl substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is naphthyl substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is naphthyl monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is unsubstituted naphthyl.

In a further aspect, $Ar^3$, when present, is pyridinyl substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is pyridinyl substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is pyridinyl substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is pyridinyl monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is unsubstituted pyridinyl.

In a further aspect, $Ar^3$, when present, is selected from 5-membered aryl, 6-membered aryl, 5-membered heteroaryl, and 6-membered heteroaryl, and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a further aspect, $Ar^3$, when present, is selected from 5-membered aryl, 6-membered aryl, 5-membered heteroaryl, and 6-membered heteroaryl, and substituted with 0, 1, or 2 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In yet a further aspect, $Ar^3$, when present, is selected from 5-membered aryl, 6-membered aryl, 5-membered heteroaryl, and 6-membered heteroaryl, and substituted with 0 or 1 group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In an even further aspect, $Ar^3$, when present, is selected from 5-membered aryl, 6-membered aryl, 5-membered heteroaryl, and 6-membered heteroaryl, and monosubstituted with a group selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino. In a still further aspect, $Ar^3$, when present, is selected from 5-membered aryl, 6-membered aryl, 5-membered heteroaryl, and 6-membered heteroaryl, and unsubstituted.

2. Example Arene Structures

In one aspect, an arene can be present as:

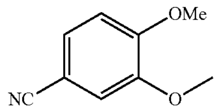
,
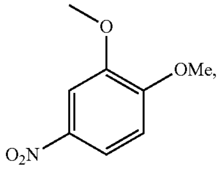
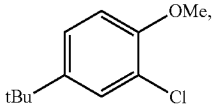
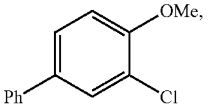
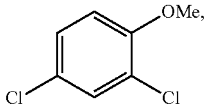
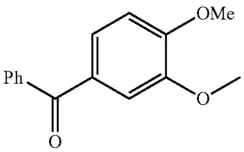
,
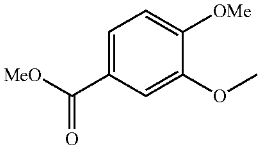
,
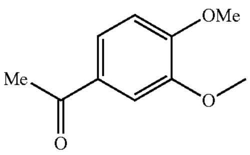
,
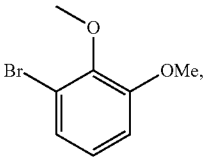
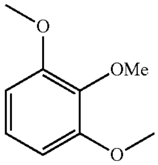
,
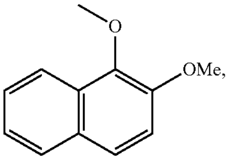
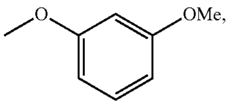
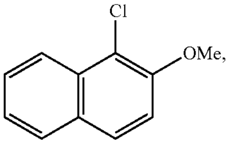
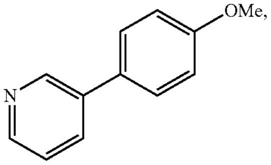
and
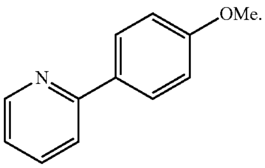

In one aspect, an arene can be present as:

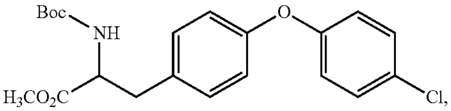
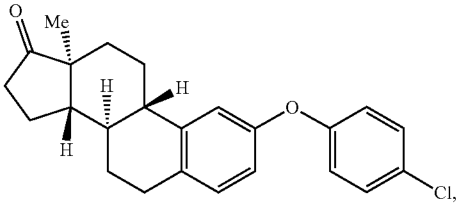
and
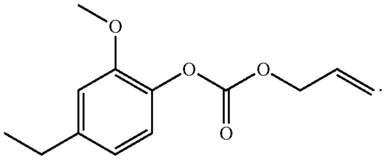

In one aspect, an arene can be present as:

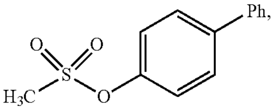
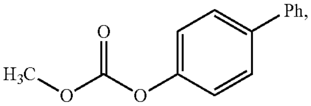
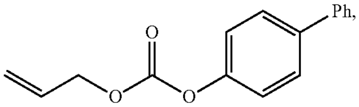
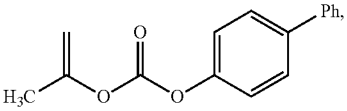
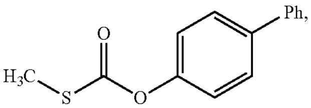
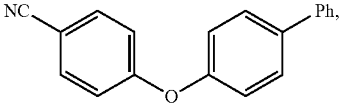
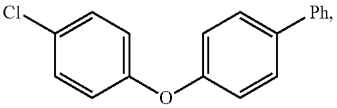
and
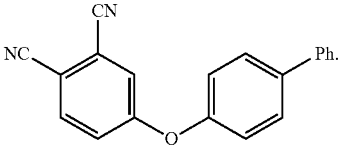

In one aspect, an arene can be present as:

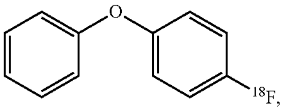

-continued
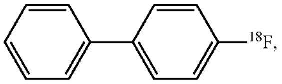
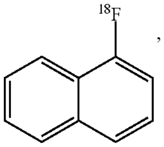
,
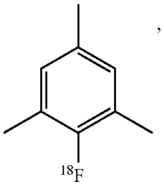
,
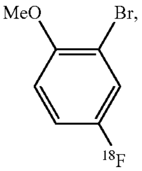
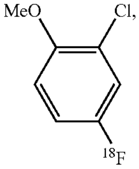
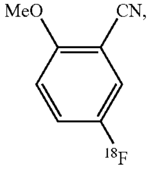
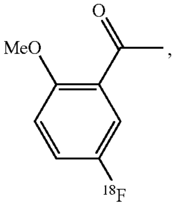
,
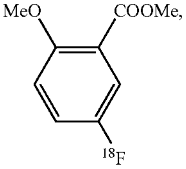
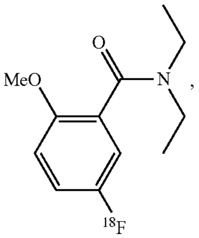
,
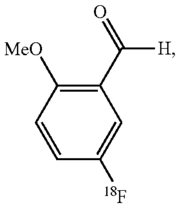
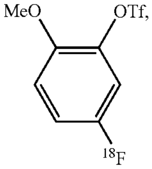
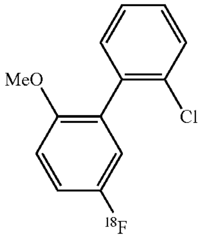
,
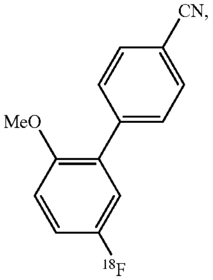
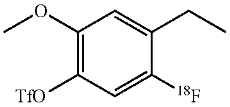
, and
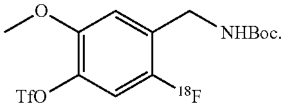
In one aspect, a compound can be present as:
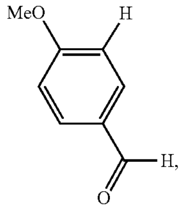
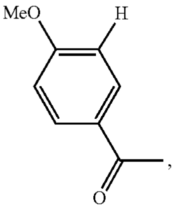
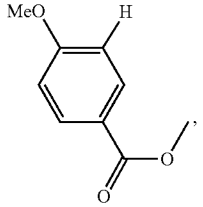
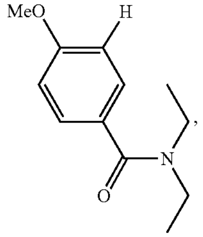
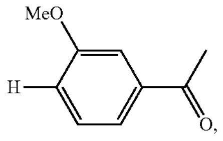
and
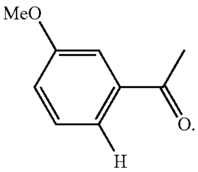
In one aspect, a compound can be present as:
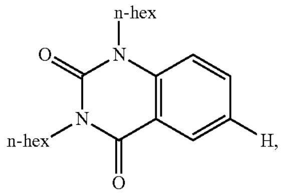
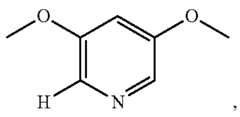
,
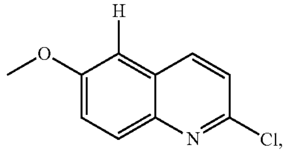
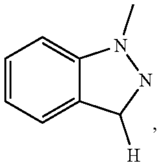
, and
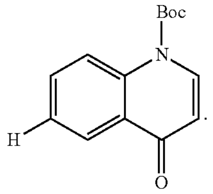
In one aspect, a compound can be present as:
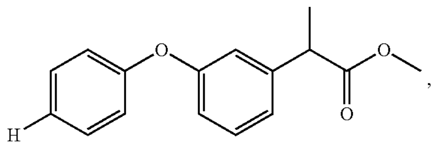

-continued

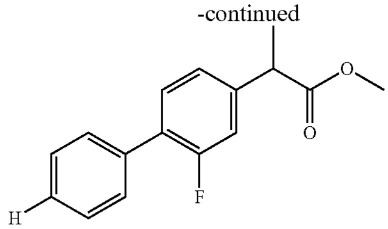

,

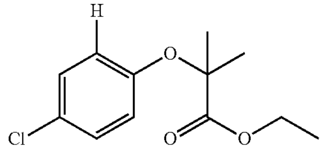

,

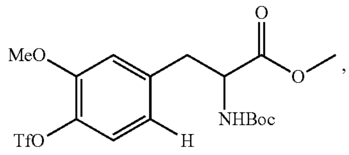

, and

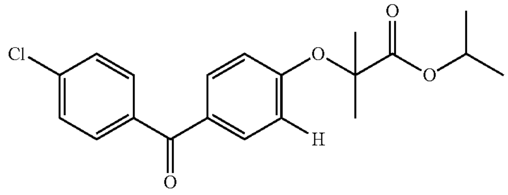

.

In one aspect, the arene can be present as:

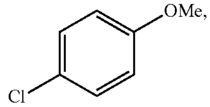

,

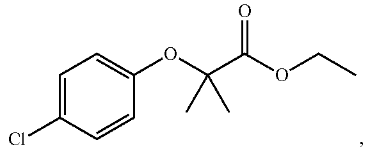

, and

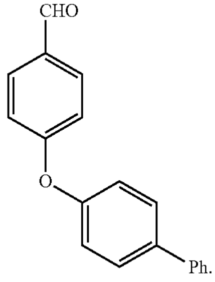

.

D. Acridinium Photocatalysts

In one aspect, disclosed are acridinium photocatalysts useful in the disclosed methods. It is contemplated that each disclosed derivative can be optionally further substituted. It is also contemplated that any one or more derivative can be optionally omitted from the invention. It is understood that a disclosed compound can be provided by the disclosed methods.

1. Structure

In one aspect, disclosed are acridinium photocatalysts having a structure represented by a formula:

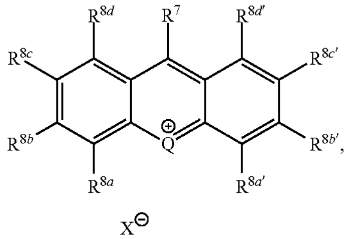

wherein Q is selected from 0 and $NR^9$; wherein $R^9$ is selected from C1-C4 alkyl, aryl, and heteroaryl, and is substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein X is selected from $BF_4$, TfO, $PF_6$, and C104; wherein $R^7$ is selected from C1-C4 alkyl and phenyl substituted with 0, 1, 2, or 3 groups independently selected from halogen and C1-C4 alkyl; and wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino.

In one aspect, disclosed are acridinium photocatalysts having a structure represented by a formula:

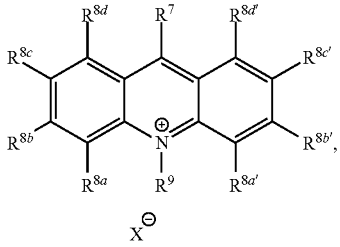

wherein X is selected from $BF_4$, TfO, $PF_6$, and $ClO_4$; wherein $R^7$ is selected from C1-C4 alkyl and phenyl substituted with 0, 1, 2, or 3 groups independently selected from halogen and C1-C4 alkyl; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^9$ is selected from C1-C4 alkyl, aryl, and heteroaryl, and is substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino.

In one aspect, disclosed are acridium photocatalysts having a structure:

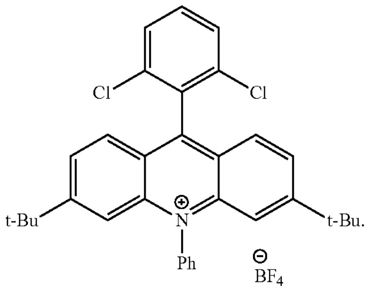
In a further aspect, the acridinium photocatalyst has a structure selected from:
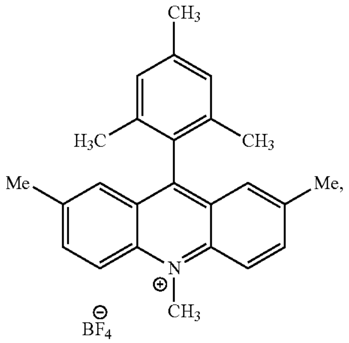
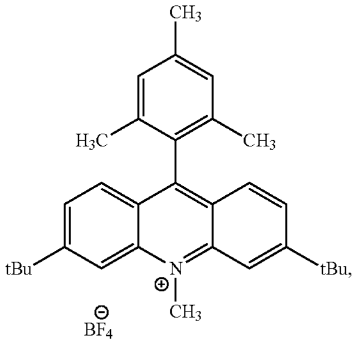
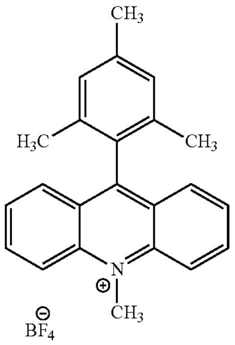
,
-continued
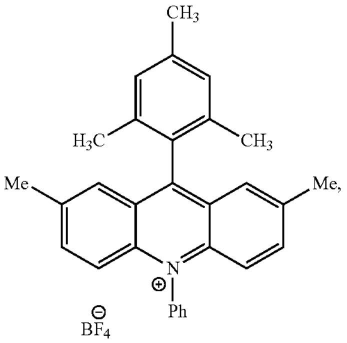
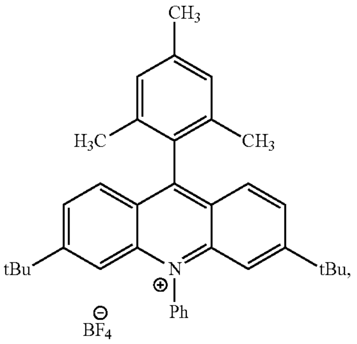
and
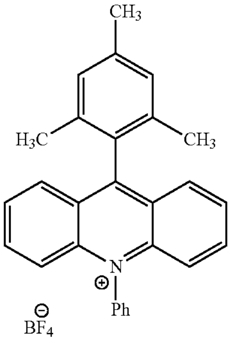
.
In a further aspect, the acridinium photocatalyst has a structure:
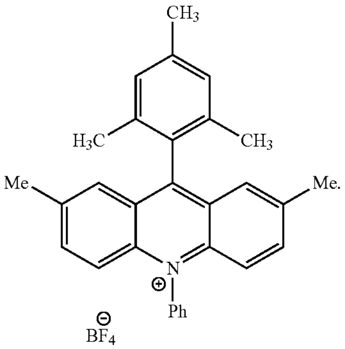
In a further aspect, the acridinium photocatalyst has a structure:

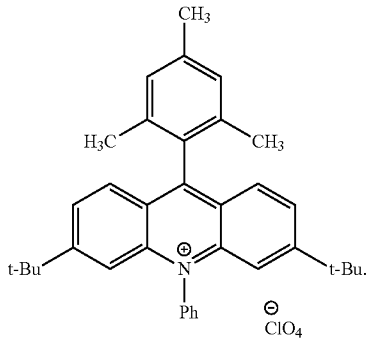

In various aspects, the acridinium photocatalyst is present in an amount of from about 0.1 mol % to about 10 mol %, from about 0.1 mol % to about 8 mol %, from about 0.1 mol % to about 6 mol %, from about 0.1 mol % to about 5 mol %, from about 0.1 mol % to about 4 mol %, from about 0.1 mol % to about 2 mol %, from about 2 mol % to about 10 mol %, from about 4 mol % to about 10 mol %, from about 5 mol % to about 10 mol %, from about 6 mol % to about 10 mol %, from about 8 mol % to about 10 mol %, from about 2 mol % to about 8 mol %, or from about 4 mol % to about 6 mol %.

In various aspects, the acridinium photocatalyst is present in an amount of about 0.1 mol %, about 2 mol %, about 4 mol %, about 5 mol %, about 6 mol %, about 8 mol %, or about 10 mol %. In a further aspect, the acridinium photocatalyst is present in an amount of about 5 mol %.

a. Q Groups

In one aspect, Q is selected from O and $NR^9$. In a further aspect, Q is O. In a still further aspect, Q is $NR^9$.

b. X Groups

In one aspect, X is selected from $BF_4$, TfO, $PF_6$, and $ClO_4$. In a further aspect, X is selected from $BF_4$, TfO, and $PF_6$. In a still further aspect, X is selected from $BF_4$ and $PF_6$. In yet a further aspect, X is $ClO_4$. In an even further aspect, X is TfO. In a still further aspect, X is $BF_4$. In yet a further aspect, X is $PF_6$.

c. $R^7$ Groups

In one aspect, $R^7$ is selected from C1-C4 alkyl and phenyl substituted with 0, 1, 2, or 3 groups independently selected from halogen and C1-C4 alkyl.

In a further aspect, $R^7$ is C1-C4 alkyl. In a still further aspect, $R^7$ is selected from methyl, ethyl, n-propyl, and iso-propyl. In yet a further aspect, $R^7$ is selected from methyl and ethyl. In an even further aspect, $R^7$ is ethyl. In a still further aspect, $R^7$ is methyl.

In a further aspect, $R^7$ is phenyl substituted with 0, 1, 2, or 3 groups independently selected from halogen and C1-C4 alkyl. In a still further aspect, $R^7$ is phenyl substituted with 0, 1, or 2 groups independently selected from halogen and C1-C4 alkyl. In yet a further aspect, $R^7$ is phenyl substituted with 0 or 1 group selected from halogen and C1-C4 alkyl. In an even further aspect, $R^7$ is phenyl monosubstituted with a group selected from halogen and C1-C4 alkyl. In a still further aspect, $R^7$ is unsubstituted phenyl.

In a further aspect, $R^7$ is phenyl substituted with 0, 1, 2, or 3 groups independently selected from fluorine, chlorine, methyl, ethyl, n-propyl, iso-propyl, n-butyl, sec-butyl, iso-butyl, and tert-butyl. In a still further aspect, $R^7$ is phenyl substituted with 0, 1, 2, or 3 groups independently selected from fluorine, chlorine, methyl, ethyl, n-propyl, and iso-propyl. In yet a further aspect, $R^7$ is phenyl substituted with 0, 1, 2, or 3 groups independently selected from fluorine, chlorine, methyl, and ethyl. In an even further aspect, $R^7$ is phenyl substituted with 0, 1, 2, or 3 groups independently selected from fluorine, chlorine, and methyl.

In a further aspect, $R^7$ is phenyl substituted with 0, 1, 2, or 3 groups independently selected from methyl, ethyl, n-propyl, iso-propyl, n-butyl, sec-butyl, iso-butyl, and tert-butyl. In a still further aspect, $R^7$ is phenyl substituted with 0, 1, 2, or 3 groups independently selected from methyl, ethyl, n-propyl, and iso-propyl. In yet a further aspect, $R^7$ is phenyl substituted with 0, 1, 2, or 3 groups independently selected from methyl, and ethyl. In an even further aspect, $R^7$ is phenyl substituted with 0, 1, 2, or 3 methyl groups.

d. $R^{8A}$, $R^{8B}$, $R^{8C}$, $R^{8D}$, $R^{8A'}$, $R^{8B'}$, $R^{8C'}$, and $R^{8D'}$ Groups In one aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, and (C1-C4)(C1-C4) dialkylamino.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, and (C1-C4)(C1-C4) dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, ethyl, —$OCH_3$, —$OCH_2CH_3$, —$OCH(CH_3)_2$, —$NHCH_3$, —$N(CH_3)_2$, —$N(CH_3)(CH_2CH_3)$, and —$N(CH_2CH_3)_2$. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, methyl, —$OCH_3$, —$OCH(CH_3)_2$, —$NHCH_3$, and —$N(CH_3)_2$.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, C1-C4 alkyl, C1-C4 alkoxy, C1-C4 alkylamino, and C1-C4 dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, —$OCH_3$, —$OCH_2CH_3$, —$OCH(CH_3)_2$, —$NHCH_3$, —$N(CH_3)_2$, —$N(CH_3)(CH_2CH_3)$, and —$N(CH_2CH_3)_2$. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, —$OCH_3$, —$OCH(CH_3)_2$, —$NHCH_3$, and —$N(CH_3)_2$.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and C1-C4 alkyl. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, ethyl, n-propyl, and iso-propyl. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, methyl, and ethyl. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and methyl.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and halogen. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, fluorine, and chlorine. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and fluorine. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and chlorine.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from halogen, —$CF_3$, —$NH_2$, C1-C4 alkyl, C1-C4 alkoxy, C1-C4 alkylamino, and (C1-C4)(C1-C4) dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, or 2 groups independently selected from halogen, —$CF_3$, —$NH_2$, C1-C4 alkyl, C1-C4 alkoxy, C1-C4 alkylamino, and (C1-C4)(C1-C4) dialkylamino. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0 or 1 group selected from halogen, —$CF_3$, —$NH_2$, C1-C4 alkyl, C1-C4 alkoxy, C1-C4 alkylamino, and (C1-C4)(C1-C4) dialkylamino. In an even further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl monosubstituted with a group selected from halogen, —$CF_3$, —$NH_2$, C1-C4 alkyl, C1-C4 alkoxy, C1-C4 alkylamino, and (C1-C4)(C1-C4) dialkylamino. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and unsubstituted phenyl.

In a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from halogen, —$CF_3$, —$NH_2$, methyl, ethyl, n-propyl, iso-propyl, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)(CH_2CH_3)$, —$N(CH_3)(CH_2CH_2CH_3)$, —$N(CH_3)(CH(CH_3)_2)$, —$N(CH_2CH_3)_2$, —$N(CH_2CH_3)(CH_2CH_2CH_3)$, —$N(CH_2CH_3)(CH(CH_3)_2)$, —$N(CH_2CH_2CH_3)_2$, —$N(CH_2CH_2CH_3)(CH(CH_3)_2)$, and —$N(CH(CH_3)_2)_2$. In a still further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from fluorine, chlorine, —$CF_3$, —$NH_2$, methyl, ethyl, —$OCH_3$, —$OCH_2CH_3$, —$NHCH_3$, —$NHCH_2CH_3$, —$N(CH_3)_2$, —$N(CH_3)(CH_2CH_3)$, and —$N(CH_2CH_3)_2$. In yet a further aspect, each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen and phenyl substituted with 0, 1, 2, or 3 groups independently selected from fluorine, chlorine, —$CF_3$, —$NH_2$, methyl, —$OCH_3$, —$NHCH_3$, and —$N(CH_3)_2$.

e. $R^9$ Groups

In one aspect, $R^9$ is selected from C1-C4 alkyl, aryl, and heteroaryl, and is substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a further aspect, $R^9$ is selected from C1-C4 alkyl, aryl, and heteroaryl, and is substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is selected from C1-C4 alkyl, aryl, and heteroaryl, and is substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In yet a further aspect, $R^9$ is selected from C1-C4 alkyl, aryl, and heteroaryl, and is monosubstituted with a group selected from halogen, —$CF_3$, —$NH_2$, C1-C4 alkyl, C1-C4 alkoxy, C1-C4 alkylamino, (C1-C4)(C1-C4) dialkylamino. In an even further aspect, $R^9$ is selected from C1-C4 alkyl, aryl, and heteroaryl, and is unsubstituted.

In a further aspect, $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino.

In a further aspect, $R^9$ is C1-C4 alkyl. In a still further aspect, $R^9$ is selected from methyl, ethyl, n-propyl, and iso-propyl. In yet a further aspect, $R^9$ is selected from methyl and ethyl. In an even further aspect, $R^9$ is ethyl. In a still further aspect, $R^9$ is methyl.

In a further aspect, $R^9$ is selected from aryl and heteroaryl, and is substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is selected from aryl and heteroaryl, and is substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In yet a further aspect, $R^9$ is selected from aryl and heteroaryl, and is substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In an even further aspect, $R^9$ is selected from aryl and heteroaryl, and is monosubstituted with a group selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is selected from aryl and heteroaryl, and is unsubstituted.

In a further aspect, $R^9$ is aryl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is aryl substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In yet a further aspect, $R^9$ is aryl substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In an even further aspect, $R^9$ is aryl monosubstituted with a group selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is unsubstituted aryl.

In a further aspect, $R^9$ is phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino. In a still further aspect, $R^9$ is phenyl substituted with 0, 1, or 2 groups independently selected from halogen, —$CF_3$, —$NH_2$, C1-C4 alkyl, C1-C4 alkoxy, C1-C4 alkylamino, (C1-C4)(C1-C4) dialkylamino. In yet a further aspect, $R^9$ is phenyl substituted with 0 or 1 group selected from halogen, —$CF_3$, —$NH_2$, C1-C4 alkyl, C1-C4 alkoxy, C1-C4 alkylamino, (C1-C4)(C1-C4) dialkylamino. In an even further aspect, $R^9$ is phenyl monosubstituted with a group selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is unsubstituted phenyl.

In a further aspect, $R^9$ is phenyl substituted with 0, 1, 2, or 3 groups independently selected from fluorine, chlorine, $-CF_3$, $-NH_2$, methyl, ethyl, n-propyl, iso-propyl, $-OCH_3$, $-OCH_2CH_3$, $-OCH_2CH_2CH_3$, $-OCH(CH_3)_2$, $-NHCH_3$, $-NHCH_2CH_3$, $-NHCH_2CH_2CH_3$, $-NHCH(CH_3)_2$, $-N(CH_3)_2$, $-N(CH_3)(CH_2CH_3)$, $-N(CH_3)(CH_2CH_2CH_3)$, $-N(CH_3)(CH(CH_3)_2)$, $-N(CH_2CH_3)_2$, $-N(CH_2CH_3)(CH_2CH_2CH_3)$, $-N(CH_2CH_3)(CH(CH_3)_2)$, $-N(CH_2CH_2CH_3)_2$, $-N(CH_2CH_2CH_3)(CH(CH_3)_2)$, and $-N(CH(CH_3)_2)_2$. In a still further aspect, $R^9$ is phenyl substituted with 0, 1, 2, or 3 groups independently selected from fluorine, chlorine, $-CF_3$, $-NH_2$, methyl, ethyl, $-OCH_3$, $-OCH_2CH_3$, $-OCH(CH_3)_2$, $-NHCH_3$, $-NHCH_2CH_3$, $-N(CH_3)_2$, $-N(CH_3)(CH_2CH_3)$, and $-N(CH_2CH_3)_2$. In yet a further aspect, $R^9$ is phenyl substituted with 0, 1, 2, or 3 groups independently selected from fluorine, chlorine, methyl, $-CF_3$, $-NH_2$, $-OCH_3$, $-NHCH_3$, and $-N(CH_3)_2$.

In a further aspect, $R^9$ is heteroaryl substituted with 0, 1, 2, or 3 groups independently selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is heteroaryl substituted with 0, 1, or 2 groups independently selected from halogen, $-CF_3$, $-NH_2$, C1-C4 alkyl, C1-C4 alkoxy, C1-C4 alkylamino, (C1-C4)(C1-C4) dialkylamino. In yet a further aspect, $R^9$ is heteroaryl substituted with 0 or 1 group selected from halogen, $-CF_3$, $-NH_2$, C1-C4 alkyl, C1-C4 alkoxy, C1-C4 alkylamino, (C1-C4)(C1-C4) dialkylamino. In an even further aspect, $R^9$ is heteroaryl monosubstituted with a group selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is unsubstituted heteroaryl.

In a further aspect, $R^9$ is 5-membered heteroaryl substituted with 0, 1, 2, or 3 groups independently selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is 5-membered heteroaryl substituted with 0, 1, or 2 groups independently selected from halogen, $-CF_3$, $-NH_2$, C1-C4 alkyl, C1-C4 alkoxy, C1-C4 alkylamino, (C1-C4)(C1-C4) dialkylamino. In yet a further aspect, $R^9$ is 5-membered heteroaryl substituted with 0 or 1 group selected from halogen, $-CF_3$, $-NH_2$, C1-C4 alkyl, C1-C4 alkoxy, C1-C4 alkylamino, (C1-C4)(C1-C4) dialkylamino. In an even further aspect, $R^9$ is 5-membered heteroaryl monosubstituted with a group selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is unsubstituted 5-membered heteroaryl.

In a further aspect, $R^9$ is 6-membered heteroaryl substituted with 0, 1, 2, or 3 groups independently selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is 6-membered heteroaryl substituted with 0, 1, or 2 groups independently selected from halogen, $-CF_3$, $-NH_2$, C1-C4 alkyl, C1-C4 alkoxy, C1-C4 alkylamino, (C1-C4)(C1-C4) dialkylamino. In yet a further aspect, $R^9$ is 6-membered heteroaryl substituted with 0 or 1 group selected from halogen, $-CF_3$, $-NH_2$, C1-C4 alkyl, C1-C4 alkoxy, C1-C4 alkylamino, (C1-C4)(C1-C4) dialkylamino. In an even further aspect, $R^9$ is 6-membered heteroaryl monosubstituted with a group selected from halogen, $-CF_3$, $-NH_2$, C1-C4 alkyl, C1-C4 alkoxy, C1-C4 alkylamino, (C1-C4)(C1-C4) dialkylamino. In a still further aspect, $R^9$ is unsubstituted 6-membered heteroaryl.

2. Example Photocatalyst Structures

In one aspect, an acridinium photocatalyst can be present as:

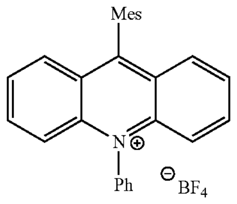
,

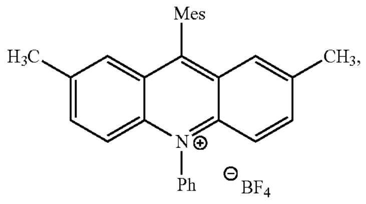

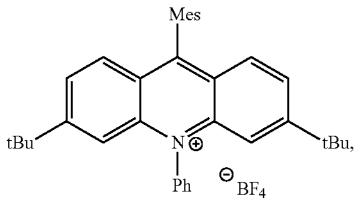
or

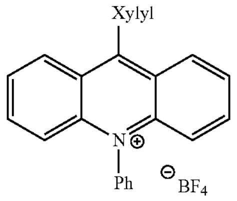
.

In one aspect, an acridinium photocatalyst can be present as:

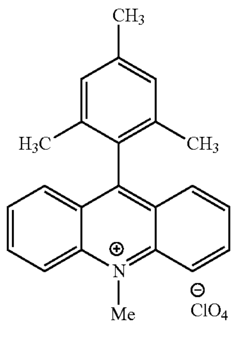
,

-continued
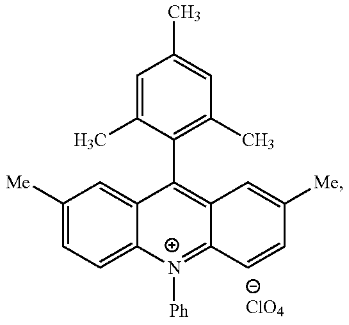
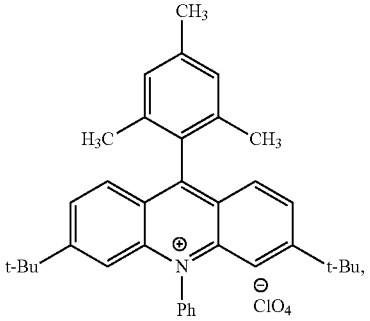
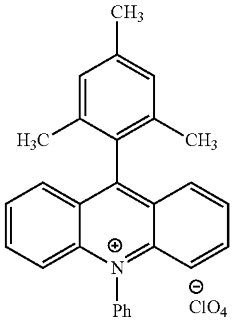
,
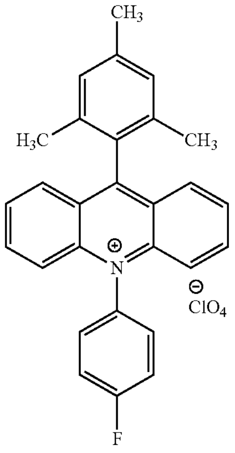
, or
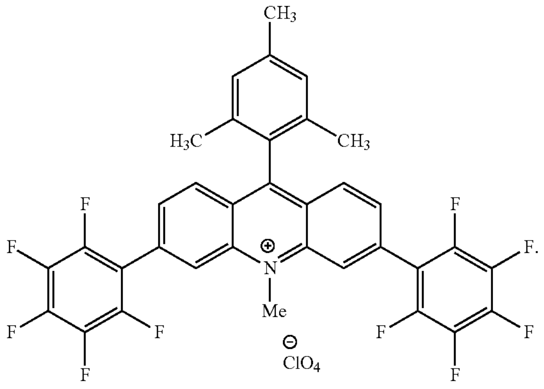
In one aspect, an acridinium photocatalyst can be present as:
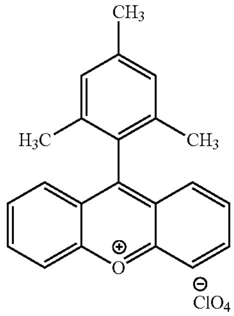
,
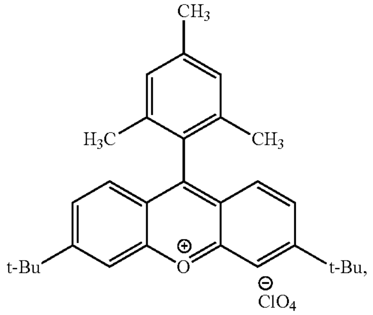
or
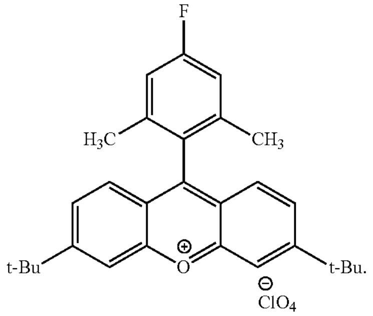
In one aspect, an acridinium photocatalyst can be present as:
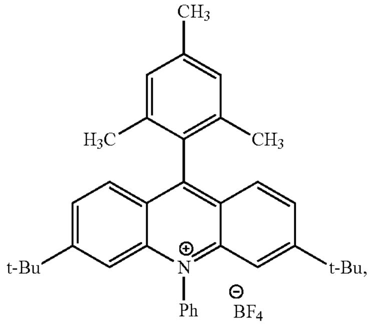

-continued
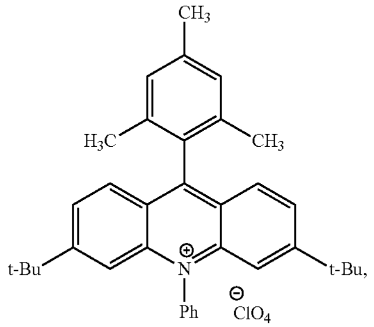
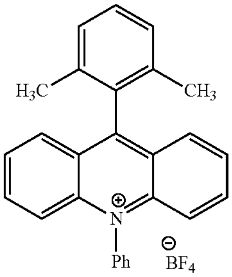
,
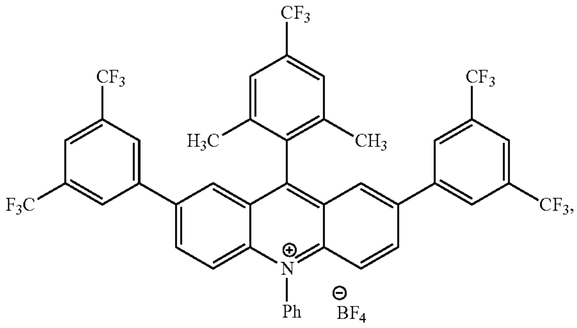
,
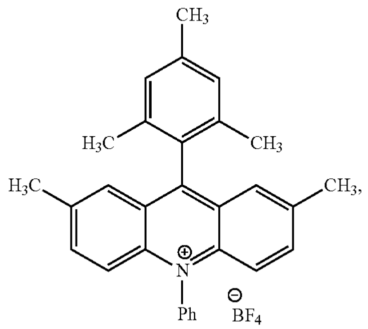
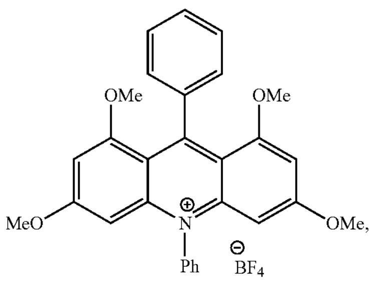
-continued
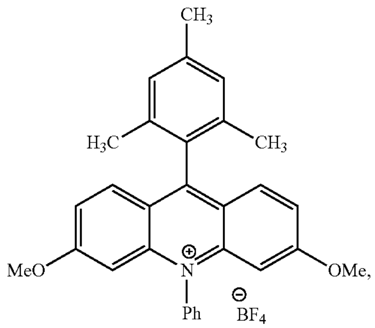
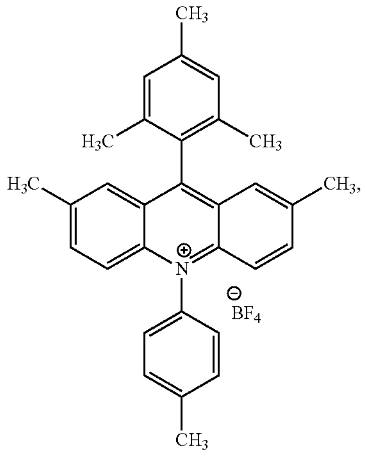
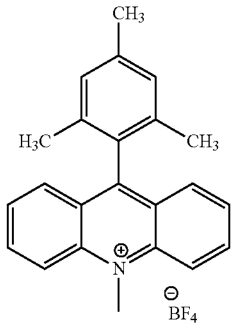
,
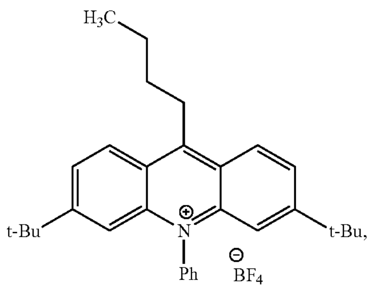
and -continued

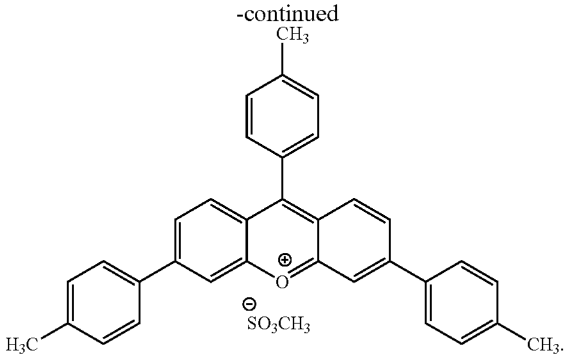

In one aspect, an acridinium photocatalyst can be present as:

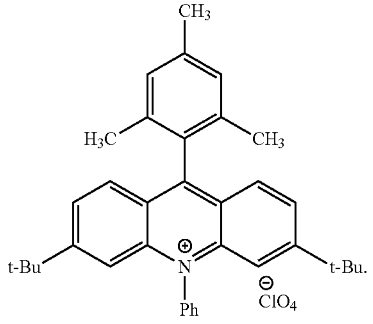

E. Methods of Making the Disclosed Compounds

In one aspect, disclosed are methods of making a compound having a structure represented by a formula:

$Ar^1$—Z, wherein Z is selected from halogen, —CN, —$NH_2$, C1-C4 alkylamino, and (C1-C4)(C1-C4) dialkylamino, provided that when Z is —$NH_2$, C1-C4 alkylamino, or (C1-C4)(C1-C4) dialkylamino that Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{15b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{30}$ and $R^{32}$, when present, is independently selected from hydrogen and C1-C4 alkyl; wherein each of $R^{31a}$ and $R^{31b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

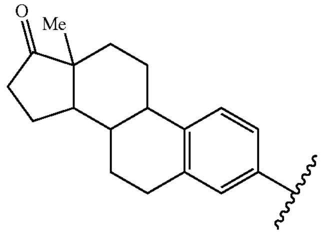

, the method comprising the step of reacting an arene having a structure represented by a formula:

$Ar^1$-E, wherein E is an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, and under anaerobic conditions, thereby forming the compound. In a further aspect, the compound is made by displacement of the E group with the Z group. Thus, in various aspects, the group designated as "E" in the arene is no longer present in the resultant compound.

In one aspect, disclosed are methods of making a compound having a structure represented by a formula:

$Ar^1$—Z, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

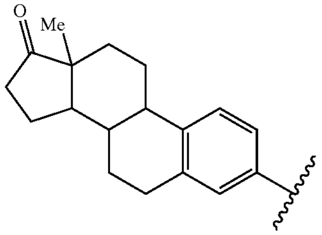

, the method comprising the step of reacting an arene having a structure represented by a formula:

$Ar^1$-E, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, thereby forming the compound. In a further aspect, the compound is made by displacement of the E group with the Z group. Thus, in various aspects, the group designated as "E" in the arene is no longer present in the resultant compound.

In one aspect, disclosed are methods of making a compound having a structure represented by a formula:

$Ar^1$—Z, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}$($NR^{14a}R^{14b}$)$CO_2R^{15}$; wherein each of $R^{10}$, RD, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

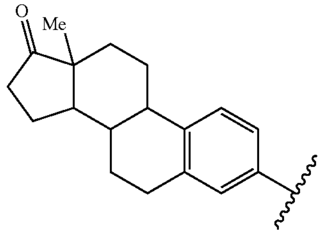

, the method comprising the step of reacting an arene having a structure represented by a formula:

$Ar^1$-E, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, —OC(═O)$NHR^{20}$; wherein $R^{20}$, $R^{21a}$, and $R^{21b}$, when present, is independently selected from hydrogen, C1-C8 alkyl, C1-C8 alkenyl, and Ar; and wherein $Ar^3$, when present, is selected from aryl and heteroaryl and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, thereby forming the compound.

In one aspect, disclosed are methods of making a compound having a structure represented by a formula:

$Ar^1$—Z, wherein Z is halogen and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}$($NR^{14a}R^{14b}$)$CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

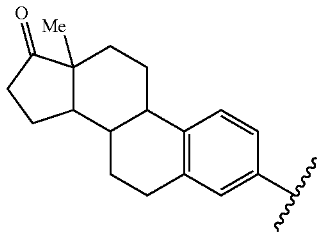

, the method comprising the step of reacting an arene having a structure represented by a formula:

$Ar^1—H$, with a halide, in the presence of a LED having a wavelength of about 425 nm, TBPA, and a catalytically effective amount of an acridinium photocatalyst having a structure:

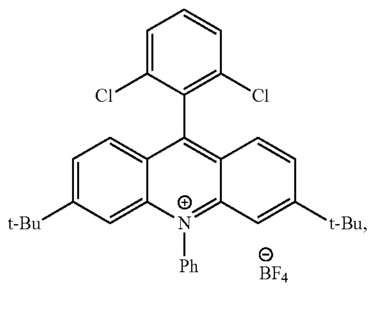

thereby forming the compound.

In one aspect, disclosed are methods of making a compound having a structure represented by a formula:

$Ar^1—X$, wherein X is halogen and wherein X contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

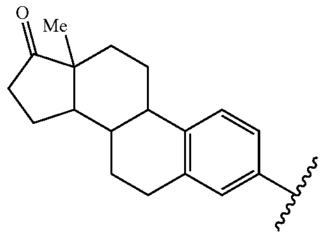

, the method comprising the step of reacting an arene having a structure represented by a formula:

$Ar^1—X'$, wherein X' is halogen and wherein X' does not contain a radioisotope, with a nucleophile selected from a halide, a cyanide, and an amine, in the presence of a catalytically effective amount of an acridinium photocatalyst, thereby forming the compound. In a further aspect, the compound is made by displacement of the X' group with the X group. Thus, in various aspects, the group designated as "X'" in the arene is no longer present in the resultant compound.

In one aspect, disclosed are methods of making a compound having a structure represented by a formula:

$Ar^1$-E, wherein Z is selected from halogen, —CN, —$NH_2$, C1-C4 alkylamino, and (C1-C4)(C1-C4) dialkylamino and wherein Z contains a radioisotope; wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}(NR^{14a}R^{14b})CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

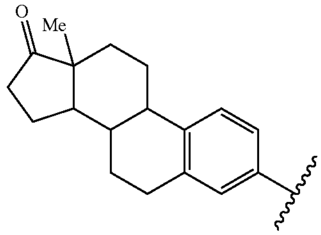

, the method comprising the step of reacting an arene having a structure represented by a formula:

$Ar^1$-E, wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a catalytically effective amount of an acridinium photocatalyst, thereby forming the compound. In a further aspect, reacting is under anaerobic conditions. In a still further aspect, reacting is under aerobic conditions.

In a further aspect, E is para to Z. In a still further aspect, E is ortho to Z. In yet a further aspect, E is not meta to Z.

In a further aspect, the catalytically effective amount is of from about 0.01 mol % to about 15 mol %. In a still further aspect, the catalytically effective amount is of from about 0.01 mol % to about 12 mol %. In yet a further aspect, the catalytically effective amount is of from about 0.01 mol % to about 10 mol %. In an even further aspect, the catalytically effective amount is of from about 0.01 mol % to about 7 mol %. In a still further aspect, the catalytically effective amount is of from about 0.01 mol % to about 5 mol %. In yet a further aspect, the catalytically effective amount is of from about 0.01 mol % to about 2 mol %. In an even further aspect, the catalytically effective amount is of from about 0.01 mol % to about 1 mol %. In a still further aspect, the catalytically effective amount is of from about 0.01 mol % to about 0.1 mol %.

In a further aspect, the catalytically effective amount is of from about 0.1 mol % to about 10 mol %. In a still further aspect, the catalytically effective amount is of from about 0.1 mol % to about 7 mol %. In a still further aspect, the catalytically effective amount is of from about 0.1 mol % to about 5 mol %. In yet a further aspect, the catalytically effective amount is of from about 0.1 mol % to about 2 mol %. In an even further aspect, the catalytically effective amount is of from about 0.1 mol % to about 1 mol %. In a still further aspect, the catalytically effective amount is 5 mol %.

In a further aspect, the catalytically effective amount is of from about 0.1 mol % to about 15 mol %. In a still further aspect, the catalytically effective amount is of from about 1 mol % to about 15 mol %. In yet a further aspect, the catalytically effective amount is of from about 2 mol % to about 15 mol %. In an even further aspect, the catalytically effective amount is of from about 5 mol % to about 15 mol %. In a still further aspect, the catalytically effective amount is of from about 7 mol % to about 15 mol %. In yet a further aspect, the catalytically effective amount is of from about 10 mol % to about 15 mol %. In an even further aspect, the catalytically effective amount is of from about 12 mol % to about 15 mol %.

In a further aspect, the acridinium photocatalyst has a structure represented by a formula:

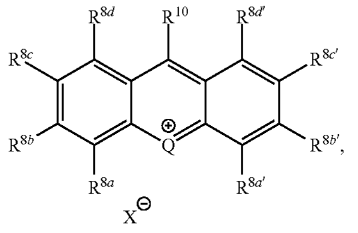

wherein Q is selected from 0 and $NR^9$; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

In a further aspect, the acridinium photocatalyst has a structure represented by a formula:

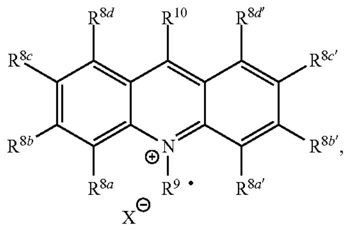

wherein X is selected from $BF_4$, TfO, $PF_6$, and $ClO_4$; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^{10}$ is selected from C1-C4 alkyl and phenyl substituted with 0, 1, 2, or 3 groups independently selected from halogen and C1-C4 alkyl.

In a further aspect, the acridinium photocatalyst has a structure selected from:

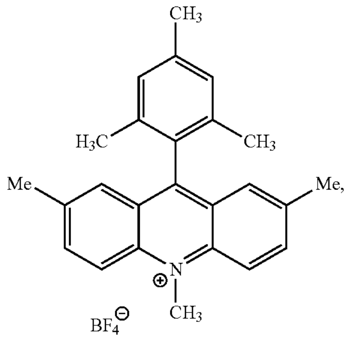

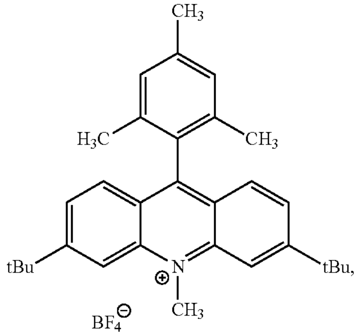

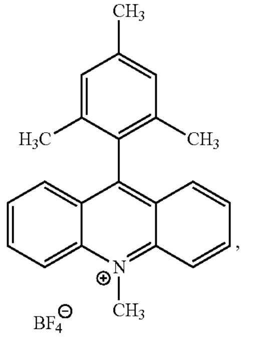

-continued

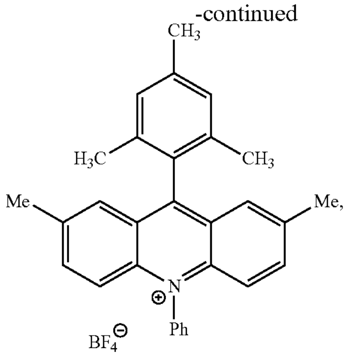

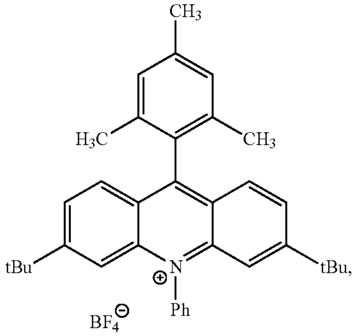

and

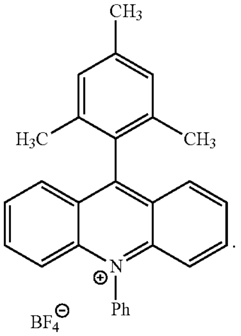

In a further aspect, the acridinium photocatalyst has a structure:

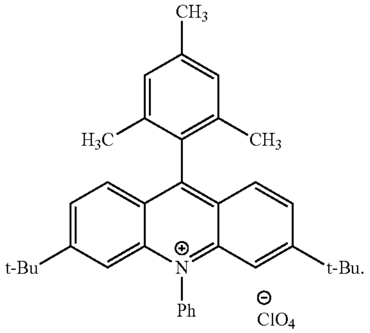

As used herein, the term "nucleophile" refers to a molecule, atom, or ion that is capable of forming a chemical bond to its reaction partner by donating electrons. Exemplary nucleophiles are well known by those skilled in the art and include, but are not limited to, water, ammonia, halides, cyanides, alcohols, thiols, amines, hydrazines, carbamates, carboxylic acids, and alkenes. In a further aspect, the nucleophile is selected from a halide, a cyanide, and an amine.

In a further aspect, the nucleophile is isotopically-labeled. In a still further aspect, the nucleophile is not isotopically-labeled.

In a further aspect, the nucleophile is a halide. Exemplary halides are well known by those skilled in the art and include, but are not limited to, ammonium fluoride, cesium fluoride, lithium chloride, triethylamine hydrochloride, and triethylamine hydrofluoride. In a further aspect, the nucleophile is a halide. In a still further aspect, the nucleophile is a fluoride. Exemplary of fluorides includes, but are not limited to, ammonium fluoride, cesium fluoride, triethylamine hydrofluoride, and tetrabutylammonium fluoride.

In a further aspect, the nucleophile is an amine. Exemplary amines include, but are not limited to, ammonium bicarbonate.

In a further aspect, the nucleophile is a cyanide. Exemplary cyanides include, but are not limited to, tetrabutylammonium cyanide, sodium cyanide, potassium cyanide, and acetonecyanohydrin.

In a further aspect, reacting is under anaerobic conditions. Thus, in various aspects, reacting is in the absence of an oxidant or an oxidizing agent. As used herein the terms "oxidant" and "oxidizing agent" refer to any species that is capable of accepting or taking electrons from another species. Exemplary oxidants are well known by those skilled in the art and include, but are not limited to, molecular oxygen, 2,2,6,6-tetramethyl-1-piperidinyloxy radical (TEMPO), ozone, and hydrogen peroxide. In a further aspect, the oxidant is molecular oxygen. In a still further aspect, the oxidant is TEMPO.

In a further aspect, reacting is under inert atmosphere. Thus, in various aspects, reacting is in the presence of an inert gas (e.g., argon, nitrogen). In various further aspects, reacting is in the absence of oxygen or carbon dioxide.

In a further aspect, reacting is in the presence of a visible light source. Examples of visible light sources include, but are not limited to, lasers, light-emitting diodes (LEDs), non-LED lights, light generated by up-conversion particles, phosphor materials, and an x-ray generated light. In a further aspect, the light source is a bioluminescence light source, a chemoluminescence light source, or an electro-luminescence light source.

In a still further aspect, the visible light source has a wavelength of from about 365 nm to about 480 nm. In yet a further aspect, the visible light source has a wavelength of from about 365 nm to about 450 nm. In an even further aspect, the visible light source has a wavelength of from about 365 nm to about 420 nm. In a still further aspect, the visible light source has a wavelength of from about 365 nm to about 400 nm. In yet a further aspect, the visible light source has a wavelength of from about 365 nm to about 380 nm. In an even further aspect, the visible light source has a wavelength of from about 380 nm to about 480 nm. In a still further aspect, the visible light source has a wavelength of from about 400 nm to about 480 nm. In yet a further aspect, the visible light source has a wavelength of from about 420 nm to about 480 nm. In an even further aspect, the visible light source has a wavelength of from about 450 nm to about 480 nm. In a still further aspect, the visible light source has a wavelength of about 365 nm, about 380 nm, about 400 nm, about 420 nm, about 450 nm, or about 480 nm.

In a further aspect, reacting is in the presence of a visible light source. In a still further aspect, the visible light source is a light-emitting diode (LED). In yet a further aspect, the visible light source has a wavelength of from about 365 nm to about 480 nm.

In a further aspect, the visible light source has a wavelength of about 415 nm, about 420 nm, about 425 nm, about 430 nm, about 435 nm, about 440 nm, about 445 nm, or about 450 nm. In various further aspect, the visible light source has a wavelength of about 425 nm.

In a further aspect, reacting is in the presence of an oxidant. Examples of oxidants include, but are not limited to, tert-butyl peroxybenzoate (TBPB), tert-butyl peroxyacetate (TBPA), benzoyl peroxide (BPO), tert-butyl hydroperoxide (TBHP), and pyridinium chlorochromate (PCC). In various further aspects, the oxidant is TBPA.

In a further aspect, reacting is in the presence of a solvent. Examples of solvents include, but are not limited to, tert-butanol, acetonitrile, dimethyl sulfoixde, toluene, dichloromethane, tetrahydofuran, N,N-dimethylformate, 1,4-dioxane, and methanol. In various further aspects, the solvent is tertbutanol.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

1. Route I

In one aspect, a disclosed compound can be prepared as shown below.

SCHEME 1A.

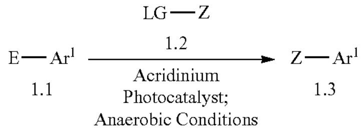

1.1 1.3

Compounds are represented in generic form, wherein LG is a leaving group having a Z substituent and with substituents as noted in compound descriptions elsewhere herein. A more specific example is set forth below.

SCHEME 1B.

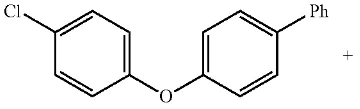
1.4

-continued

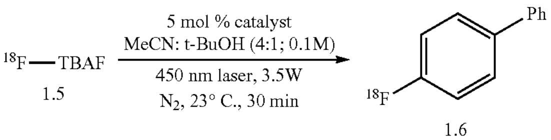

1.5 1.6

In one aspect, compounds of type 1.3, and similar compounds, can be prepared according to reaction Scheme 1B above. Thus, compounds of type 1.6 can be prepared by an aromatic C—O functionalization reaction of an appropriate arene, e.g., 1.4 as shown above. Appropriate arenes are commercially available or prepared by methods known to one skilled in the art. The aromatic C—O functionalization reaction is carried out in the presence of an appropriate nucleophile, e.g., 1.5 as shown above, which is commercially available or prepared by methods known to one skilled in the art, an appropriate catalyst, e.g., 5 mol % acridinium photocatalyst, under anaerobic conditions, e.g., under nitrogen atmosphere, at an appropriate temperature, e.g., 23° C., for an appropriate period of time, e.g., 30 minutes, in an appropriate solvent system, e.g., acetonitrile: t-butanol (4:1, 0.1 M). Alternatively, the aromatic C—O functionalization reaction is carried out in the presence of an appropriate nucleophile, e.g., 1.5 as show above, an appropriate catalyst, e.g., 5 mol % acridinium photocatalyst, under air at an appropriate temperature, e.g., 0° C., for an appropriate period of time, e.g., 30 minutes, in an appropriate solvent system, e.g., acetonitrile: t-butanol: 1,2-dichloroethane (4:1: 3, 800 uL). As can be appreciated by one skilled in the art, the above reaction provides an example of a generalized approach wherein compounds similar in structure to the specific reactants above (compounds similar to compounds of type 1.4 and 1.5), can be substituted in the reaction to provide compounds similar to Formula 1.6.

2. Route II

In one aspect, a disclosed compound can be prepared as shown below.

SCHEME 2A.

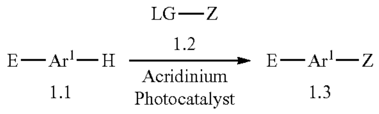

1.1 1.3

Compounds are represented in generic form, wherein LG is a leaving group having a Z substituent and with substituents as noted in compound descriptions elsewhere herein. A more specific example is set forth below.

SCHEME 2B

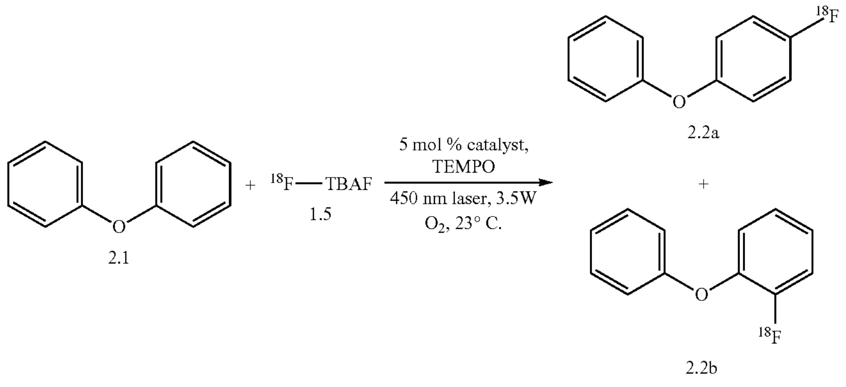

In one aspect, compounds of type 1.3, and similar compounds, can be prepared according to reaction Scheme 2B above. Thus, compounds of type 2.2a and 2.2b can be prepared by an aromatic C—H functionalization reaction of an appropriate arene, e.g., 2.1 as shown above. Appropriate arenes are commercially available or prepared by methods known to one skilled in the art. The aromatic C—H functionalization reaction is carried out in the presence of an appropriate nucleophile, e.g., 1.5 as shown above, which is commercially available or prepared by methods known to one skilled in the art, an appropriate catalyst, e.g., 5 mol % acridinium photocatalyst in the presence of TEMPO, under aerobic conditions, e.g., under molecular oxygen, at an appropriate temperature, e.g., 23° C. As can be appreciated by one skilled in the art, the above reaction provides an example of a generalized approach wherein compounds similar in structure to the specific reactants above (compounds similar to compounds of type 1.5 and 2.1), can be substituted in the reaction to provide compounds similar to Formula 2.2a and 2.2b.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

F. Catalyst Systems

In one aspect, disclosed are catalyst systems comprising an acridinium photocatalyst and a nucleophile selected from a halide, a cyanide, and an isotopically-labeled amine, wherein the catalyst system is anaerobic.

In one aspect, disclosed are catalyst systems comprising an acridinium photocatalyst, an isotopically-labeled halide, and an oxidant.

In a further aspect, the acridinium photocatalyst has a structure represented by a formula:

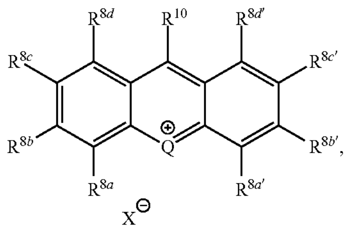

wherein Q is selected from 0 and $NR^9$; wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; wherein X is selected from $BF_4$, TfO, $PF_6$, and $ClO_4$; wherein $R^7$ is selected from C1-C4 alkyl and phenyl substituted with 0, 1, 2, or 3 groups independently selected from halogen and C1-C4 alkyl; and wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, and (C1-C4)(C1-C4) dialkylamino.

In a further aspect, the acridinium photocatalyst has a structure represented by a formula:

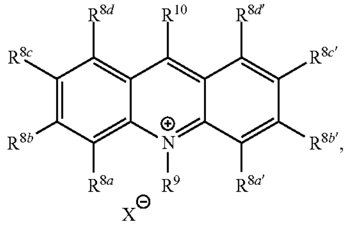

wherein X is selected from $BF_4$, TfO, $PF_6$, and $ClO_4$; wherein $R^7$ is selected from C1-C4 alkyl and phenyl substituted with 0, 1, 2, or 3 groups independently selected from halogen and C1-C4 alkyl; wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino; and wherein $R^9$ is selected from C1-C4 alkyl and phenyl substituted with 0, 1, 2, or 3 groups independently selected from halogen, —$CF_3$, —$NH_2$, C1-C4 alkyl, C1-C4 alkoxy, C1-C4 alkylamino, and (C1-C4)(C1-C4) dialkylamino.

In a further aspect, the acridinium photocatalyst has a structure selected from:

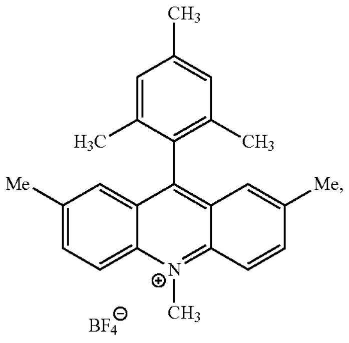

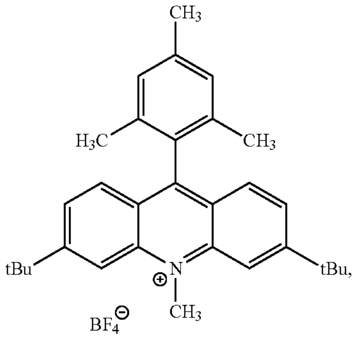

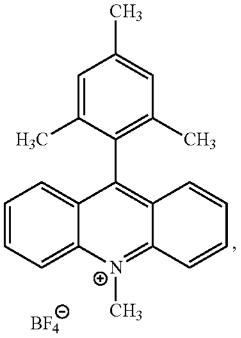

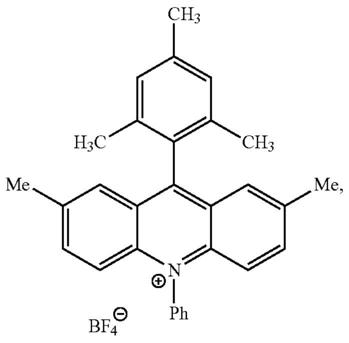

-continued

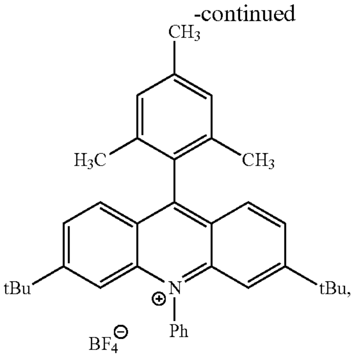

and

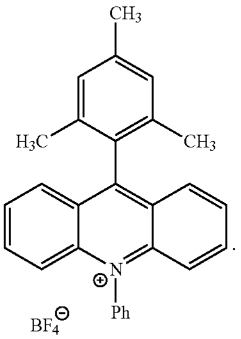

In a further aspect, the acridinium photocatalyst has a structure:

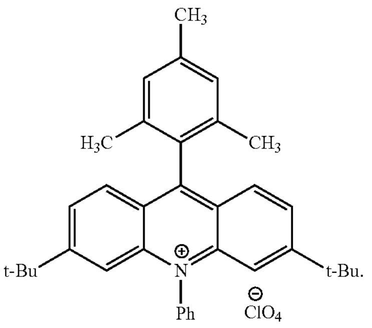

In a further aspect, the acridinium photocatalyst has a structure:

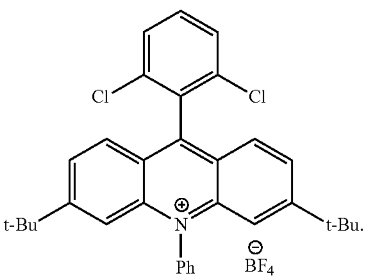

In a further aspect, the acridinium photocatalyst is present in a catalytically effective amount. Thus, in various aspects, the catalytically effective amount is of from about 0.01 mol % to about 15 mol %, from about 0.01 mol % to about 12 mol %, from about 0.01 mol % to about 10 mol %, from about 0.01 mol % to about 7 mol %, from about 0.01 mol % to about 5 mol %, from about 0.01 mol % to about 2 mol %, from about 0.01 mol % to about 1 mol %, or from about 0.01 mol % to about 0.1 mol %. In various further aspects, the catalytically effective amount is of from about 0.1 mol % to about 10 mol %, from about 0.1 mol % to about 7 mol %, from about 0.1 mol % to about 5 mol %, from about 0.1 mol % to about 2 mol %, or from about 0.1 mol % to about 1 mol %. In a still further aspect, the catalytically effective amount is 5 mol %.

In a further aspect, the catalytically effective amount is of from about 0.1 mol % to about 15 mol %. In a still further aspect, the catalytically effective amount is of from about 1 mol % to about 15 mol %. In yet a further aspect, the catalytically effective amount is of from about 2 mol % to about 15 mol %. In an even further aspect, the catalytically effective amount is of from about 5 mol % to about 15 mol %. In a still further aspect, the catalytically effective amount is of from about 7 mol % to about 15 mol %. In yet a further aspect, the catalytically effective amount is of from about 10 mol % to about 15 mol %. In an even further aspect, the catalytically effective amount is of from about 12 mol % to about 15 mol %.

As used herein, the term "nucleophile" refers to a molecule, atom, or ion that is capable of forming a chemical bond to its reaction partner by donating electrons. Exemplary nucleophiles are well known by those skilled in the art and include, but are not limited to, water, ammonia, halides, cyanides, alcohols, thiols, amines, hydrazines, carbamates, carboxylic acids, and alkenes. In a further aspect, the nucleophile is selected from a halide, a cyanide, and an isotopically-labeled amine.

In a further aspect, the nucleophile is selected from a halide and a cyanide and is isotopically-labeled. In a still further aspect, the nucleophile is selected from a halide and a cyanide and is not isotopically-labeled.

In a further aspect, the nucleophile is a halide. Exemplary halides are well known by those skilled in the art and include, but are not limited to, ammonium fluoride, cesium fluoride, lithium chloride, triethylamine hydrochloride, and triethylamine hydrofluoride. In a further aspect, the nucleophile is a halide. In a still further aspect, the nucleophile is a fluoride. Exemplary of fluorides includes, but are not limited to, ammonium fluoride, cesium fluoride, triethylamine hydrofluoride, and tetrabutylammonium fluoride.

In a further aspect, the nucleophile is an isotopically-labeled amine. Exemplary isotopically-labeled amines include, but are not limited to, isotopically-labeled ammonium bicarbonate.

In a further aspect, the nucleophile is a cyanide. Exemplary cyanides include, but are not limited to, tetrabutylammonium cyanide, sodium cyanide, potassium cyanide, and acetonecyanohydrin.

In a further aspect, the catalyst system is anaerobic. Thus, in various aspects, the catalyst system is in the absence of an oxidant or an oxidizing agent. As used herein the terms "oxidant" and "oxidizing agent" refer to any species that is capable of accepting or taking electrons from another species. Exemplary oxidants are well known by those skilled in the art and include, but are not limited to, molecular oxygen, 2,2,6,6-tetramethyl-1-piperidinyloxy radical (TEMPO), ozone, and hydrogen peroxide. In a further aspect, the oxidant is molecular oxygen. In a still further aspect, the oxidant is TEMPO.

In a further aspect, the catalyst system further comprises a visible light source. In a still further aspect, the visible light source is a light-emitting diode (LED). In yet a further aspect, the visible light source has a wavelength of from about 365 nm to about 480 nm.

In a further aspect, the visible light source has a wavelength of about 415 nm, about 420 nm, about 425 nm, about 430 nm, about 435 nm, about 440 nm, about 445 nm, or about 450 nm. In various further aspect, the visible light source has a wavelength of about 425 nm.

In a further aspect, the catalyst system comprises an oxidant. Examples of oxidants include, but are not limited to, tert-butyl peroxybenzoate (TBPB), tert-butyl peroxyacetate (TBPA), benzoyl peroxide (BPO), tert-butyl hydroperoxide (TBHP), and pyridinium chlorochromate (PCC). In various further aspects, the oxidant is TBPA.

In a further aspect, the catlayst system further comprises a solvent. Examples of solvents include, but are not limited to, tertbutanol, acetonitrile, dimethyl sulfoixde, toluene, dichloromethane, tetrahydofuran, N,N-dimethylformate, 1,4-dioxane, and methanol. In various further aspects, the solvent is tertbutanol.

In a further aspect, the system further comprises a disclosed compound. In a still further aspect, the system further comprises a compound having a structure represented by a formula:

$Ar^1$-E, wherein $Ar^1$ is selected from aryl and heteroaryl and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}$($NR^{14a}R^{14b}$)$CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

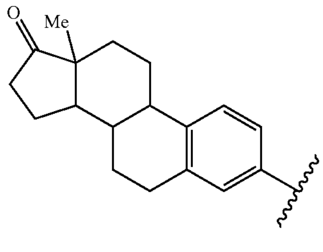;

and wherein E is an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino.

In a further aspect, the system further comprises a compound having a structure represented by a formula:

$Ar^1$-E, wherein $Ar^1$ is selected from aryl and heteroaryl and substituted with 0, 1, 2, or 3 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, and —$CH_2CR^{13}$($NR^{14a}R^{14b}$)$CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

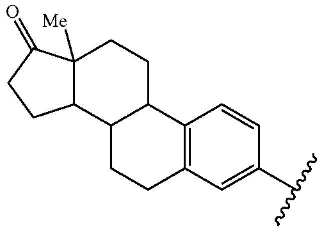

;

and wherein E is hydrogen or an electron donating group is selected from —$OR^{20}$, —$SO_3R^{20}$, —$SR^{20}$, —$NR^{21a}R^{21b}$, —OC(═O)$R^{20}$, —OC(═O)$OR^{20}$, —OC(═O)$SR^{20}$, and —OC(═O)$NHR^{20}$; wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino.

In a further aspect, the catalyst system further comprises a compound having a structure represented by a formula:

$Ar^1$-E, wherein $Ar^1$ is selected from aryl and heteroaryl and substituted with 0-6 groups independently selected from halogen, —CN, —$NO_2$, C1-C8 alkyl, C1-C8 alkoxy, —O—(C1-C8 alkyl)-$CO_2$—(C1-C8 alkyl), —C(═O)$R^{10}$, —C(═O)$OR^{11}$, —C(═O)$NR^{12a}R^{12b}$, $Ar^2$, —$OAr^2$, —C(═O)$Ar^2$, —$OR^{16}$, and —$CH_2CR^{13}$($NR^{14a}R^{14b}$)$CO_2R^{15}$; wherein each of $R^{10}$, $R^{11}$, $R^{12a}$, $R^{12b}$, $R^{13}$, and $R^{15}$, when present, is independently selected from hydrogen and C1-C4 alkyl; wherein each of $R^{14a}$ and $R^{14b}$, when present, is independently selected from hydrogen, C1-C4 alkyl, and amine protecting group; wherein $R^{16}$, when present, is a hydroxy protecting group; and wherein $Ar^2$, when present, is selected from aryl and heteroaryl and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, —O—(C1-C8 alkyl)-$CO_2$—(C1-C8 alkyl), C1-C4 hydroxy, C1-C4 thioalkoxy, C1-C4 alkylthiol, C1-C4 aminoalkyl, C1-C4 alkylamino, and (C1-C4)(C1-C4) dialkylamino; or wherein $Ar^1$ is a structure represented by a formula:

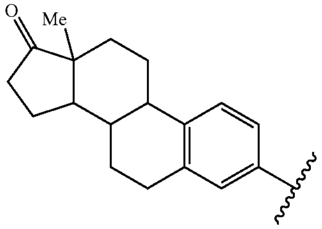

;

and

G. Wherein E is Hydrogen.Additional References

H. Teare et al., Radiosynthesis and Evaluation of [18F] Selectfluor bis(triflate). *Angew. Chem. Int. Ed.* 49, 6821-6824.

S. Preshlock, M. Tredwell, V. Gouverneur, 18F-Labeling of Arenes and Heteroarenes for Applications in Positron Emission Tomography. *Chem. Rev.* 116, 719-766 (2016).

C. N. Neumann, J. M. Hooker, T. Ritter, Concerted nucleophilic aromatic substitution with $^{19}F$ and $^{18}F^-$. *Nature.* 534, 369-373 (2016).

M. K. Narayanam, G. Ma, P. A. Champagne, K. N. Houk, J. M. Murphy, Synthesis of [18F]Fluoroarenes by Nucleophilic Radiofluorination of N-Arylsydnones. *Angew. Chem. Int. Ed.* 56, 13006-13010.

T. Gendron et al., Ring-Closing Synthesis of Dibenzothiophene Sulfonium Salts and Their Use as Leaving Groups for Aromatic 18F-Fluorination. *J. Am. Chem. Soc.* (2018), doi:10.1021/jacs.8b06730.

E. Lee et al., A Fluoride-Derived Electrophilic Late-Stage Fluorination Reagent for PET Imaging. *Science.* 334, 639-642 (2011).

E. Lee, J. M. Hooker, T. Ritter, Nickel-Mediated Oxidative Fluorination for PET with Aqueous [18F] Fluoride. *J. Am. Chem. Soc.* 134, 17456-17458 (2012).

N. Ichiishi et al., Copper-Catalyzed [18F]Fluorination of (Mesityl)(aryl)iodonium Salts. *Org. Lett.* 16, 3224-3227 (2014).

M. S. McCammant et al., Cu-Mediated C—H 18F-Fluorination of Electron-Rich (Hetero)arenes. *Org. Lett.* 19, 3939-3942 (2017).

A. V. Mossine et al., Synthesis of [18F]Arenes via the Copper-Mediated [18F]Fluorination of Boronic Acids. *Org. Lett.* 17, 5780-5783 (2015).

M. Tredwell et al., A General Copper-Mediated Nucleophilic 18F Fluorination of Arenes. Angew. Chem. Int. Ed. 53, 7751-7755.

K. J. Makaravage, A. F. Brooks, A. V. Mossine, M. S. Sanford, P. J. H. Scott, Copper-Mediated Radiofluorination of Arylstannanes with [18F]KF. *Org. Lett.* 18, 5440-5443 (2016).

H. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Introduction of Radioisotopes from Phenol Derivatives

Positron emission tomography (PET) is a powerful imaging technology used in the areas of cancer prognosis, patient screening, and treatment monitoring, as well as in drug discovery and development. Despite the exceptional promise of PET imaging, the availability of PET agents remains limited in many situations due to the lack of efficient and simple labeling methods to modify biologically active molecules/drugs. Typically, radioisotopes such as [$^{18}$F] and [$^{11}$C] are introduced via chemical reactions to modify the molecule of interest to create a radiolabeled probe molecule for PET imaging purposes. However, there are few reliable chemical transformations that allow for the introduction of these two important radioisotopes.

To address the introduction of [$^{18}$F] to molecules of interest, a direct conversion of phenol derivatives to aromatic fluorides was developed (see FIG. 1). By using a one-electron photooxidation catalyst, nucleophilic aromatic substitution ($S_N$Ar) are catalyzed. This pathway has recently been described by the Nicewicz laboratory for the addition of nitrogen heterocycles and ammonia to the methoxy-bearing carbon atom of anisole derivatives under anaerobic conditions (Tay and Nicewicz (2017) *J. Am. Chem. Soc.* 139: 16100-16104). However, this previously described catalyst system does not allow for the $S_N$Ar fluorination of methoxyarenes. Here, the direct fluorination of phenol derivatives using acridinium-based single electron photooxidation catalysts is described.

Figure 2A:
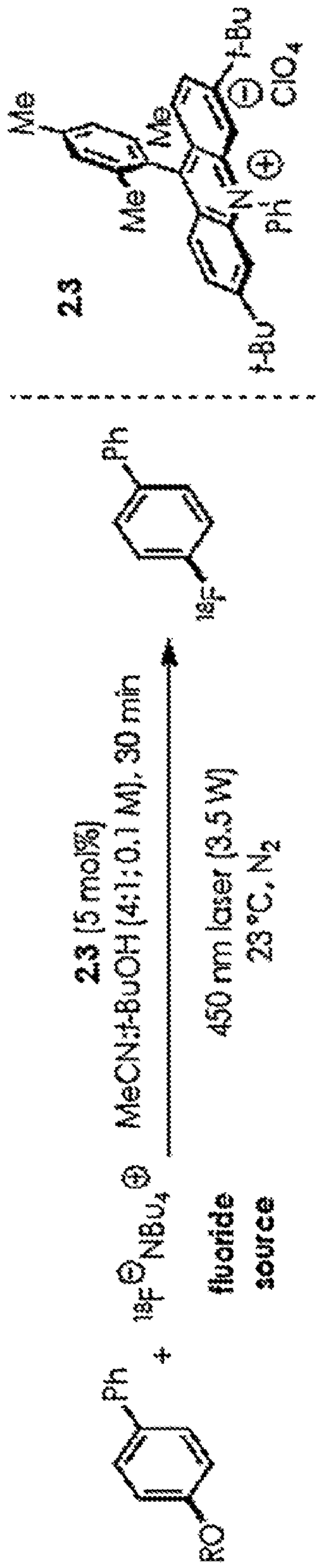
FIG. 2A-C show a representative schematic (FIG. 2A) and substrates (FIG. 2B and FIG. 2C) illustrating the [$^{18}$F] fluorination of phenol derivatives.
Figure 2B:
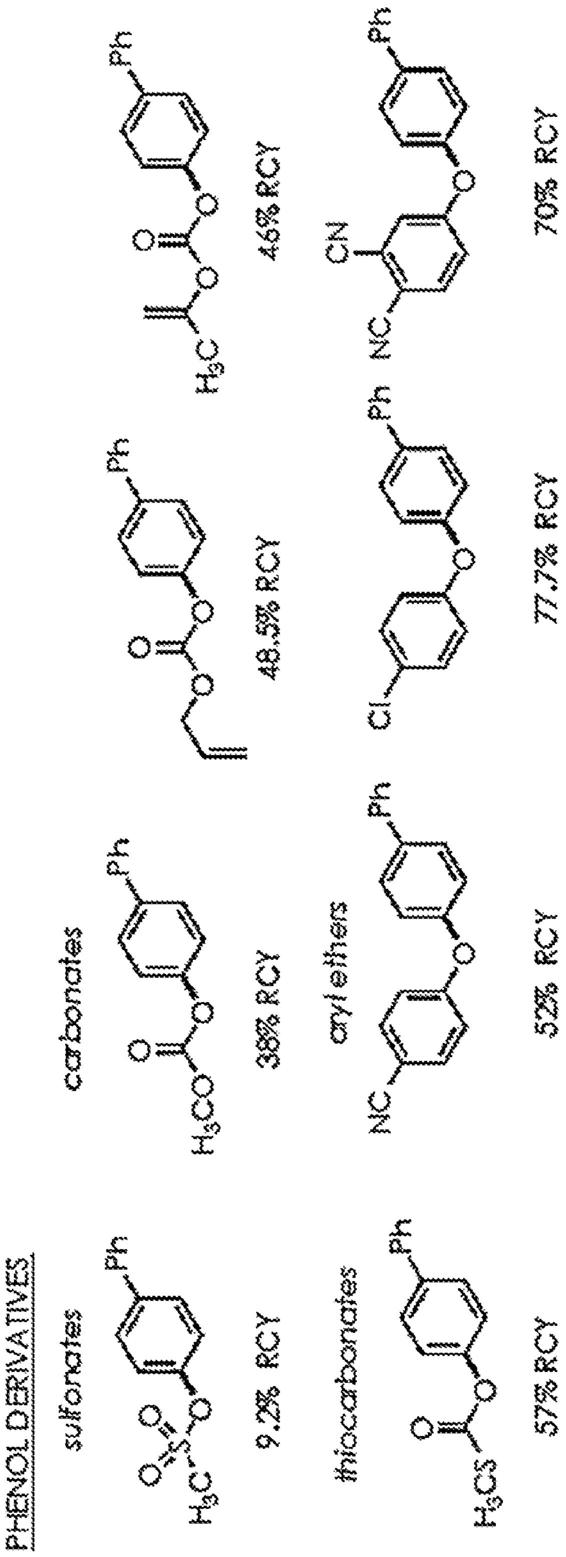
Figure 2C:
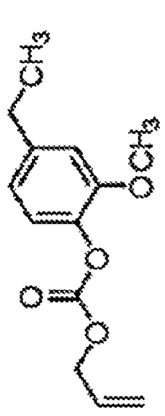
Figure 2C:
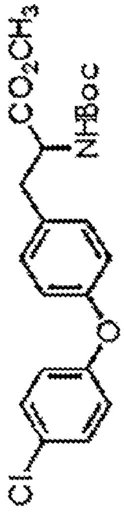
Figure 2C:
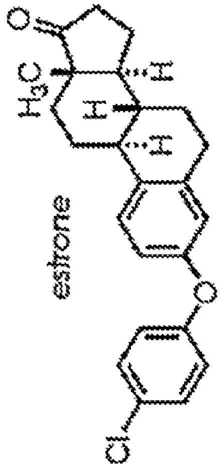

Phenol derivatives having leaving groups such as sulfonate, carbonate, thiocarbonate and phenoxy allow for direct conversion to the corresponding $^{18}$F aromatics in good to excellent isolated radiochemical yields (RCY) under inert atmospheres ($N_2$ or Ar) (FIG. 2A-2C). The highest specific activity for the $^{18}$F aromatics was obtained using the $ClO_4^-$ salt of catalyst 2.3. Biologically-relevant molecules such as tyrosine and estrone can be readily converted to the $^{18}$F derivatives as well in good RCYs.

Figure 3:
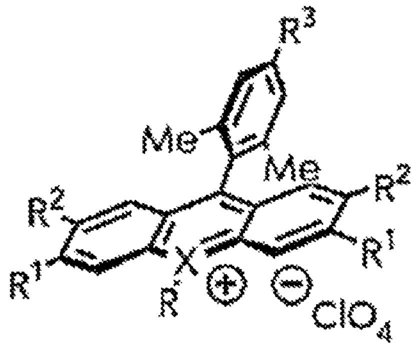
FIG. 3 shows representative organic photoredox catalyst structures.

A list of other potential catalyst structures that could be applied to this transformation is found in FIG. 3. The parent acridinium salt (2.1) is a potent single electron photooxidant ($E_{p/2}$=+1.87 V vs. SCE) as both the locally excited singlet (LEs) and charge transfer triplet (CTT) excited states are highly oxidizing at +2.18 and +1.88 V vs. SCE, respectively (FIG. 3) (Fukuzumi et al. (2004) *J. Am. Chem. Soc.* 126: 1600-1601; Fukuzumi et al. (2014) *Acc. Chem. Res.* 47: 1455-1464; Benniston et al. (2005) *J. Am. Chem. Soc.* 127: 16054-16064; Benniston et al. (2008) *Phys. Chem. Chem. Phys.* 10: 5156-5156). During the course of working with these privileged structures, many useful observations have been made concerning derivatization of these oxidizing salts. For example, alteration of the aromatic group on the 9-position of the acridinium salts greatly impacts the identity of the excited state in the molecule that can either populate locally-excited or charge transfer states and either short-lived singlet or long-lived triplet states (Romero and Nicewicz (2014) *J. Am. Chem. Soc.* 136: 17024-17035). In addition, the acridinium ring itself most directly impacts the reduction potential of the catalyst, wherein introduction of electron withdrawing groups aids in ease of reduction. This effect can be seen in the $E_{1/2}^{red}$ and $*E_{1/2}^{red}$ for acridinium derivatives listed in FIG. 3. Lastly, insulating the most electrophilic positions (i.e., positions 3 and 6) of the acridinium ring is crucial to catalyst stability. The introduction of tert-butyl groups in the 3 and 6 positions results in a more robust catalyst (2.3) that can now coexist in solution with potent nucleophiles, greatly enhancing the range of possible transformations. Importantly, inclusion of these “blocking groups” does not have a substantial effect on the redox properties of the catalyst (c.f. 2.3 with 2.4). The more oxidizing xanthenylium catalysts, such as the parent 9-mesityl xanthenylium salt (2.7), have excited state reduction potentials as high as +2.79 V vs. SCE and would be useful in the context of more electron deficient substrates.

Figure 4A:
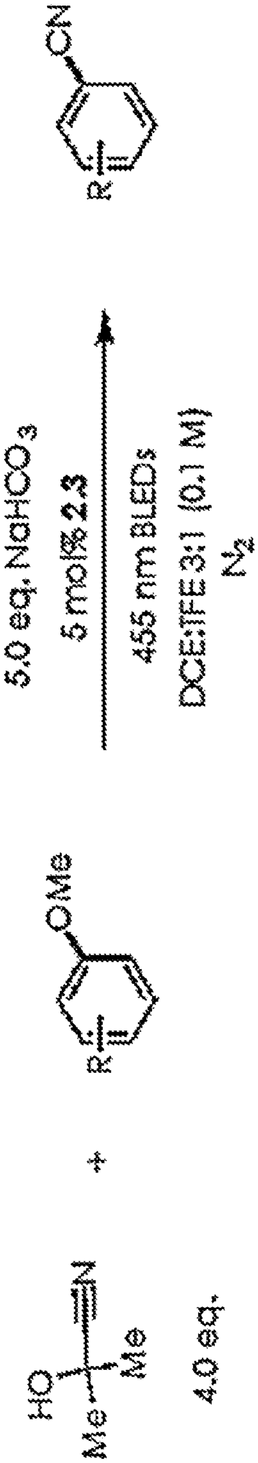
FIG. 4A shows a representative schematic and FIG. 4B shows representative substrates illustrating the preliminary reaction scope of direct $S_NAr$ cyanation reaction.
Figure 4B:
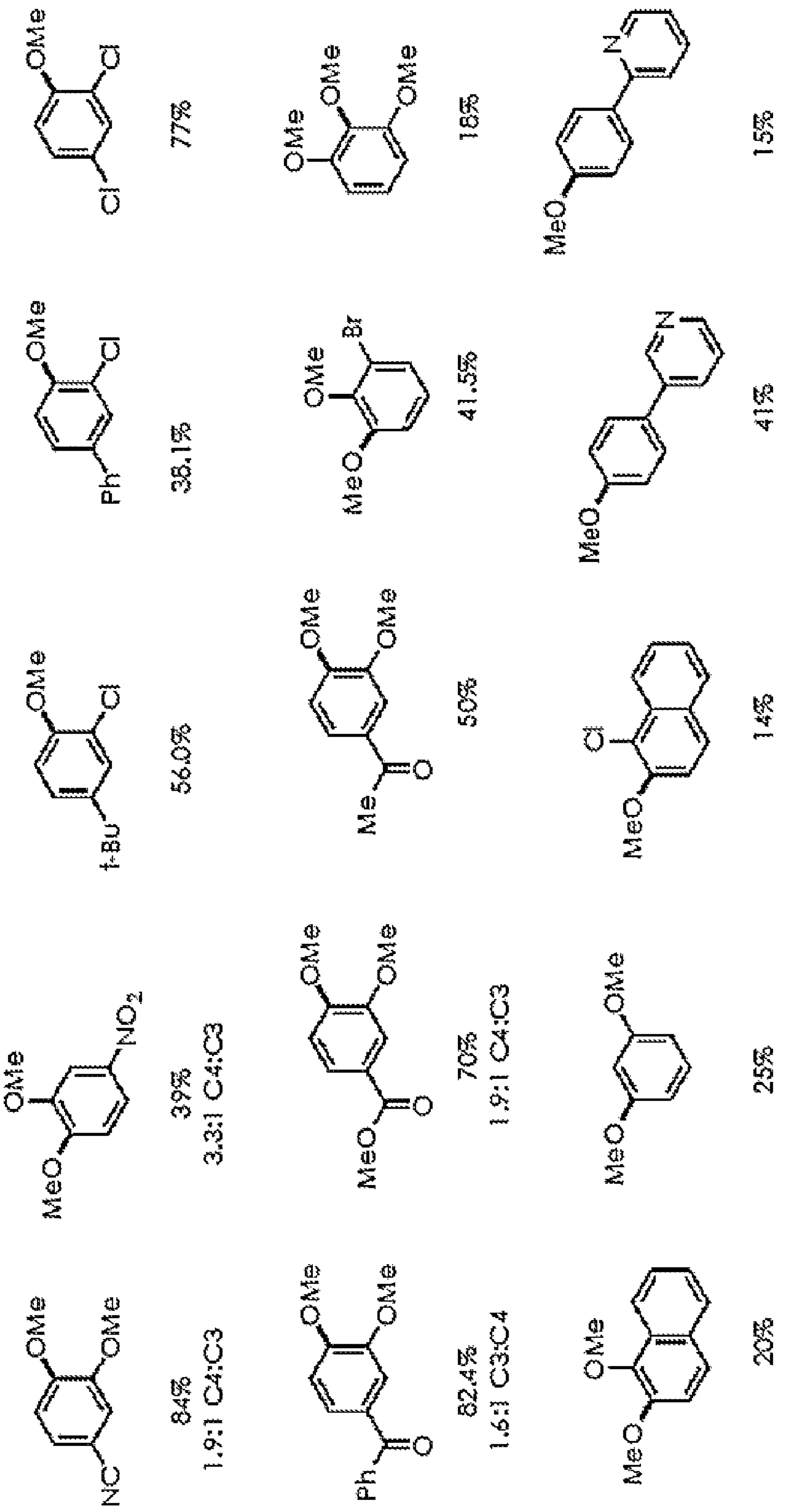

In addition to [$^{18}$F]fluorination, preliminary data regarding the introduction of cyanide is found in FIG. 4A and FIG. 4B. Using either tetrabutylammonium cyanide or acetonecyanohydrin (depicted) as the reagent, a range of methoxyarene derivatives readily undergo conversion of the methoxy group to the cyano group. By employing either [$^{11}$C]cyanide or [$^{11}$C]acetonecyanohydrin, this method can be further elaborated to generate [$^{11}$C]cyanide adducts, as well. This would be a significant deviation from prior art in this area where [$^{11}$C]cyanide has been used to make [$^{11}$C] cyanoaromatics from the corresponding aryl halides (Lee et al. (2015) *J. Am. Chem. Soc.* 137: 648-651).

Figure 5:
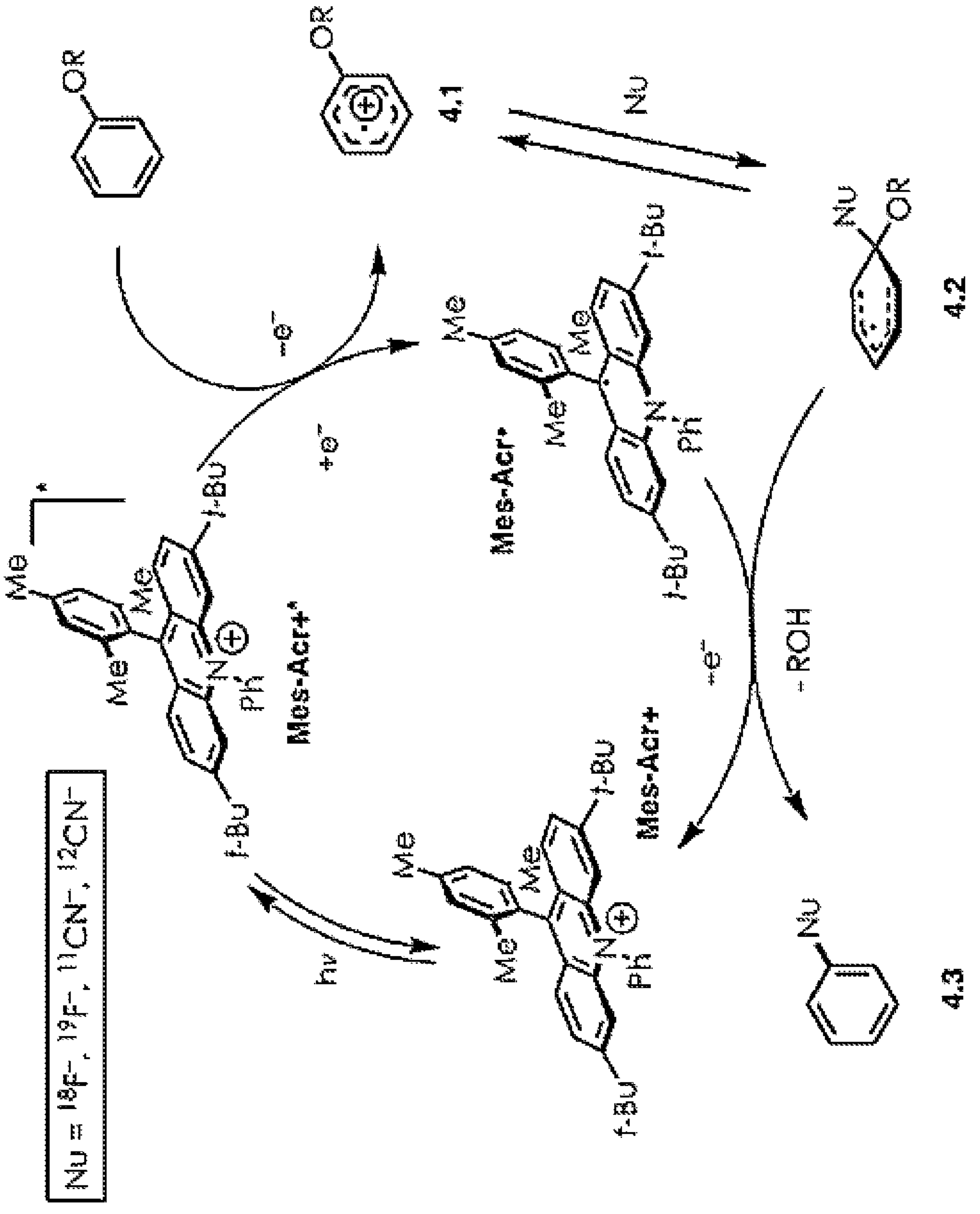
FIG. 5 shows a representative schematic of a proposed mechanism.

A general mechanism proposed for these transformations is found in FIG. 5. Excitation of the acridinium catalyst (Mes-Acr+) by a blue photon results in the formation of the powerful excited state photooxidant (Mes-Acr+*). This excited state then oxidizes the phenol derivative to lead to the formation of reactive cation radical 4.1. This intermediate is susceptible to addition by the nucleophile (Nu) to lead to Meisenheimer-like intermediate 4.2. After loss of the alkoxy group and gain of an electron from the reduced form of the catalyst (Mes-Acr•), the final $S_N$Ar adduct (4.3) is obtained.

2. Development of a Direct Arene C—H $^{18}$F-Fluorination

An investigation to develop a direct arene C—H $^{18}$F-fluorination was initiated to address the following challenges: (1) the fluorination should not need direction groups or complicated synthesis of special precursor; rather, existing drug molecules should be used with no or minimal modification for labeling reaction; (2) the $^{18}$F-fluoride source should be readily available as F− instead of F+ and the resulting agent should have high specific activity; (3) the reaction conditions should be mild and the reaction rate should be done within an hour considering the short half-life of $^{18}$F; (4) the reaction system may not involve a metal catalyst, to simplify the quality control process in future translation. Inspired by recent progress on organic photoredox catalysis, net C—H to C—F bond conversion was focused on using visible light mediated oxidative C—H fluorination.

Figure 6:
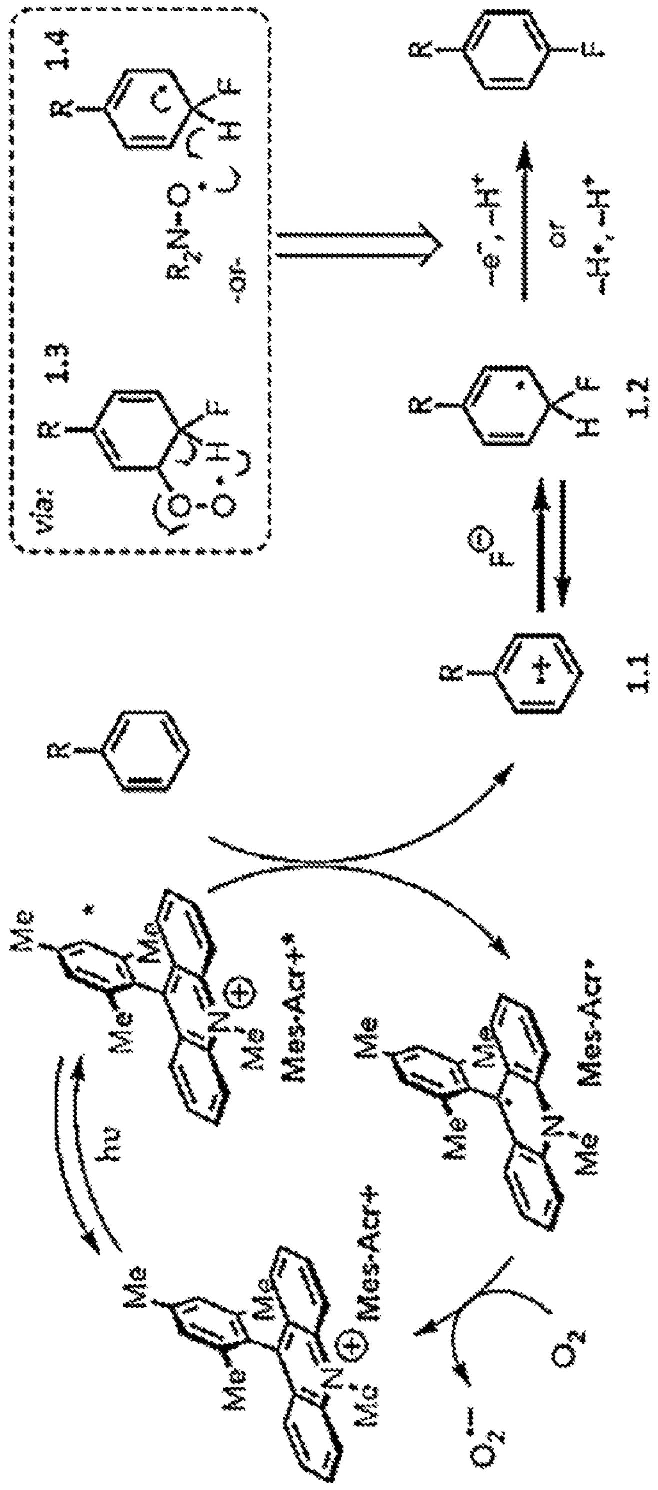
FIG. 6 shows a representative schematic of a proposed arene C—H fluorination mechanism.

The mechanistic proposal begins with single electron oxidation of the arene by the excited state of the photocatalyst (Mes-Acr+*), after which the arene cation radical (1.1) can be intercepted by an amine or alcohol present in solution, leading to the formation of radical 1.2 (FIG. 6). The exact nature of the following oxidation is perhaps less clear, however, $O_2$ is presumed to react with cyclohexadienyl radicals to lead to alkylperoxyl radicals (1.3). Elimination of radicals of type 1.3 to give the corresponding aromatics is slow, (ca. $10^3$ $s^{-1}$) compared to the reaction of $O_2$ with the cyclohexadienyl radicals (ca. $10^8$ $M^{-1}$ $s^{-1}$) and are often accompanied by unwanted hydrogen atom abstraction pathways. Nitroxyl radicals, the archetypal example, 2,2,6,6-tetramethyl-1-piperidine 1-oxyl (TEMPO), react rapidly (>$10^8$ $s^{-1}$) with cyclohexadienyl radicals via hydrogen atom abstraction to yield the corresponding aromatic compounds (1.4). The C—H bond enthalpies for cyclohexadienyl radicals have been estimated at approximately 50 kcal $mol^{-1}$, whereas the O—H bond enthalpy for TEMPO-H has been assessed at 70 kcal $mol^{-1}$. This raises the prospect for employing nitroxyl radicals as co-catalysts in the proposed transformations as the reoxidation of TEMPO-H to TEMPO by $O_2$ is facile.

Figure 7:
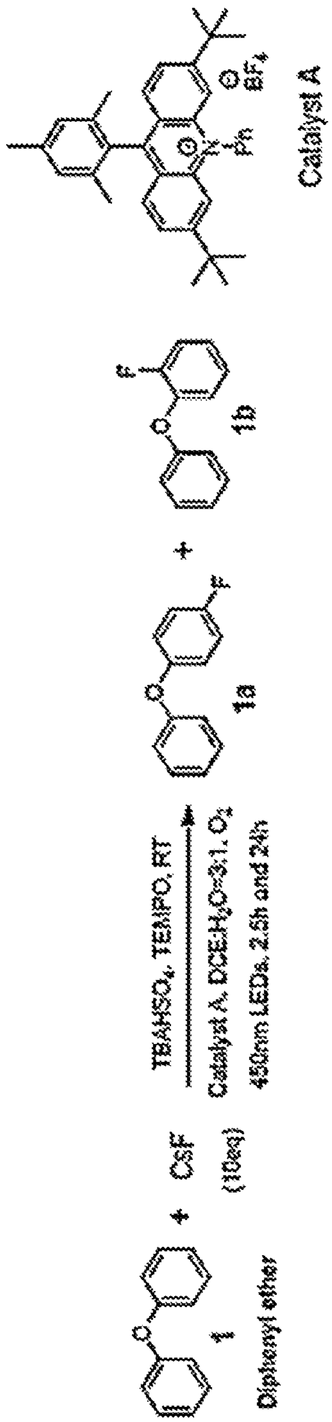
FIG. 7 shows a representative schematic of the direct C—F fluorination of arenes.

The initial test involved a modified photo redox system previously used in oxidative C—H amination and cyanation reactions (FIG. 7). Diphenyl ether (0.05 mmol) was chosen as the model substrate to explore the photo-fluorination considering its lower volatility and it popularity in drug skeletons. For "cold" (i.e., not radioactive) fluorination reactions, both CsF and TBAF (1 M in THF) were selected as $^{19}F^-$ sources, A was chosen as the photo catalyst, 20 W 450 nm LED light was used as light source. A variety of solvents, phase transfer agents, and temperatures were explored. After preliminary screening, it was discovered that the use of 5% photocatalyst A, 50% of TEMPO, DCE/$H_2O$ as the solvent, $TBAHSO_4$ as phase transfer agent, oxygen gas as the oxidant, along with 24 h 450 nm LED light irradiation at room temperature, could lead to fluorinated diphenyl ether in 17% yield with 13:1 p- to o-ratio.

With these encouraging results on hand, the labeling conditions were extended to no-carrier-added $^{18}F—F^-$. Unfortunately, no radiolabeled product was detected after extensive attempts. The major difference between radiolabeling and "cold" reaction are concentration and reaction ratio. In labeling reactions, high specific activity $^{18}F$ are in trace amount (~1-10 μM compared with ~100 mM range of $^{19}F$ in cold reaction). At "cold" labeling reaction, $^{19}F—F^-$ is 10 times more than diphenyl ether vs. large excess amount of diphenyl ether to $^{18}F—F^-$ in labeling reactions.

Clearly, with a good starting point in "cold" reaction, the labeling conditions for C—H to C-$^{18}F$ direct conversion must be re-optimized. In fact, 24 h light irradiation is another barrier that must be overcome: due to the short half-life of $^{18}F$ (110 min), a practical labeling reaction may need to be finished within an hour. Different fluoride source with various counterions were evaluated as shown in Table 1.

TABLE 1

| Entry | $^{18}F$-Fluoride | Isolated yield of 1a[a] | Isolated yield of 1b[a] |
|---|---|---|---|
| 1 | $^{18}F$-CsF (First Method: $^{18}F$ on QMA was eluted with 0.9% CsCl) | Trace | Nd |
| 2 | $^{18}F$-CsF (Second Method: $^{18}F$ on QMA was eluted with 0.9% $Cs_2CO_3$) | nd | Nd |
| 3 | $^{18}F$-CsF (Third Method: $^{18}F$ on QMA was eluted with 0.9% CsF) | nd | Nd |
| 4 | $^{18}F$-CsF (Fourth Method: [$^{18}F$]TBAF mixed with CsCl) | nd | Nd |
| 5 | $^{18}F$-CsF (Fifth Method: [$^{18}F$]TBAF mixed with CsF) | nd | Nd |
| 6 | $^{18}F$-TBAF | 0.572% | trace |
| 7 | $^{18}F$-KF ($^{18}F$ on QMA was eluted with 0.9% $KClO_4$) | nd | nd |
| 8 | K[$^{18}F$]F-kryptofix | 0.39% | trace |

[a]nd = not detected

After removing $TBAHSO_4$ from the system, $^{18}F$—CsF lead to trace amounts of product (<0.1%). When anhydrous $^{18}F—F^-$ was used, the yield could be increased to 0.57% for $^{18}F$-TBAF or 0.39% for K[$^{18}F$]—F-kryptofix after 2.5 h light irradiation. Notably, isolation yield was used in all reports, rather than radio-TLC- and radio-HPLC-integration determined yields: due to the nonspecific binding of $^{18}F$—F-toward injector, lines, or columns, a 30% isolation reaction may have more than 40% yield determined by radio-TLC. Unreacted $^{18}F$ does not always show consistent radio-HPLC peaks, which results in an unreasonably higher yield by the integration radio-HPLC. The isolation yields are also more instructive on the application of the tracer synthesis (also, the small impurity or byproduct, which is very close to the product on the HPLC, cannot be completely separated by radio-TLC).

$^{18}F$-[TBAF] was then choose as the fluorine sauce to do the further exploration and the next effort focused on shortening the reaction time by increase light intensity. A light tunnel was first build with four LED strips and the reaction was performed a thin transparent line. Alternatively, the light source could be a laser, LED light, up-conversion particles, x-ray particles, chemofluorescence, or bioluminescence. Additional examples of reaction vessels that can be used include, but are not limited to, a vial, a flask, a thin polymer line for flow, and a thin glass/polymer film. Although the yield was increased to only 1.23% with 2.5 h irradiation, it did indicate intensity play a key role in accelerating fluorination reaction. Instead of using LED lights, a blue diode laser coupled with optical fiber was then used to boost the reaction. With acetone/ice cold bath, it was observed that the isolation yield jumped to 28.6% after 2.5 h irradiation (Table 2, entry 4).

Referring to Table 2, the C—H to C-$^{18}F$ direct conversion protocol was further optimized. As shown in entries 5-9, the fluorination proceed gradually over time and isolation yield is 2.67% after 0.5 h irradiation for these new conditions. Further increasing the laser power to 3.5 w tripled the yield to 8.23% at 0.5 h (entry 10). However, the yield at 2 h is slightly lower than at the 1 w condition, which could be mainly caused by the depletion of catalyst at high power condition. Considering the short half-life of $^{18}F$ (~110 min), conditions with 0.5-1 h irradiation time were primarily focused on. Doubling the catalyst loading to 10% did not significantly change the labeling yield (entries 15-16). Interestingly, bubbling the oxygen, rather than just stationary contact into the reaction solution, boosted the yield to 25.84 with only 0.5 h laser irradiation. Changing oxygen to nitrogen significantly decreased the yield (i.e., to 2.79%), suggesting that oxygen could greatly facilitate C—H bond fluorination. Additional conditions such as in the absence of TEMPO and the addition of water did not quench the reaction, but significantly decreased its yield (Table 2).

TABLE 2

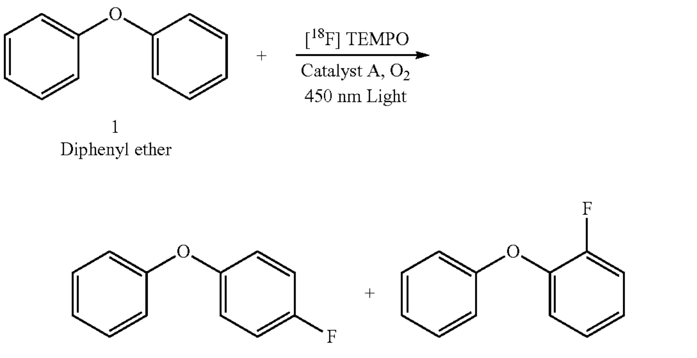

1
Diphenyl ether 1a 1b

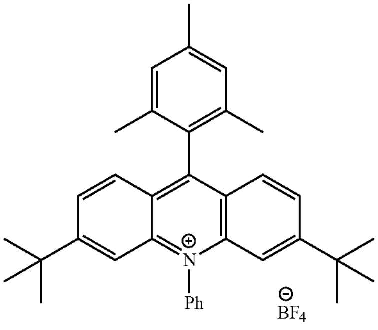

Catalyst A

| Entry | Solvent | $^{18}F$ Source | Temp | Light Source (450 nm) | Time | Gas | RCY yield of 1a; and 1b |
|---|---|---|---|---|---|---|---|
| 1 | $DCE/H_2O$ (3:1) | CsF | rt | LED lamp | 2.5h | $O_2$ | trace; nd |
| 2 | $CH_3CN$ | TBAF | rt | LED lamp | 2.5h | $O_2$ | 0.572%; trace |
| 3 | $CH_3CN$ | TBAF | 0° C. | LED Strips | 2.5h | $O_2$ | 1.23%; trace |
| 4 | $CH_3CN$ | TBAF | 0° C. | Laser(1W) | 2.5h | air | 28.6%; 1.3% |
| 5 | $CH_3CN$ | TBAF | 0° C. | Laser(1W) | 0.5h | air | 2.67%; trace |
| 6 | $CH_3CN$ | TBAF | 0° C. | Laser(1W) | 1h | air | 7.68%; 0.64% |
| 7 | $CH_3CN$ | TBAF | 0° C. | Laser(1W) | 1.5h | air | 11.98%; 1.60% |
| 8 | $CH_3CN$ | TBAF | 0° C. | Laser(1W) | 2h | air | 19.38%; 1.78% |
| 9 | $CH_3CN$ | TBAF | 0° C. | Laser(1W) | 2.5h | air | 25.74%; 2.64% |
| 10 | $CH_3CN$ | TBAF | 0° C. | Laser (3.5W) | 0.5h | air | 8.23%; 0.24% |
| 11 | $CH_3CN$ | TBAF | 0° C. | Laser (3.5W) | 1h | air | 12.44%; 0.90% |
| 12 | $CH_3CN$ | TBAF | 0° C. | Laser(3.5W) | 1.5h | air | 16.20%; 1.39% |
| 13 | $CH_3CN$ | TBAF | 0° C. | Laser(3.5W) | 2h | air | 19.16%; 1.70% |
| 14 | $CH_3CN$ | TBAF | 0° C. | Laser(3.5W) | 2.5h | air | 20.40%; 2.04% |
| 15 b | $CH_3CN$ | TBAF | 0° C. | Laser(3.5W) | 0.5h | air | 8.78%; 0.20% |

TABLE 2-continued

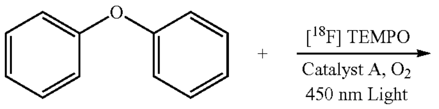

1
Diphenyl ether

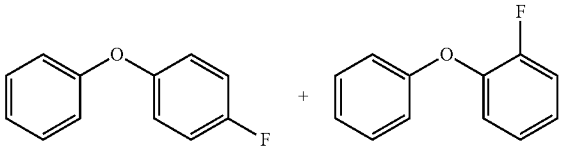

1a 1b

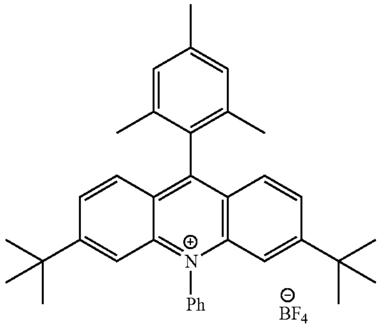

Catalyst A

| Entry | Solvent | $^{18}F$ Source | Temp | Light Source (450 nm) | Time | Gas | RCY yield of 1a; and 1b |
|---|---|---|---|---|---|---|---|
| 16 b | $CH_3CN$ | TBAF | 0° C. | Laser(3.5W) | 1h | air | 15.60%; 0.82% |
| 17c | $CH_3CN$ | TBAF | 0° C. | Laser(3.5W) | 0.5h | air | 5.96%; 0.13% |
| 18 c | $CH_3CN$ | TBAF | 0° C. | Laser(3.5W) | 1h | air | 8.07%; 0.62% |
| 19d | $CH_3CN$ | TBAF | 0° C. | Laser(3.5W) | 0.5h | O2 | 25.84%; 2.01% |
| 20 | $CH_3CN$ | TBAF | 0° C. | Laser(3.5W) | 0.5h | N2 | 2.79%; trace |

a. All the reactions conduced with 0.05 mmol of 1 (0.1M); 5 mmol% catalyst and 50 mmol% TEMPO without other noted.

b. 10 mmol% catalyst c.1 eq TEMPO d.$O_2$ bubbling

Figure 8:
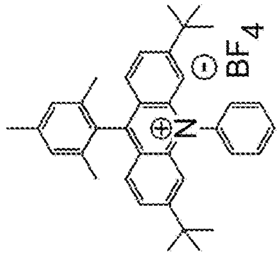
FIG. 8 shows representative catalyst structures.
Figure 8:
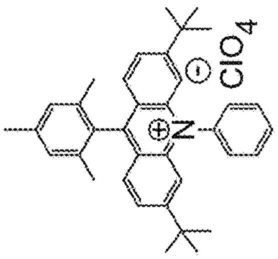
Figure 8:
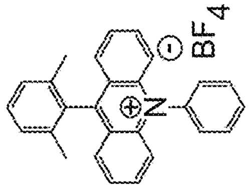
Figure 8:
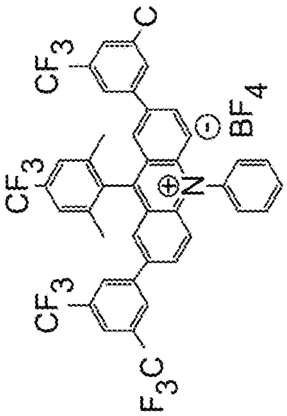
Figure 8:
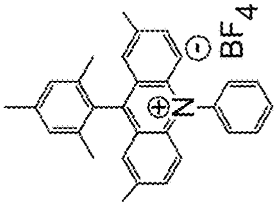
Figure 8:
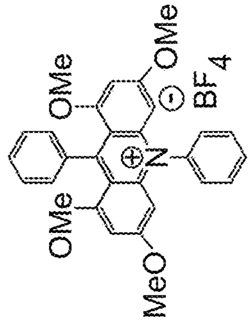
Figure 8:
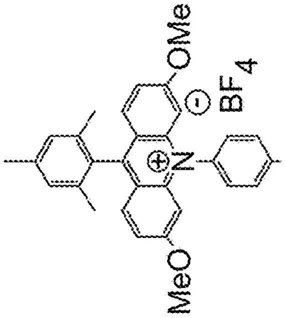
Figure 8:
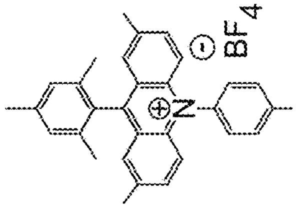
Figure 8:
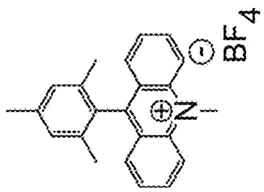
Figure 8:
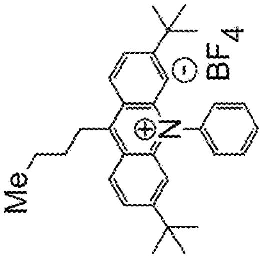
Figure 8:
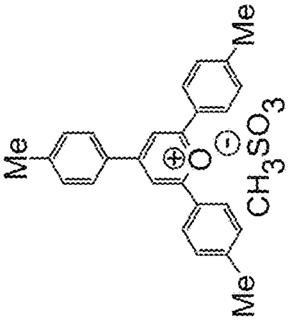
Figure 8:
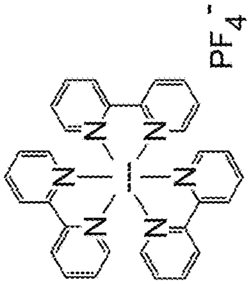
Figure 9:
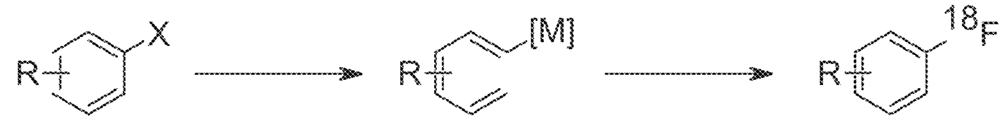
FIG. 9 shows a representative schematic illustrating direct C—H radiofluorination through LED illuminated photocatalysis.
Figure 9:
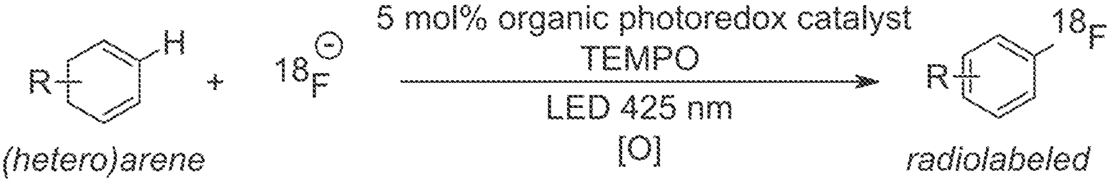
Figure 9:
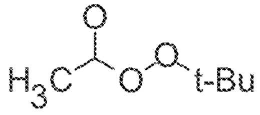
Figure 9:
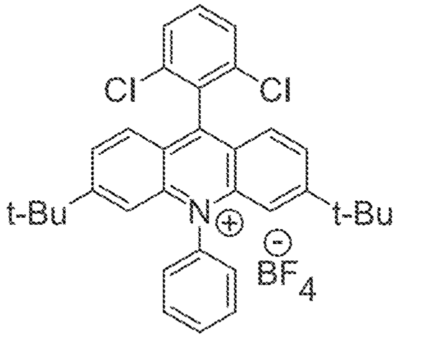

A series of acridinium organic photoredox catalysts were screened under the optimized conditions (FIG. 8). Catalyst A was found still the most efficient catalyst among other tested organic acridinium salts. The catalyst L and K $Ru(bpy)_3(PF_6)_2$ didn't result in detectable radiolabeled product. Reaction solvent systems were then screened using A as the catalyst. As shown in Table 3, neither DMSO, DMF, nor MeOH led to any detectable product. THF only gave a trace amount of product 1. DCE gave about 9% product. Surprisingly, addition of t-BuOH (400 μl) as the co-solvent with MeCN (100 μl) further improved the isolation yield to 37.1±12% (n=4). When pure t-BuOH was used as the solvent, only 2% of 1 was separated. In fact, t-BuOH was previously found to facilitate fluorination reactions previously. Decreasing the concentration of the diphenyl ether or the catalyst loading reduced the isolation yield, as expected (Table 3).

TABLE 3

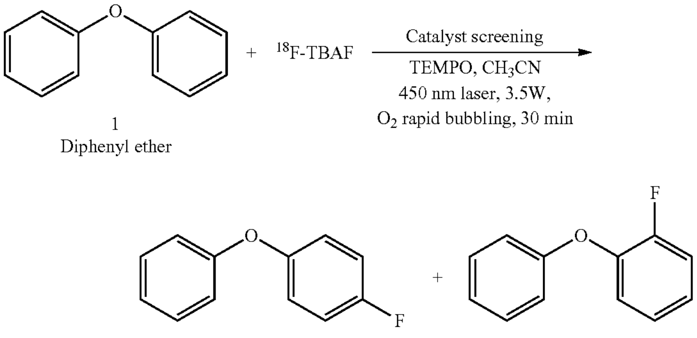

1
Diphenyl ether 1a 1b

| Entry | Catalyst | Isolated yield of 1a[a] | Isolated yield of 1b[a] |
|---|---|---|---|
| 1 | A | 25.84% | 2.01% |
| 2 | C | 0.92% | nd |
| 3 | D | 0.11% | nd |
| 4 | E | 5.44% | 0.60% |
| 5 | F | nd | nd |
| 6 | G | nd | nd |
| 7 | H | 12.70% | 0.64% |
| 8 | I | 7.39% | trace |
| 9 | J | nd | nd |
| 10 | K | nd | nd |
| 11 | L | nd | nd |

In addition, the specific activity of the compound produced was determined. Because a comparable yield could be obtained using catalyst A and either $ClO_4^-$ or $BF_4^-$ as the counterpart, the $ClO_4^-$ catalyst was focused on to avoid unnecessary introduction of a source of $^{19}$F to the reaction system. Indeed, $^{18}$F-1 was obtained with 1.37 Ci/μmol specific activity. It was later found that by using the laser irradiation reaction conditions, simply changing $^{18}$F-TBAF back to $^{18}$F—CsF using tBuOH as the only solvent also gave 1 in 21.2% yield and 2 in 0.8% yield. 26.2% 1 and 1.5% 2 was also isolated when K[$^{18}$F]F-kryptofix was used instead of TBAF under the optimized laser reaction conditions.

Having demonstrated that organic photoredox catalysis can efficiently radiofluorinate C—H bonds in a diphenyl ether directly using $^{18}$F—$F^-$ under mild conditions within 30 min, this reaction was then expanded to a variety of electron rich aromatics. The p-position C—H bond in biphenol substrate was efficiently fluorinated to C-[$^{18}$F]F bond in 44.2% isolation yield in 30 min. The C—H bond in naphthalene could also be radiofluorinated quickly at position 1 with 20.9% isolation yield. Mesitylene gave only a moderate yield with 30 min irradiation using the above conditions. However, a slightly modified photoredox condition (2 eq. TEMPO and replacing oxygen flow with nitrogen flow) successfully boosted the isolation yield to 50% with 30 min of light irradiation for the optimization).

Alkoxy-containing aromatic rings are one of the most common motifs in bioactive compounds. Without further optimization, the catalyst system was evaluated for the quick, direct conversion of Ar C—H bonds to C-[$^{18}$F]F (Table 4). Moderate isolation yields were obtained for 1-bromo-2-methoxybenzene with 30 min light irradiation (9.2%, fluorinate p-C—H of the methoxy group). The fluorination position agrees well with previous calculation studies, suggesting that the p-position of the MeO group would be a favorable site for the nucleophilic reaction. Similarly, the isolation yields were 15.1% and 11.1% after replacing Br with Cl and cyano groups, respectively (30 min irradiation). Further study demonstrated that the C—H to C—F bond conversion is slightly more efficient when the methoxy group is coupled with an electron-withdrawing functional group such as, for example, amide 10, ketone 8, ester 9, and aldehyde 11 groups (the isolation yields were 13.8%, 24.6%, 23.5%, and 22.4%, respectively). The C—H fluorination was also achieved in methoxy- and TfO- di-substituted substrates, with 27.7% isolation yield after 30 min of light irradiation. Notably, the Br and OTf substituted substrates may not tolerate transition-metal-mediated $^{18}$F-fluorinatioin. Arene substrates corresponding to products no. 13 and 14 were also tested using this light redox system. Moderate isolation yields (i.e., yields of 7.0% and 4.1%) were achieved, which could mainly be due to the poor solubility of these solid substrates in the tBuOH/MeCN solvent system. Nevertheless, these separated yields are still acceptable for PET imaging applications. Trisubstitution substrates corresponding to product nos. 15 and 16 were also successfully fluorinated in 34.3% and 13% yield with just 0.5 h irradiation, which, without wishing to be bound by theory, can be very useful in the synthesis of more complicated tracers or building blocks.

TABLE 4

| No. | Structure | Yield |
|---|---|---|
| 1 | 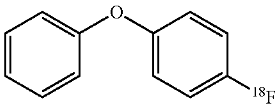 [SMILES: [18F]c1ccc(Oc2ccccc2)cc1] | 38.2 ± 10% (n = 5) |
| 2 | 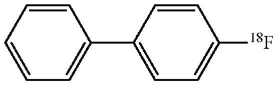 | 44.2 ± 12% (n = 3) |

TABLE 4-continued

| No. | Structure | Yield |
|---|---|---|
| 3 | 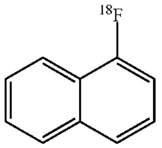 [SMILES: [18F]c1cccc2ccccc12] | 20.9 ± 1% (n = 3) |
| 4 | 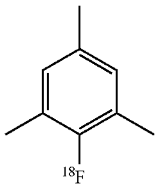 | 50 ± 11% (n = 3) |
| 5 | 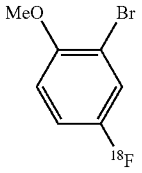 | 9.2 ± 0.5% (n = 3) |
| 6 | 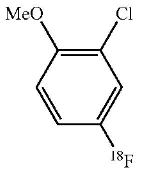 | 15.1 ± 1% (n = 3) |
| 7 | 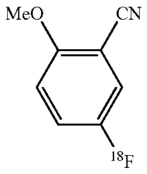 [SMILES: COc1ccc([18F])cc1C#N] | 11.1 ± 2% (n = 3) |
| 8 | 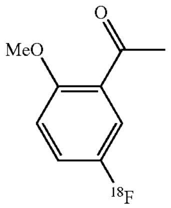 | 24.6 ± 2% (n = 3) |
| 9 | 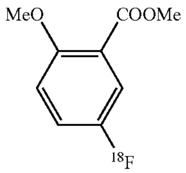 [SMILES: COC(=O)c1cc([18F])ccc1OC] | 23.5 ± 5% (n = 3) |
| 10 | 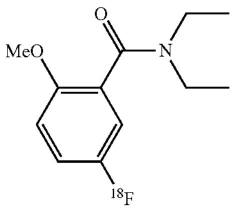 [SMILES: CCN(CC)C(=O)c1cc([18F])ccc1OC] | 13.8 ± 1% (n = 3) |
| 11 | 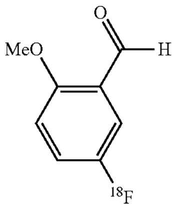 | 22.4 ± 5% (n = 3) |
| 12 | 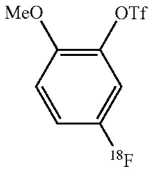 | 27.7 ± 5% (n = 3) |
| 13 | 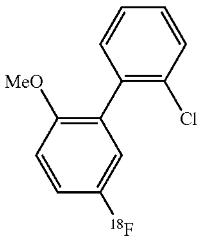 [SMILES: COc1ccc([18F])cc1-c1ccccc1Cl] | 7.0 ± 3% (n = 3) |
| 14 | 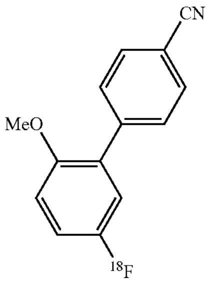 [SMILES: COc1ccc([18F])cc1-c1ccc(C#N)cc1] | 4.1 ± 0.6% (n = 3) |
| 15 | 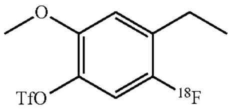 [SMILES: CCc1cc(OC)c(OS(=O)(=O)C(F)(F)F)cc1[18F]] | 34.3 ± 5% (n = 3) |
| 16 | 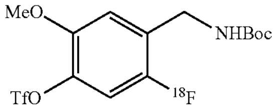 [SMILES: COc1cc(CNC(=O)OC(C)(C)C)c([18F])cc1OS(=O)(=O)C(F)(F)F] | 13% ± 3 (n = 3) |

The o-position C—H was also directly $^{18}F$-fluorinated when the p-position of methoxybenzene was occupied by electron withdrawing groups (Table 5). The substrates corresponding to aldehyde 17, ketone 18, ester 19, and amide 20 gave the o-position labeled RCY in 5.7%, 10.5%, 8.3%, and 3.9% isolation yield with 30 min light irradiation. The 1-(3-methoxyphenyl)ethanone having as substituent meta to the MeO group was also successfully labeled and provided a mixture of 21 and 22, which were easily separated and confirmed with the $^{19}F$-standard in 7.8±0.9% and 14.8±0.6% RCY yield, respectively. Compound no. 22 was the major product.

TABLE 5

| No. | Structure | Yield |
|---|---|---|
| 17 | 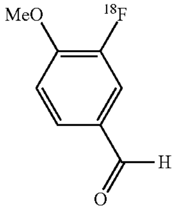 [SMILES: COc1ccc(C=O)cc1[18F]] | 5.7 ± 1% (n = 3) |
| 18 | 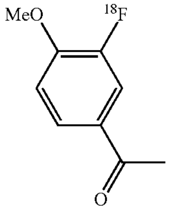 | 10.5 ± 1% (n = 3) |
| 19 | 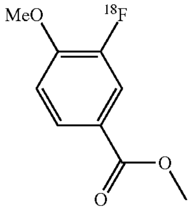 | 8.3 ± 4% (n = 3) |
| 20 | 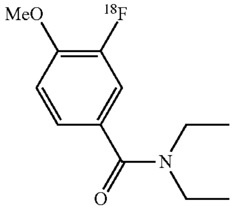 [SMILES: CCN(CC)C(=O)c1ccc(OC)c([18F])c1] | 3.9 ± 0.9% (n = 3) |
| 21 | 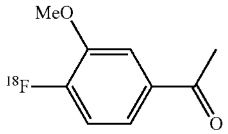 | 7.8 ± 0.9% (n = 3) |
| 22 | 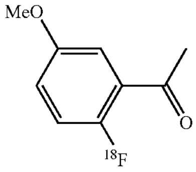 | 14.8 ± 0.6% (n = 3) |

Overall, these results demonstrate that the disclosed photo redox system is compatible with various functional groups commonly seen in bioactive molecules. Both p- and o-Ar C—H bond were directly fluorinated.

The photo redox C—H fluorination system was also tested in the heterocyclic compound quinazolinedione, which was fluorinated at the position para to the nitrogen atom in 17.9% isolation yield after 30 min (Table 6, no. 23). The 3,5-dimethoxypyridine was selectively labeled on the 2-position of pyridine ring in 11.1% RCY. Substituted quinoline was labeled at the 5-position as the major product in 6.0% yield. Direct fluorination of 1-methyl indazole was also successful (14.4% isolation yield with 30 min irradiation) and the major fluorinated site is 3. Clearly, the disclosed method also holds great potential for the direct fluorination of C—H bonds in heterocyclic compounds, as well.

TABLE 6

| No. | Structure | Yield |
|---|---|---|
| 23 | 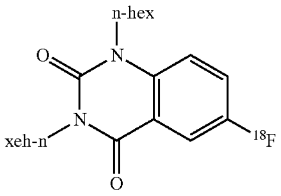 | 17.9 ± 2% (n = 3) |
| 24 | 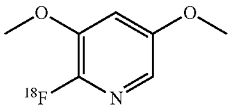 | 11.1 ± 2% (n = 3) |
| 25 | 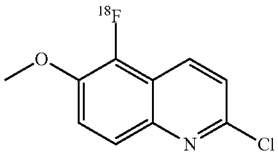 | 6.0 ± 0.6% (n = 3) |
| 26 | 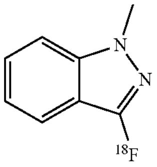 | 14.4 ± 3% (n = 3) |
| 27 | 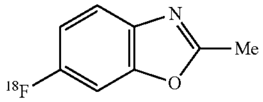 [SMILES: Cc1nc2ccc([18F])cc2o1] | 7.1 ± 0.5% (n = 3) |
| | 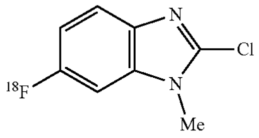 [SMILES: Cn1c(Cl)nc2ccc([18F])cc21] | 11.1 ± 1% (n = 3) |

Lastly, the disclosed photo redox system was evaluated in bioactive molecules (Table 7). The methyl ester of Fenprofen X and Flurbiprofen X (nonsteroidal anti-inflammatory drugs, NSAIDs) were primarily labeled at the unsubstituted phenyl ring in 39.6% and 36.8% isolation yield with 30 min irradiation. Clofibrate, a lipid-lowering agent used for controlling high cholesterol and the level of triacylglycerides in the blood, was labeled at the o-position of the alkoxy group in 3.7% yield.

TABLE 7

| No. | Structure | Yield |
|---|---|---|
| 28 | 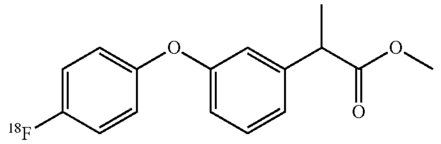 [SMILES: COC(=O)C(C)c1cccc(Oc2ccc([18F])cc2)c1] | 39.6 ± 1% (n = 3) |
| 29 | 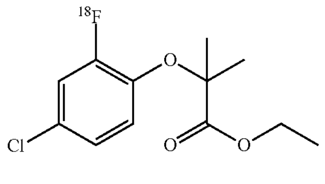 [SMILES: CCOC(=O)C(C)(C)Oc1ccc(Cl)cc1[18F]] | 3.7 ± 0.3% (n = 3) |
| 30 | 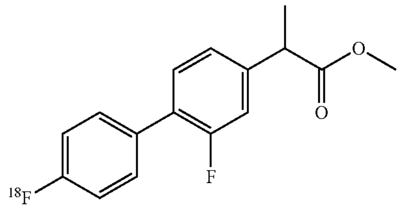 [SMILES: COC(=O)C(C)c1ccc(-c2ccc([18F])cc2)c(F)c1] | 36.8 ± 6% (n = 3) |
| 31 | 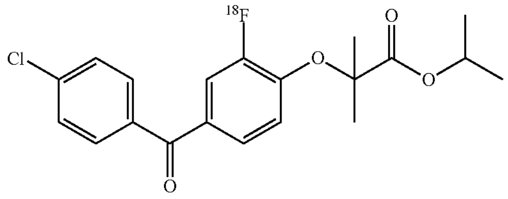 [SMILES: CC(C)OC(=O)C(C)(C)Oc1ccc(C(=O)c2ccc(Cl)cc2)cc1[18F]] | 5.6 ± 0.4% (n = 3) |
| 32 | 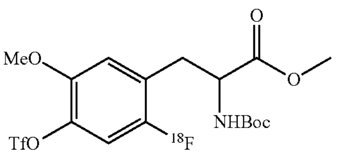 [SMILES: COC(=O)C(Cc1cc(OC)c(OS(=O)(=O)C(F)(F)F)cc1[18F])NC(=O)OC(C)(C)C] | 8.7 ± 1% (n = 3, 0.5h); 21.2 ± 0.5% (n = 3, 1h) |

The light protocol was also applied to more complex bioactive molecules. The protected DOPA afforded the p-position fluorinated product in 8.7% yield after 30 min irradiation (Table 7, no. 32). Simply increasing the reaction time to 1 h increased the yield up to 21.2%.

In summary, a facile method to quickly form Ar C—F bond from Ar C—H bond under mild conditions with only 30 min light irradiation is disclosed. The reaction does not require metal catalysts and could be performed with open-to-air reactors. Without wishing to be bound by theory, the reaction conditions are compatible with a broad spectrum of substrates and may be applied as a general method for $^{18}$F-labeled compounds that are used as novel diagnosis agents or for providing key information about in vivo fate/metabolites of target of interest. The method reported here establishes a new approach to quickly activate C—H bonds and can be further extended to $^{11}$C labeling or to other hard to achieve, slow reactions.

3. Synthesis of 1-(Fluoro-$^{18}$F)-4-Methoxybenzene from Phenol Derivative

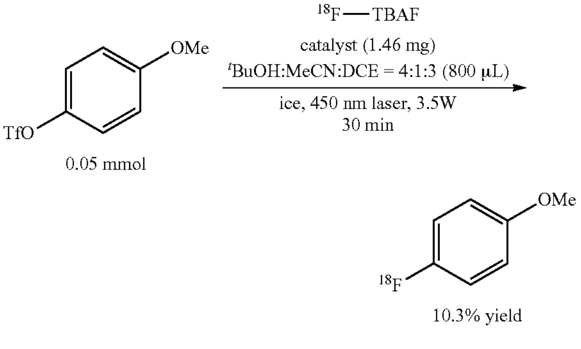

4. Synthesis of 4-(Fluoro-$^{18}$F)-1,1'-Biphenyl

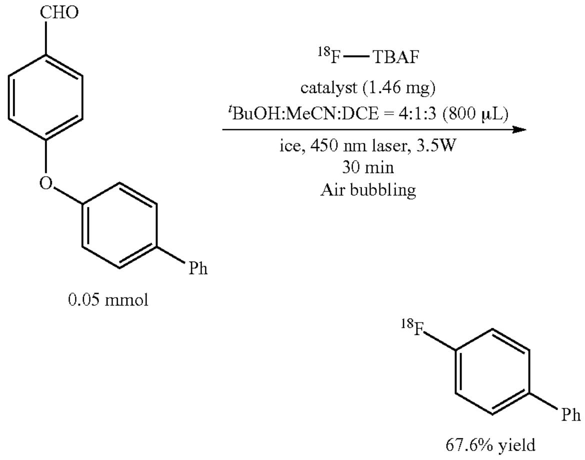

5. Introduction of Radioisotopes from Aromatic Halide Derivatives a. Synthesis of 1-(Fluoro-$^{18}$F)-4-Methoxybenzene

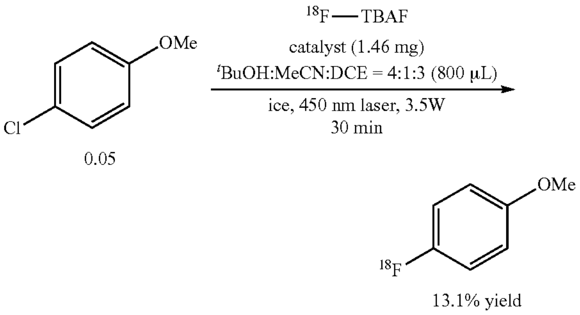

b. Synthesis of Ethyl 2-(4-(Fluoro-$^{18}$F)Phenoxy)-2-Methylpropanoate

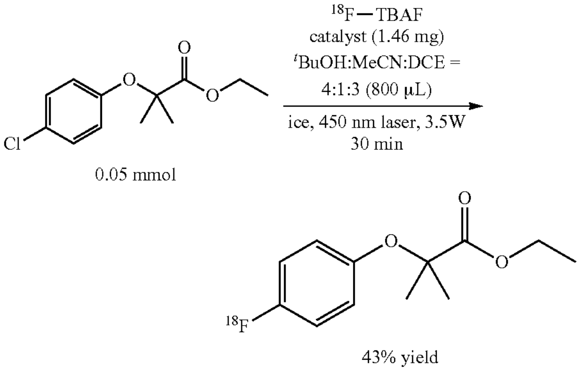

c. Synthesis of 1-(Fluoro-$^{18}$F)-4-Methoxybenzene from Aromatic Halide

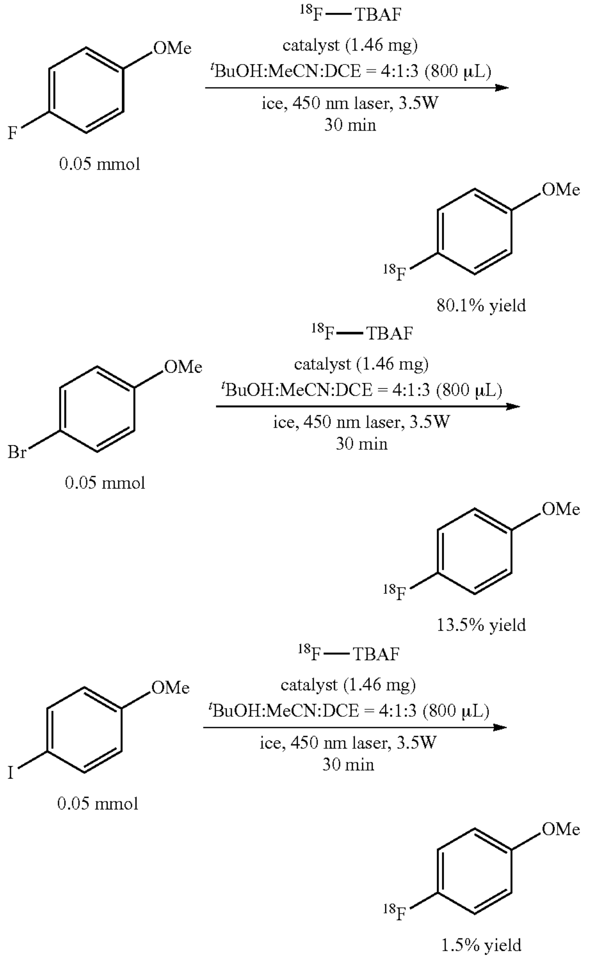

6. Direct Radiofluorination of Arene C—H Via LED Irradiated Photoredox Catalysis Positron emission tomography (PET) is an important imaging modality that plays key role in biomedical field including disease diagnosis, prognosis, treatment monitoring, and drug development (Simon et al. (2008) Chem. Rev. 108: 1501-1516). One commonly used approach to generate novel contrast agents for PET is to radiolabel pharmaceuticals with known activity towards the biological process or target of interest. Because fluorine-18 ($^{18}$F) is the most widely used PET isotope, significant amount of effort has been devoted to develop robust methods to radiofluorinate small-molecule pharmaceuticals (Tredwell and Gouverneur (2012) *Angew. Chem. Int. Ed. Engl.* 51: 11426-11437).

Traditionally, electron-deficient aromatic arenes could be fluorinated through nucleophilic substitution (Neumann et al. (2016) *Nature* 534: 369-373). Recently, dexoyfluorination (Schimler et al. (2017) *Journal of the American Chemical Society* 139: 1452-1455), demetaltion fluorination, copper catalyzed cross coupling (Truong et al. (2013) *Journal of the American Chemical Society* 135: 9342-9345), and iodonium intermediates (McCammant et al. (2017) *Org. Lett.* 19:

3939-3942) have been developed to radiofluorinate a larger spectrum of arenes. Herein, the discovery of a photoredox system/setup that allows direct C—H radiofluorination using readily available LED light is disclosed.

In order to replace laser light with LED, the overall light influx had to be significantly increased. Inspired by flow chemistry and microfluidic design, a micro-tubing reactor was created that greatly increased the surface area being exposed to light source. Unfortunately, performing the reaction in an enclosed micro-tubing reactor makes oxygen bubbling impractical. A screen of commonly used oxidizing agents was then performed to replace oxygen and the results are summarized in Table 8 below.

TABLE 8

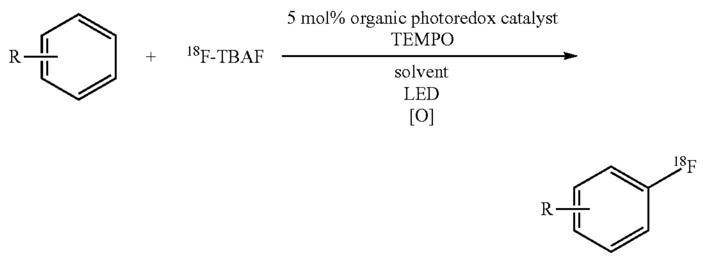

| Entry | Wavelength | Catalyst | [O] | Yield |
|---|---|---|---|---|
| 1[a] | 450 nm | Cat-20 | TBPB | 9.7%[b] |
| 2[a] | 450 nm | Cat-20 | TBPA | 15.7%[b] |
| 3[a] | 450 nm | Cat-20 | BPO | N.D.[b] |
| 4[a] | 450 nm | Cat-20 | TBHP | 7.4%[b] |
| 5[a] | 450 nm | Cat-20 | H202 | 2.4%[b] |
| 6[a] | 450 nm | Cat-20 | $PhI(OAc)_2$ | 0.5%[b] |
| 7[a] | 450 nm | Cat-20 | $KMnO_4$ | 19.2%[b] |
| 8[a] | 450 nm | Cat-20 | PCC | N.D.[b] |
| 9 | 365 nm | Cat-32 | TBPA | 7.7%[c] |
| 10 | 385 nm | Cat-32 | TBPA | 4.6%[c] |
| 11 | 410 nm | Cat-32 | TBPA | 12.6%[c] |
| 12 | 425 nm | Cat-32 | TBPA | 20.2%[c] |
| 13 | 450 nm | Cat-32 | TBPA | 17.4%[c] |

[a]Diphenyl ether (0.005 mmol), catalyst (0.00025 mmol), [O] 0.005 mmol, TEMPO (0.0025 mmol). The reaction mixture was then loaded to the capillary and sealed, then irradiated under LED 450 nm for 40 min at 0° C.

[b]Radiochemical yields (RCY) were calculated based on radio-TLC analysis with an eluent of ethyl acetate/hexane (v/v = 1/20) on silica gel 60 aluminium plate.

[c]2-Methoxybenzaldehyde (0.1 mmol), catalyst (0.025 mmol), [O] 0.05 mmol. The reaction mixture was then loaded to the capillary and sealed, then irradiated under LED 450 nm for 40 min at 0° C. Isolation RCYs were calculated by radio-HPLC.

tert-Butyl peroxybenzoate (TBPB), tert-Butyl peroxyacetate (TBPA), Benzoyl peroxide (BPO), tert-Butyl hydroperoxide (TBHP), Pyridinium chlorochromate (PCC)

By using diphenyl ether as the model substrate and incubation of oxidant [$^{18}$F]TBAF under irradiation of LED light, the reaction mixture was analyzed quickly by ratio-TLC. No aim product product was detected when benzoyl peroxide (BPO) or pyridinium chlorochromate (PCC) was applied as oxidant and only trace amount of product was detected when $PhI(OAc)_2$ or $H_2O_2$ were used as oxidant. Tert-butyl peroxyacetate (TBPA) was the second best oxidant among the oxidants tested, with a RCY of 15.7%. Tert-butyl peroxybenzoate (TBPB) and tert-butyl hydroperoxide (TBHP) were less reactive compared with TBPA, with a yield of 9.7% and 7.4%, respectively. Without wishing to be bound by theory, this suggests that the tert-butyl radical may play an important role in this reaction. he reaction with potassium permanganate as oxidant turned out to have the highest yield (19.23%) in this first screening for oxidant. However, the solubility of potassium permanganate in the reaction system is not good. This makes the reaction a heterogeneous mixture and, thus, leads to difficulty in sample loading, as well as resulting in an unstable yield. Though a bit lower than potassium permanganate, TBPA is much easier to handle and was therefore chosen for the next screen. Nine types of solvent, including tBuOH, acetonitrile, DMSO, toluene, dichloromethane, tetrahydofuran, N,N-dimethylformate, 1,4-dioxane, and methanol, were evaluated as the main medium in the reaction system. It was determined that the reaction performs best in tBuOH. See Tables 9 and 10 below. Based on these results, 1 equivalent of TBPA was used in tBuOH for further evaluation.

TABLE 9

| Main Solvent[a] | RCY[b] |
|---|---|
| TBuOH | 19.50% |
| CAN | 3.62% |
| DMSO | N.D. |
| Toluene | N.D. |
| $CH_2Cl_2$ | 10.27% |
| THF | 0.44% |
| DMF | 0.49% |
| 1,4-dioxane | 2.82% |
| MeOH | N.D. |

[a]Screening on solvent with Cat-20 (0.00025 mmol), LED 450 nm irradiation 40 min, diphenyl ether (0.005 mmol), TEMPO (0.0025 mmol), TBPB (0.01 mmol), $^{18}$F-TBAF in ACN (0.1~0.5 mCi), 0° C., and main solvent (40 ul). Small amount of reaction mixture was loaded in capillary and sealed for reaction.

[b]RCY calculated by radio-TLC.

TABLE 10

| Equivalent[a] | RCY[b] |
|---|---|
| 0 eq. | 9.76% |
| 0.1 eq. | 17.92% |
| 0.5 eq. | 21.3% |
| 1.0 eq. | 22.87% |
| 2.0 eq. | 13.97% |
| 5.0 eq. | N.D. |

[a]Screening on [O] equivalent with Cat-20 (0.00025 mmol), LED 450 nm irradiation 40 min, diphenyl ether (0.005 mmol), TEMPO (0.0025 mmol), $^{18}$F-TBAF in ACN (0.1~0.5 mCi), 0° C. Small amount of reaction mixture was loaded in capillary and sealed for reaction.
[b]RCY calculated by radio-TLC.

Figure 10:
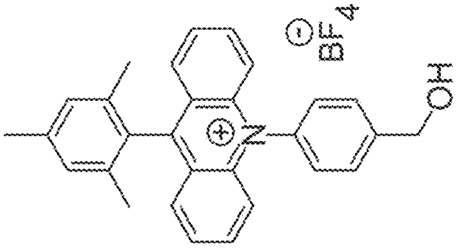
FIG. 10 shows representative structures of catalysts explored herein.
Figure 10:
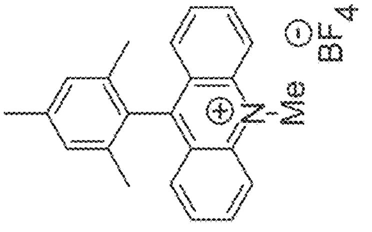
Figure 10:
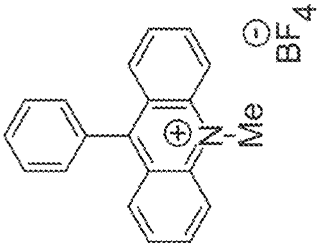
Figure 10:
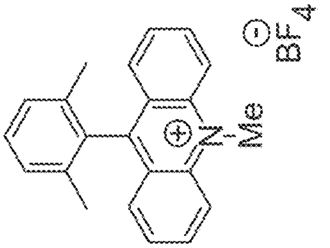
Figure 10:
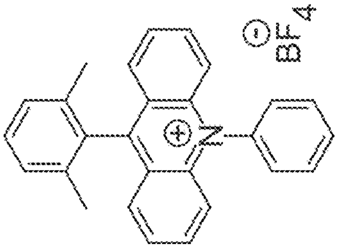
Figure 10:
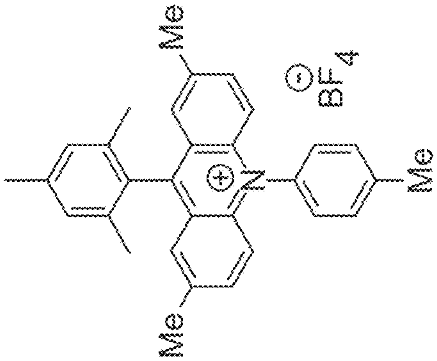
Figure 10:
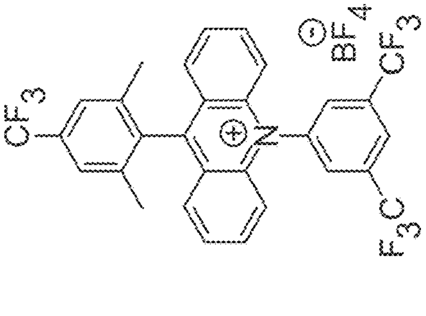
Figure 10:
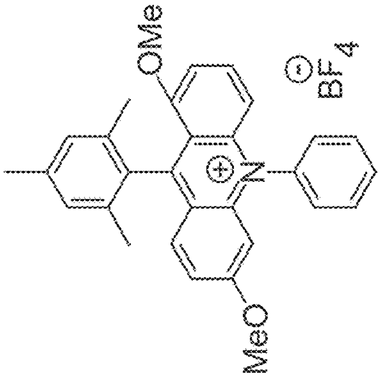
Figure 10:
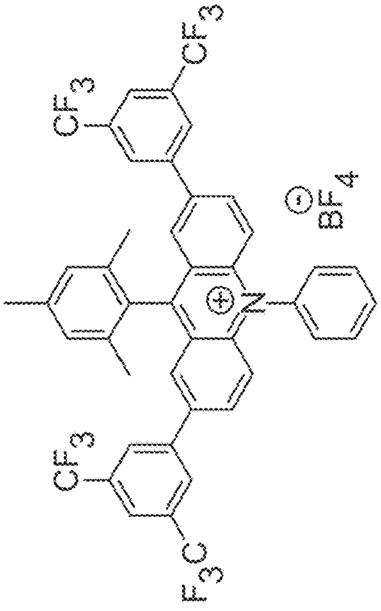
Figure 10:
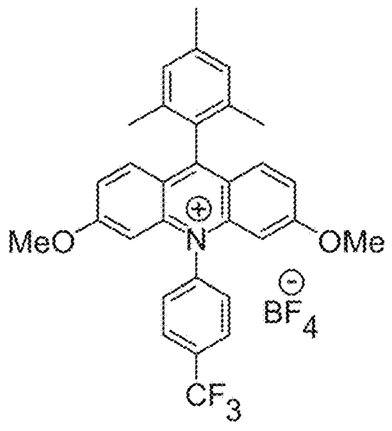
Figure 10:
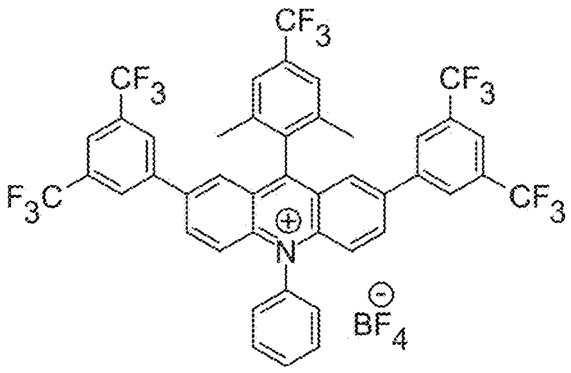
Figure 10:
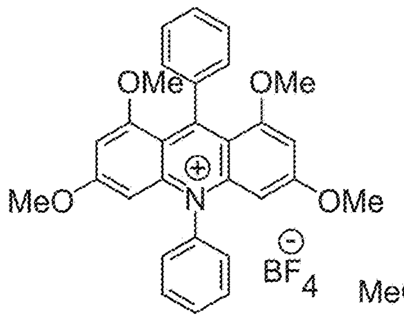
Figure 10:
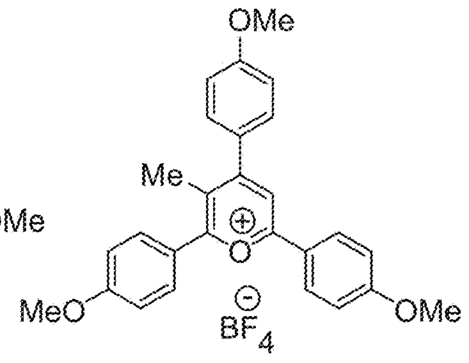
Figure 10:
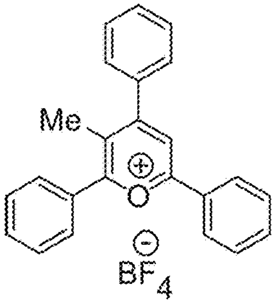
Figure 10:
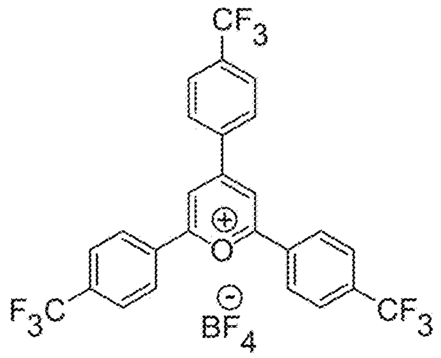
Figure 10:
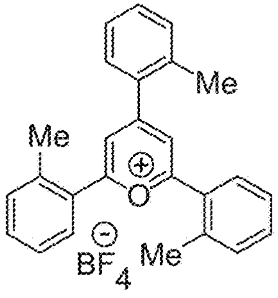
Figure 10:
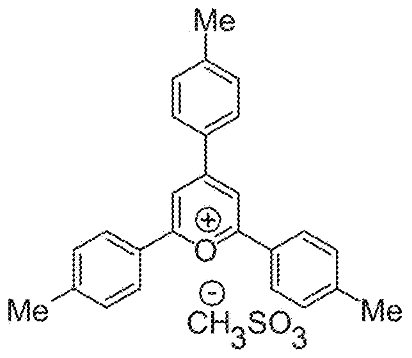
Figure 10:
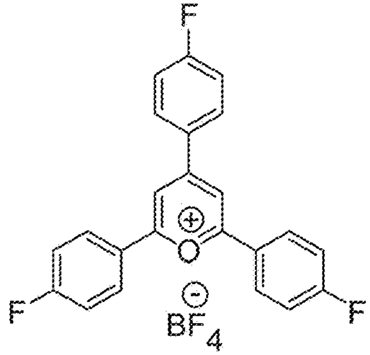
Figure 10:
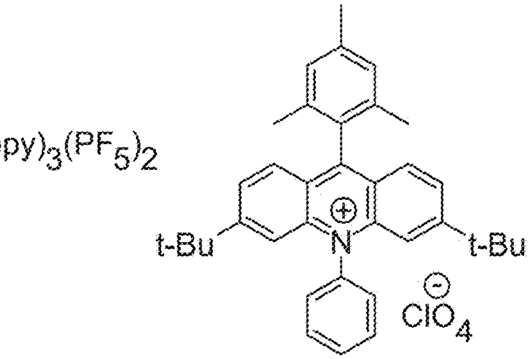
Figure 10:
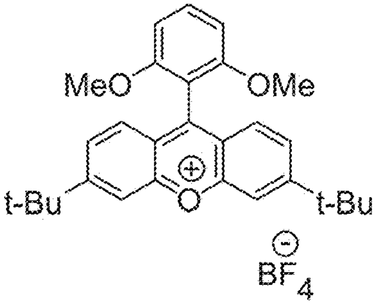
Figure 10:
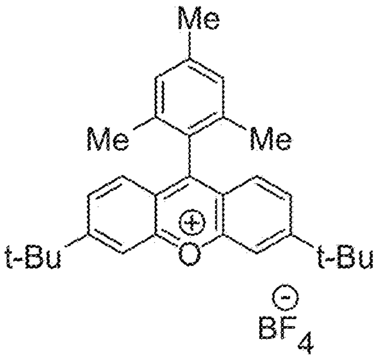
Figure 10:
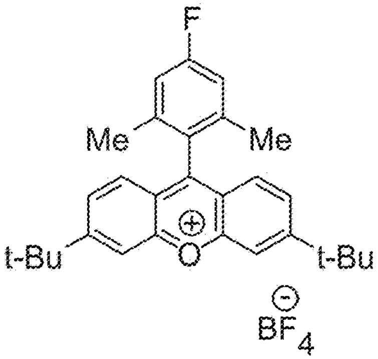
Figure 10:
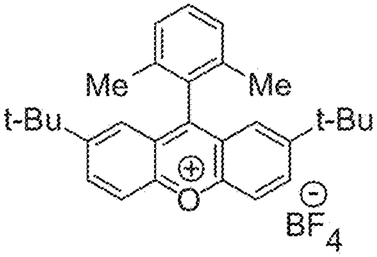
Figure 10:
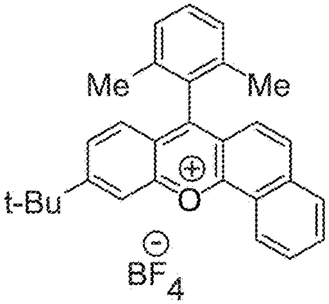
Figure 10:
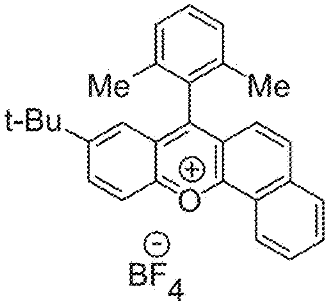
Figure 10:
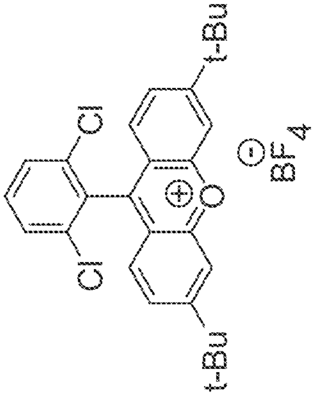
Figure 10:
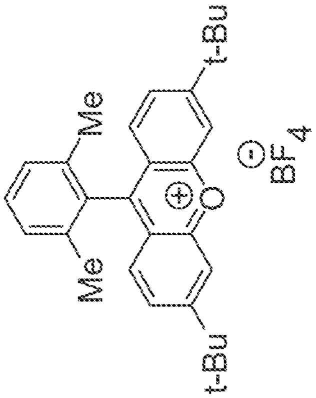
Figure 10:
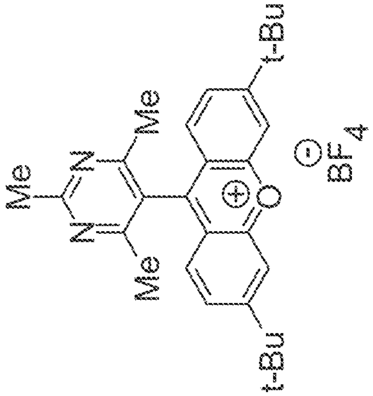
Figure 10:
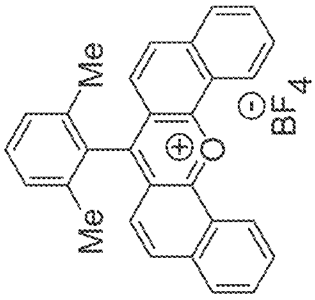
Figure 10:
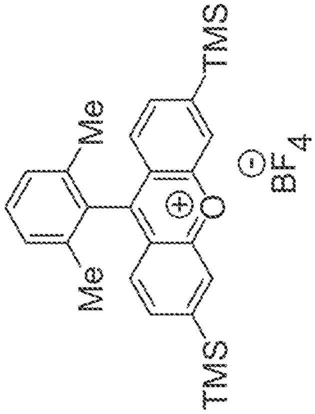
Figure 10:
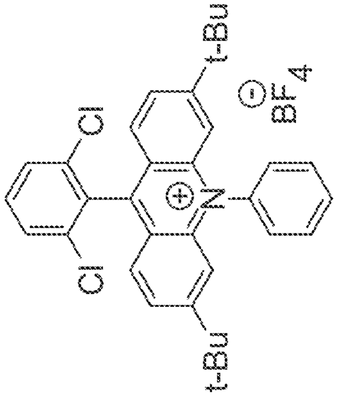
Figure 10:
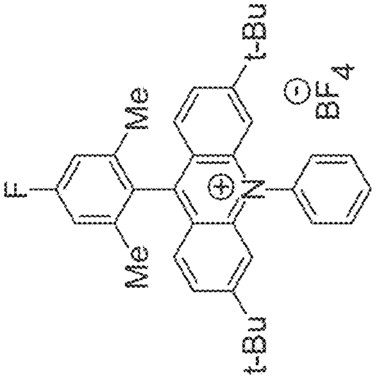
Figure 10:
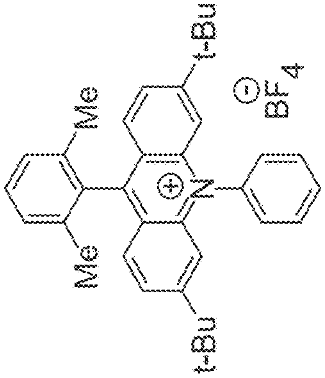
Figure 10:
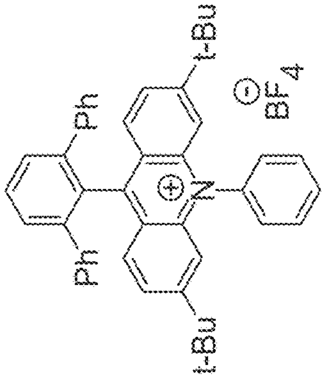
Figure 10:
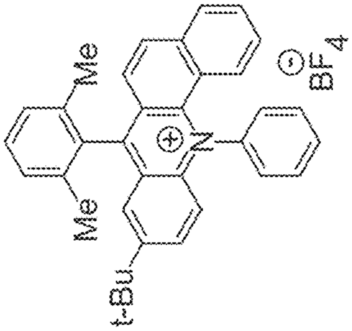
Figure 10:
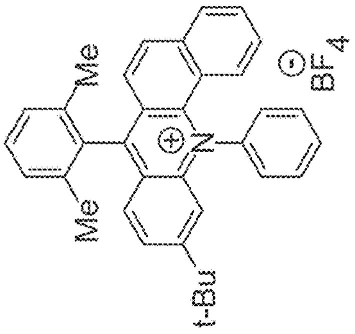
Figure 10:
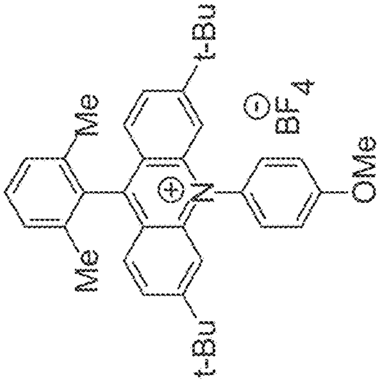
Figure 10:
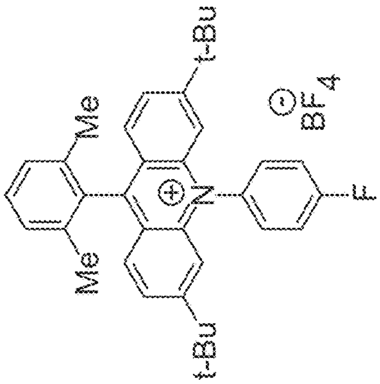
Figure 10:
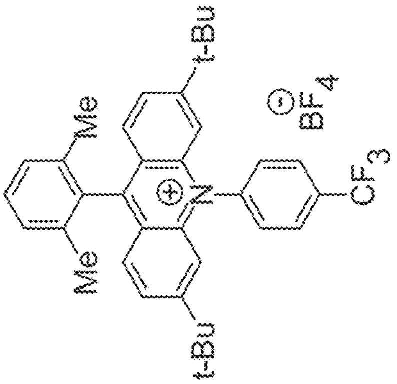
Figure 10:
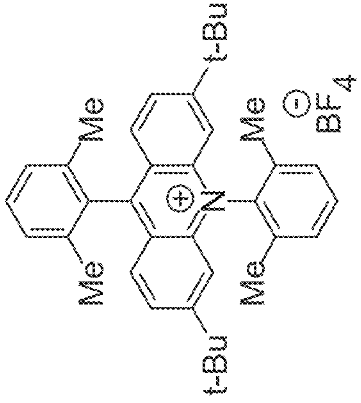
Figure 10:
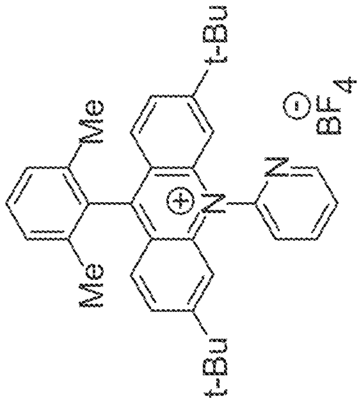
Figure 10:
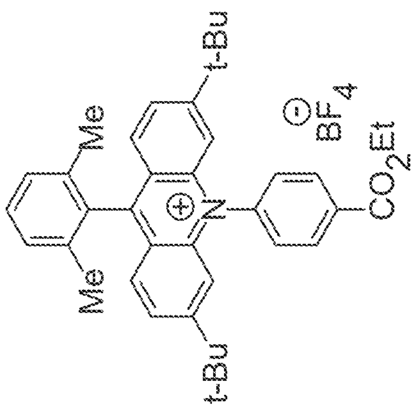
Figure 10:
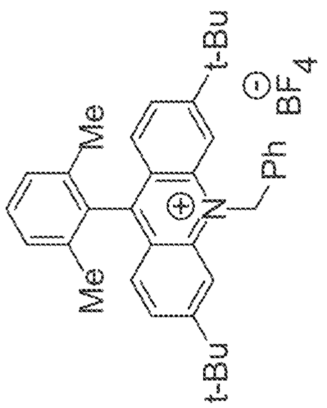
Figure 10:
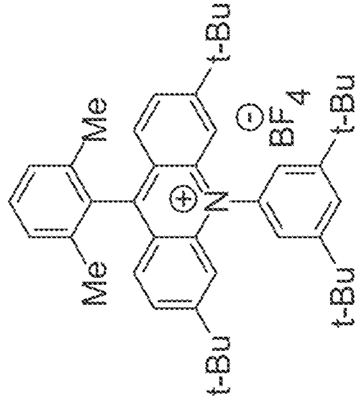
Figure 10:
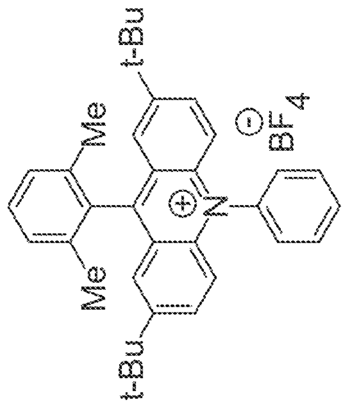
Figure 10:
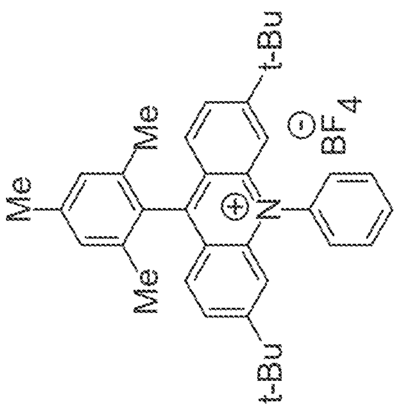
Figure 10:
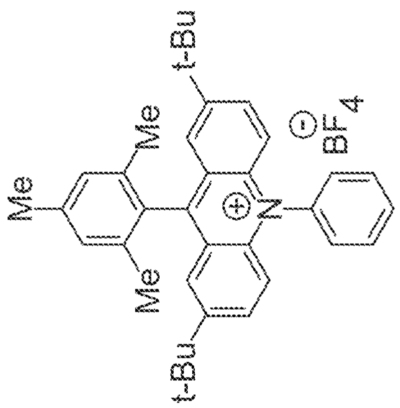

Next, a library of 48 organic photocatalysts was evaluated (FIG. 10) and the results were shown in Table 11. Generally, acridinium catalysts were more efficient compared with xanthylium catalyst. No aim product was detected when xanthylium catalyst (Cat-21 to Cat-31) or 2,4,6-triphenylpyrylium catalysts (Cat-13 to Cat-18) were applied in the reaction. Cat-32 achieved good results when used with an RCY of 42.4% (Table 11). Not much difference was observed when the reaction was carried out at room temperature or 40° C. The effect of LED light wavelength on the reaction was also evaluated.

TABLE 11

| Entry | Catalyst[a] | RCY[b] |
|---|---|---|
| 1 | Cat-1 | 20.8% |
| 2 | Cat-2 | 10.6% |
| 3 | Cat-3 | N.D. |
| 4 | Cat-4 | 8.6% |
| 5 | Cat-5 | 5.7% |
| 6 | Cat-6 | N.D. |
| 7 | Cat-7 | 10.6% |
| 8 | Cat-8 | N.D. |
| 9 | Cat-9 | 1.2% |
| 10 | Cat-10 | 34.6% |
| 11 | Cat-11 | 1.8% |
| 12 | Cat-12 | N.D. |
| 13 | Cat-13 | N.D. |
| 14 | Cat-14 | N.D. |
| 15 | Cat-15 | N.D. |
| 16 | Cat-16 | N.D. |
| 17 | Cat-17 | N.D. |
| 18 | Cat-18 | N.D. |
| 19 | Cat-19 | N.D. |
| 20 | Cat-20 | 12.3% |
| 21 | Cat-21 | N.D. |
| 22 | Cat-22 | N.D. |
| 23 | Cat-23 | N.D. |
| 24 | Cat-24 | N.D. |
| 25 | Cat-25 | N.D. |
| 26 | Cat-26 | N.D. |
| 27 | Cat-27 | N.D. |
| 28 | Cat-28 | N.D. |
| 29 | Cat-29 | N.D. |
| 30 | Cat-30 | N.D. |
| 31 | Cat-31 | N.D. |
| 32 | Cat-32 | 42.4%[c] |
| 33 | Cat-33 | 28.0% |
| 34 | Cat-34 | 41.0% |
| 35 | Cat-35 | 29.6% |
| 36 | Cat-36 | 29.2% |
| 37 | Cat-37 | 28.5% |
| 38 | Cat-38 | 29.5% |
| 39 | Cat-39 | 37.5% |
| 40 | Cat-40 | 29.2% |
| 41 | Cat-41 | 17.9% |
| 42 | Cat-42 | 17.4% |
| 43 | Cat-43 | 26.0% |
| 44 | Cat-44 | 23.0% |
| 45 | Cat-45 | 21.8% |
| 46 | Cat-46 | 37.6% |
| 47 | Cat-47 | 32.5% |
| 48 | Cat-48 | 28.7% |

[a]Chemical structures of the catalysts were summarized in FIG. S1. Diphenyl ether (0.005 mmol), Cat (0.00025 mmol), TEMPO (0.0025 mmol), TBPA (0.005 mmol), $^{18}$F-TBAF in ACN (0.5~1.5 mCi) and tBuOH (40 ul). The reaction mixture was then loaded to the capillary and sealed, then irradiated under LED 450 nm for 40 min at 0° C.
[b]Radiochemical yields (RCY) were calculated based on radio-TLC analysis with an eluent of ethyl acetate/hexane (v/v = 1/20) on silica gel 60 aluminium plate.
[c]RCY of 36.43% when reaction was carried out at room temperature and RCY of 43.32% when reaction was carried out at 40° C.

Figure 11:
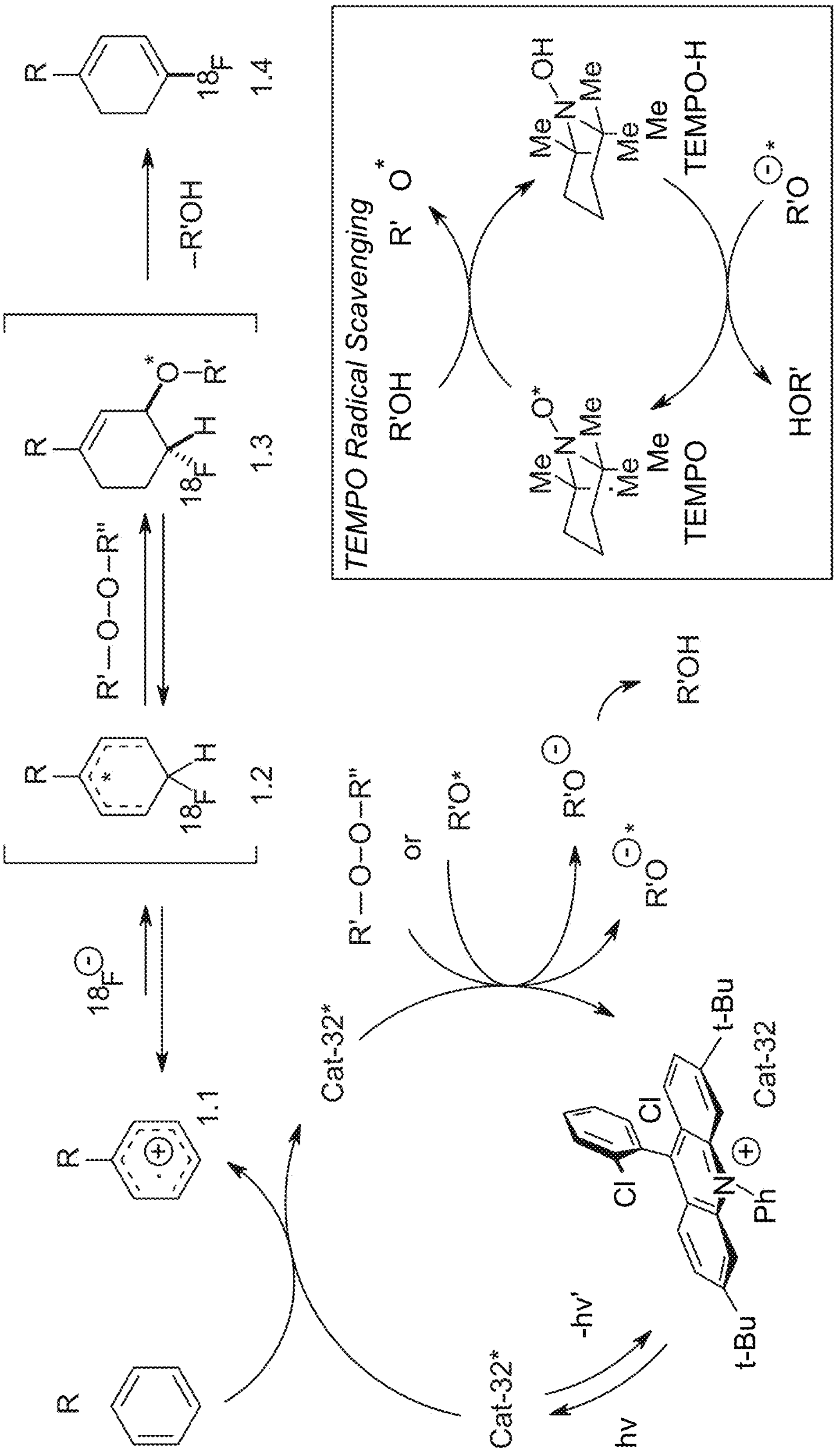
FIG. 11 shows a representative schematic illustrating a mechanistic proposal for oxidative C—H [18F]fluorination of aromatics.
Figure 12:
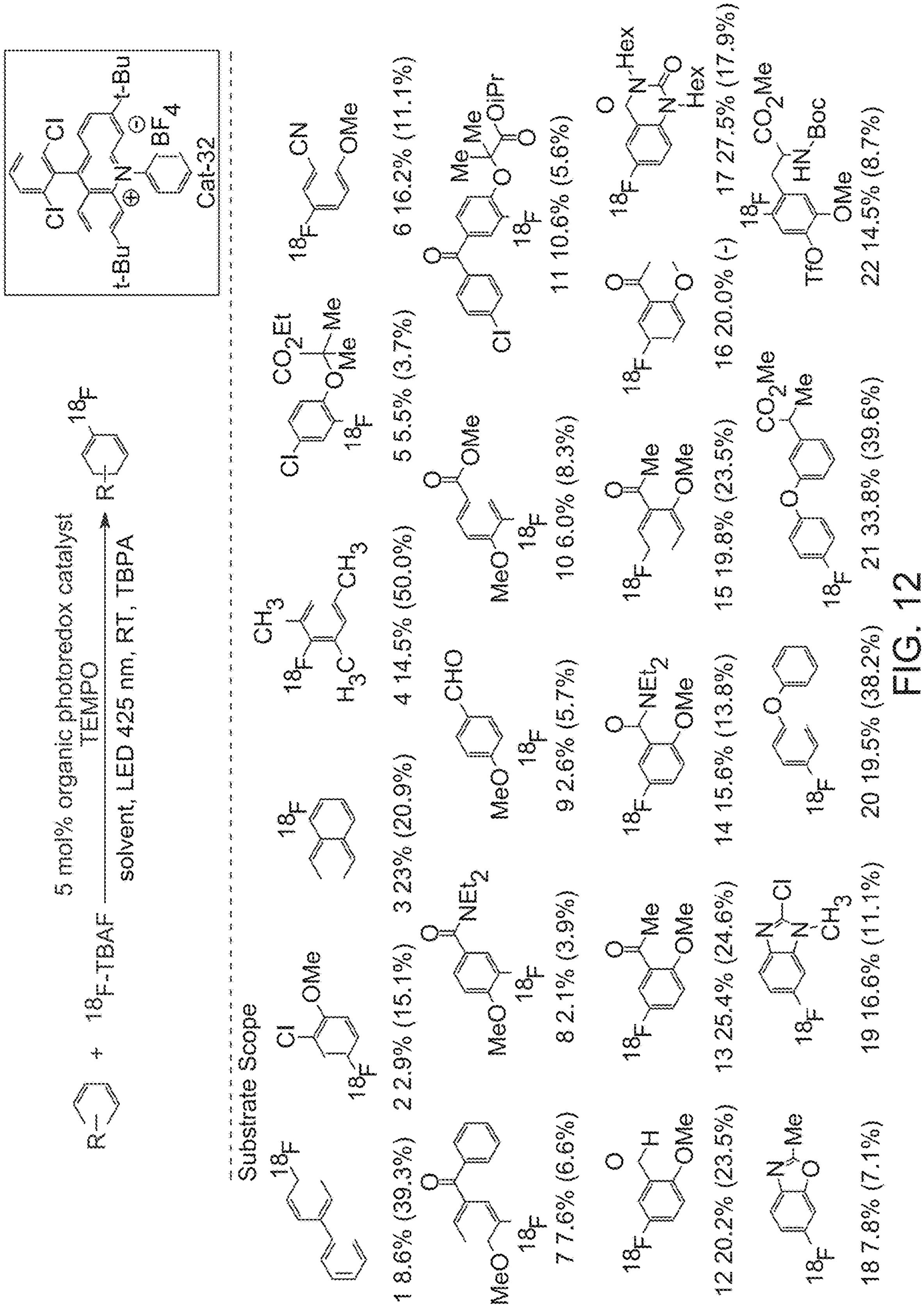
FIG. 12 shows representative data illustrating the scope of radiofluorination of arene C—H.

The mechanistic proposal begins with single electron oxidation of the arene by the excited state of the photocatalyst (Cat-32*), after which the arene cation radical (1.1) can be intercepted by an amine or alcohol present in solution, leading to the formation of radical 1.2 (FIG. 11). The exact nature of the following oxidation is less clear. Without wishing to be bound by theory, it is presumed that the oxidant reacts with cyclohexadienyl radicals to lead to alkylperoxyl radicals (1.3). Intramolecular hydrogen atom transfer (HAT) and extrusion of an alcohole unit (R'OH) would then furnish the fluorinated arene. Nitroxyl radicals, the archetypal example, 2,2,6,6-tetramethyl-1-piperidine 1-oxyl (TEMPO), react rapidly with cyclohexadienyl radicals via hydrogen atom abstraction to yield the corresponding aromatic compounds (1.4) (Xian-Ming Pan (1993) *J. Chem. Soc. Perkin Trans.* 2: 9). The C—H bond enthalpies for cyclohexadienyl radicals have been estimated at approximately 50 kcal $mol^{-1}$, whereas the O—H bond enthalpy for TEMPO-H has been assessed at 70 kcal $mol^{-1}$. This raises the prospect for employing nitroxyl radicals as cocatalysts in the proposed transformations as the reoxidation of TEMPO-H to TEMPO by oxidant is facile.

Figure 13:
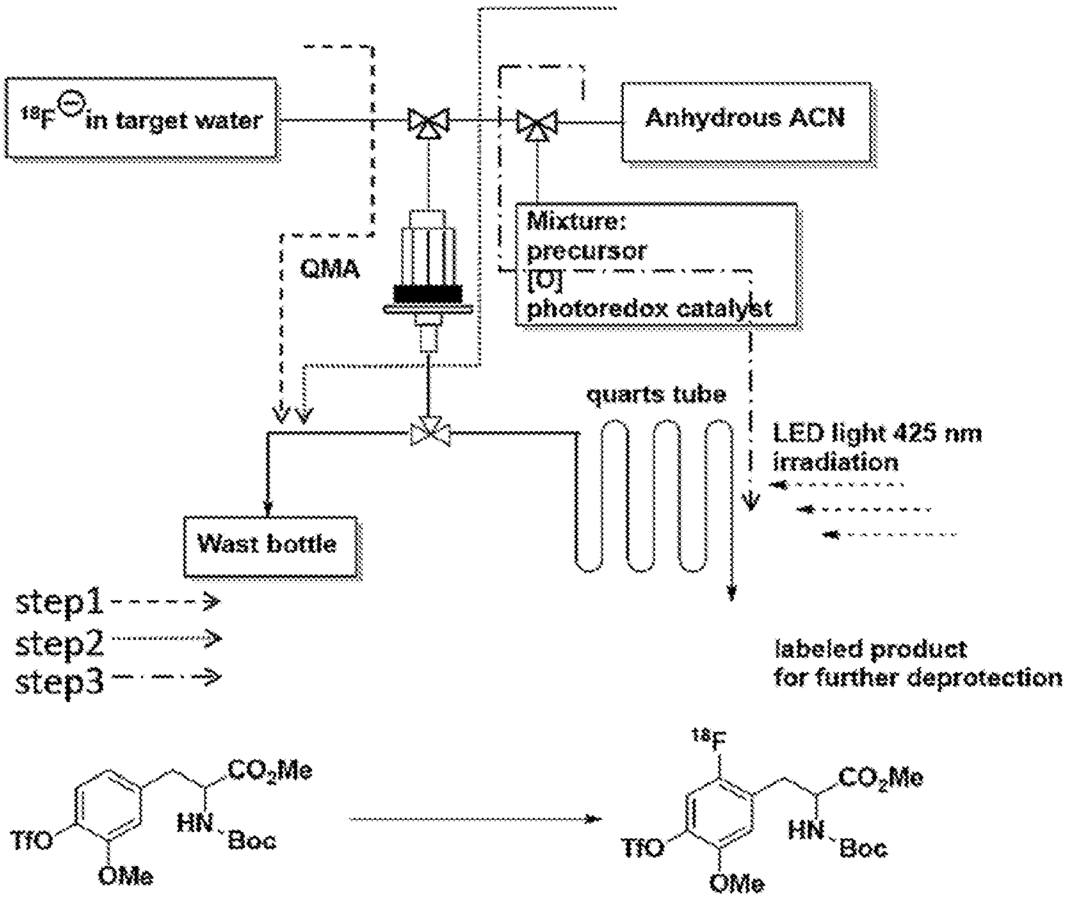
FIG. 13 shows a representative schematic workflow of preparing $^{18}$F labeled agent through direct C—H fluorination and its application in $^{18}$F-DOPA synthesis.
Figure 14:
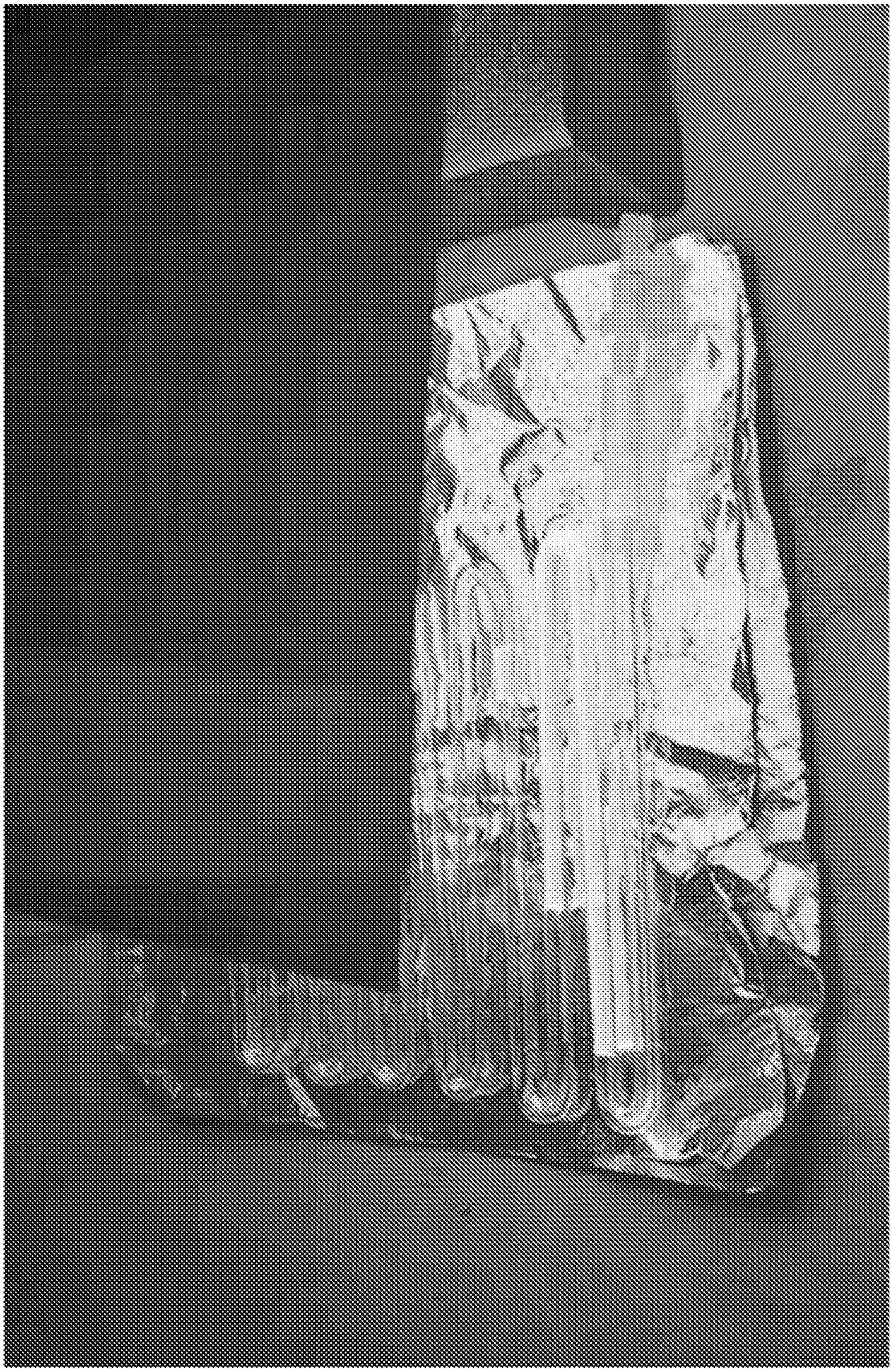
FIG. 14 shows a representative image illustrating LED irradiation of the hot reaction mixture in quartz U-tube.

Having evaluated the scope of this radiofluorination, it was sought to further simplify the labeling procedures by eliminating the azeotropic drying step in preparation of [$^{18}$F]-TBAF. The preparation of $^{18}$F-source in target water was directly trapped on pre-activated mini-QMA. The 5 mL of anhydrous acetonitrile was passing through the minigma to wash out most water on the QMA. Without wishing to be bound by theory, it was found that by adding a small amount of TBAB solution (25 ul, 1.5 mg in ACN) to the mixture of substrate, catalyst, and oxidant solution in tBuOH, the [$^{18}$F]-TBAF easily eluted out. Then the reaction mixture was loaded in a quartz micro tube and irradiated under LED light at room temperature. Next, the activity was collected into a 1.5 mL microcentrifuge tube and further evaluated by radio-HPLC. The process is illustrated in FIG. 13. Finally, this method was applied using compound 23 as the starting material, which afforded product [$^{18}$F]-22 in 22.8% isolated RCY.

In summary, a LED irradiated photoredox system has been developed that allows for fast and direct radiofluorination of arene C—H. These mild reaction conditions can be applied to synthesize novel $^{18}$F-labeled radiotracers.

a. General Experimental Details

[$^{19}$F]-Standards and [$^{18}$F]-precursors used herein were either synthesized according to previously described methods or were commercially purchased.

b. General Procedure A

Photocatalyst (0.00125 mmol, 0.025 eq.), substrate (0.05 mmol, 1.0 eq.), TEMPO (1.9 mg, 0.012 mmol, 0.25 eq), oxidant (0.05 mmol, 1.0 eq.) were added into a 1.5 mL microcentrifuge tube and dissolved in 20-30 μL anhydrous MeCN and 200 μL t-BuOH. Then a 20-30 μL aliquot of [$^{18}$F]TBAF in MeCN (typically 2-3 mCi) [total volume of MeCN is 50 μL] was immediately added to the reaction vial via pipette. Decay in [$^{18}$F]TBAF activity was monitored upon addition of [$^{18}$F]TBAF to the substrate solution. After that the reaction mixture was loaded to the quartz capillary tube and then irradiated by LED light for 40 min at room temperature. The resulting solution was injected into HPLC for analysis and isolation. The fraction of $^{18}$F-radiolabeled product was collected and the activity was measured. The radiochemical yields of all [$^{18}$F]-labeled molecules were based on isolated via HPLC as indicated in the substrates scope. [$^{18}$F]-Radiolabeled products were confirmed by the co-injection of commercial or synthesized $^{19}$F standards via HPLC. Quality control (QC) was run separately to ensure the purity of isolated radiolabeled compounds.

c. General Procedure B

A [$^{18}$F]F— in the target water was trapped on a pre-activated mini-QMA, then 5 mL anhydrous acetonitrile was passed the QMA. After that a solution of Cat-32 (0.00125 mmol, 0.025 eq.), substrate (0.05 mmol, 1.0 eq.), TEMPO (1.9 mg, 0.012 mmol, 0.25 eq), TBPA (0.05 mmol, 1.0 eq.) in 200 ul tBuOH and 50 ul acetonitrile were applied as elute, the resulting eluent were loaded in the quartz tube and irradiated under LED 425 nm light for 40 min at room temperature. An aliquot of the reaction mixture (typically 400-800 μCi) was taken for radio-HPLC analysis.

d. Spectral Evaluation of Exemplary Compounds

The exemplary compounds were evaluated using radio-HPLC with specific conditions as detailed below. All compounds were determined to have a purity of >98%.

(i) Compound 1

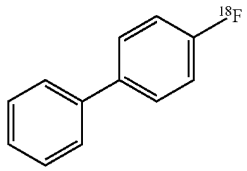 [SMILES: [18F]c1ccc(-c2ccccc2)cc1]

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: 20-45% solvent B, 2 to 22 min: 45-60% solvent B, 22 to 28 min: 60-95% solvent B, 28 to 35 min: isocratic 95% solvent B. Flow rate: 1 mL/min, column temperature: 19 to 21° C.

(ii) Compound 2

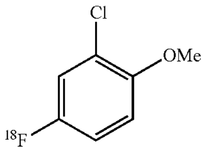

HPLC condition: (A) Column: Phenomenex, Gemini 5 μm C18 110A, New Column 250×4.6 mm. Solvent A: 0.10% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 22 min: 45-60% solvent B, 22 to 28 min: 60-95% solvent B, 28 to 40 min: isocratic 95% solvent B. Flow rate: 1 mL/min, column temperature: 19 to 21° C.

(iii) Compound 3

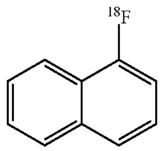 [SMILES: [18F]c1cccc2ccccc12]

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 12 min: isocratic 5% solvent B, 12 to 32 min: 5-95% solvent B, 32 to 40 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; isocrat: 0 to 2 min: 5% solvent B, 2 to 22 min: 50-58% solvent B, 22 to 28 min: 58-95% solvent B, 28 to 40 min: isocratic 95% solvent B. Flow rate: 1 mL/min, column temperature: 19 to 21° C.

(iv) Compound 4

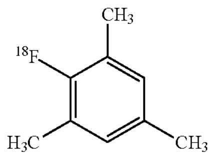

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 22 min: 50-58% solvent B, 22 to 28 min: 58-95% solvent B, 28 to 40 min: isocratic 95% solvent B. Flow rate: 1 mL/min, column temperature: 19 to 21° C.

(v) Compound 5

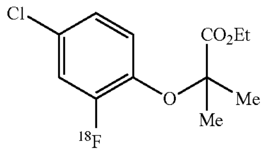 [SMILES: CCOC(=O)C(C)(C)Oc1ccc(Cl)cc1[18F]]

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column:

Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 55% solvent B. Flow rate: 1 mL/min, column temperature: 19 to 21° C.

(vi) Compound 6

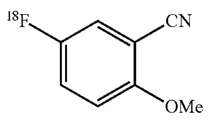

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 22 min: 45-60% solvent B, 22 to 28 min: 60-95% solvent B, 28 to 40 mm: isocratic 95% solvent B. Flow rate: 1 mL/min, column temperature: 19 to 21° C.

(vii) Compound 7

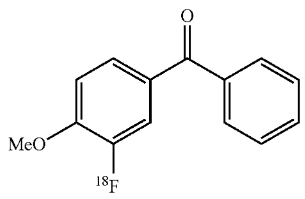

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5%, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; isocratic 0 to 2 min: 5% solvent B, 2 to 40 min: isocratic 50% solvent B. Flow rate: 1 mL/min, column temperature: 19 to 21° C.

(VIII) Compound 8

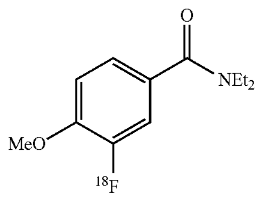

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 50% solvent B. Flow rate: 1 mL/min, column temperature: 19 to 21° C.

(ix) Compound 9

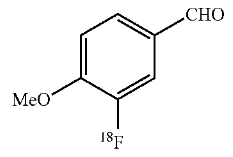 [SMILES: COc1ccc(C=O)cc1[18F]]

HPLC condition: (A) Column: Phenomenex, Gemini 5 μm C18 110A, New Column 250×4.6 mm. Solvent A: 0.10% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 45% solvent B. Flow rate: 1 mL/min, column temperature: 19 to 21° C.

(x) Compound 10

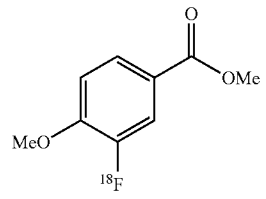 [SMILES: COC(=O)c1ccc(OC)c([18F])c1]

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 40 min isocratic 35% solvent B. Flow rate: 1 mL/min, column temperature: 19 to 21° C.

(xi) Compound 11

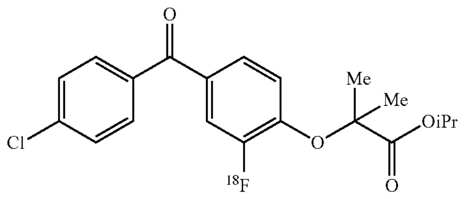 [SMILES: CC(C)OC(=O)C(C)(C)Oc1ccc(C(=O)c2ccc(Cl)cc2)cc1[18F]]

HPLC condition: (A) Column: Phenomenex, Gemini 5 μm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 μm F5 100 Å, 250×4.6 mm LC Column. Solvent A: 0.1% TFA water; Solvent B: 0.1% TFA acetonitrile; 0 to 40 min isocratic 35% solvent B. Flow rate: 1 mL/min, column temperature: 19 to 21° C.

(xii) Compound 12

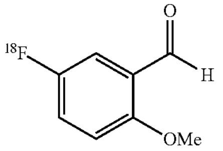

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 40% solvent B. Flow rate: 1 mL/min, column temperature: 19 to 21° C.

(xiii) Compound 13

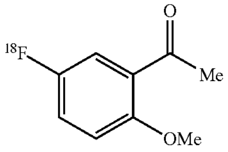 [SMILES: COc1ccc([18F])cc1C(C)=O]

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 40 min isocratic 40% solvent B. Flow rate: 1 mL/min, column temperature: 19 to 21° C.

(xiv) Compound 14

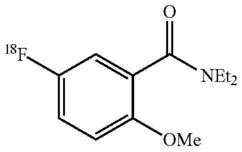

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 40% solvent B. Flow rate: 1 mL/min, column temperature: 19 to 21° C.

(xv) Compound 15

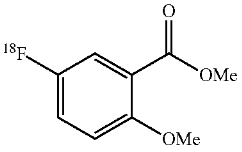 [SMILES: COC(=O)c1cc([18F])ccc1OC]

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 40 min isocratic 35% solvent B. Flow rate: 1 mL/min, column temperature: 19 to 21° C.

(xvi) Compound 16

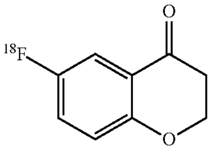 [SMILES: O=C1CCOc2ccc([18F])cc21]

HPLC condition: (A) and (B) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (C) Column: Phenomenex, Gemini 5 µm C18 110A, New Column 250×4.6 mm. Solvent A: 0.1% TFA water; Solvent B: 0.1% TFA acetonitrile; 0 to 2 min: 5-30% solvent B, 2 to 22 min: 30-60% solvent B, 22 to 27 min: 60-95% solvent B, 27 to 40 min 95% solvent B isocratic. Flow rate: 1 mL/min, column temperature: 19 to 21° C.

(xvii) Compound 17

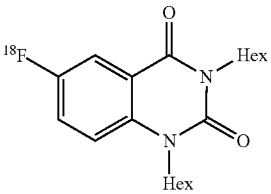

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; Solvent A: 0.1% TFA water; Solvent B: 0.1% TFA acetonitrile; 0 to 2 min: isocratic 5% solvent B, 2 to 40 min: isocratic 35% solvent B. Flow rate: 1 mL/min, column temperature: 19 to 21° C.

(xviii) Compound 18

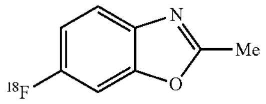 [SMILES: Cc1nc2ccc([18F])cc2o1]

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; Solvent A: 0.1% TFA water; Solvent B: 0.1% TFA acetonitrile; 0 to 2 min: isocratic 5% solvent B, 2 to 40 min: isocratic 35% solvent B. Flow rate: 1 mL/min, column temperature: 19 to 21° C.

(xix) Compound 19

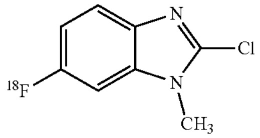

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; Solvent A: 0.1% TFA water; Solvent B: 0.1% TFA acetonitrile; 0 to 2 min: isocratic 5% solvent B, 2 to 40 min: isocratic 30% solvent B. Flow rate: 1 mL/min, column temperature: 19 to 21° C.

(xx) Compound 20

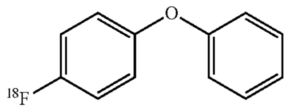 [SMILES: [18F]c1ccc(Oc2ccccc2)cc1]

HPLC condition: (A) Column: Phenomenex, Gemini 5 µm C18 110A, New Column 250×4.6 mm. Solvent A: 0.1% TFA water; Solvent B: 0.11% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 2 min: isocratic 5% solvent B, 2 to 22 min: 50-58% solvent B, 22 to 28 min: 58-95% solvent B, 28 to 40 min: isocratic 95% solvent B. Flow rate: 1 mL/min, column temperature: 19 to 21° C.

(xxi) Compound 21

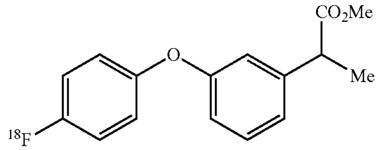 [SMILES: COC(=O)C(C)c1cccc(Oc2ccc([18F])cc2)c1]

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 2 min: isocratic 60% solvent B, 2 to 22 min: 60-85% solvent B, 22 to 28 min: 85-95% solvent B, 28 to 40 min: isocratic 95% solvent B. Flow rate: 1 mL/min, column temperature: 19 to 21° C.

(xxii) Compound 22

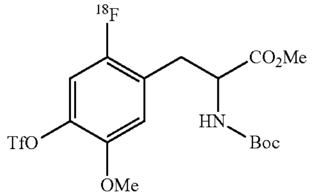 [SMILES: COC(=O)C(Cc1cc(OC)c(OS(=O)(=O)C(F)(F)F)cc1[18F])NC(=O)OC(C)(C)C]

HPLC condition: (A) Column: Phenomenex, Gemini 5 µm C18 110A, New Column 250×4.6 mm. Solvent A: 0.1% TFA water; Solvent B: 0.1% TFA acetonitrile; 0 to 2 min: isocratic 5% solvent B, 2 to 22 min: 5-95% solvent B, 22 to 35 min: isocratic 95% solvent B. Flow rate: 1 mL/min, column temperature: 19 to 21° C. (B) and (C) Column: Phenomenex, Kinetex® 5 µm F5 100 Å, 250×4.6 mm LC Column. Solvent A: 0.1% TFA water; Solvent B: 0.1% TFA acetonitrile; 0 to 2 min: isocratic 5% solvent B, 2 to 40 min: isocratic 60% solvent B. Flow rate: 1 mL/min, column temperature: 19 to 21° C.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a compound having a structure represented by a formula:

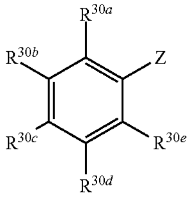

wherein Z is selected from halogen, —CN, —$NH_2$, C1-C4 alkylamino, and (C1-C4)(C1-C4) dialkylamino, provided that when Z is —$NH_2$, C1-C4 alkylamino, or (C1-C4)(C1-C4) dialkylamino, then Z contains a radioisotope;

wherein each of $R^{30a}$, $R^{30b}$, $R^{30c}$, $R^{30d}$, and $R^{30e}$ is independently selected from hydrogen, halogen, —CN, —$NO_2$, C1-C8 alkyl, C1-C8 alkoxy, —O—(C1-C8 alkyl)-$CO_2$—(C1-C8 alkyl), —C(=O)$R^{10}$, —C(=O)$OR^{11}$, —C(=O)$NR^{12a}R^{12b}$, $Ar^2$, and —$CH_2CR^{13}$($NR^{14a}R^{14b}$)$CO_2R^{15}$;

wherein each of $R^{10}$, $R^{11}$, $R^{12a}$, $R^{12b}$, $R^{13}$, and $R^{15}$, when present, is independently selected from hydrogen and C1-C4 alkyl;

wherein each of $R^{14a}$ and $R^{14b}$, when present, is independently selected from hydrogen, C1-C4 alkyl, and amine protecting group; and wherein $Ar^2$, when present, is selected from aryl and heteroaryl, and substituted with 0, 1, 2, or 3 groups independently selected from halogen, —CN, —$NO_2$, —OH, —SH, —$NH_2$, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino;

the method comprising the step of reacting an arene having a structure represented by a formula:

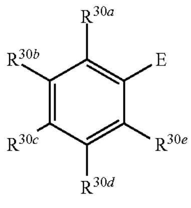

wherein each of $R^{30a}$, $R^{30b}$, $R^{30c}$, $R^{30d}$, and $R^{30e}$ is independently selected from hydrogen, halogen, —CN, —$NO_2$, C1-C8 alkyl, C1-C8 alkoxy, —O—(C1-C8 alkyl)-$CO_2$—(C1-C8 alkyl), —C(=O)$R^{10}$, —C(=O)$OR^{11}$—C(=O)$NR^{12a}R^{12b}$, $Ar^2$, and —$CH_2CR^{13}$($NR^{14a}R^{14b}$)$CO_2R^{15}$;

wherein E is an electron donating group is selected from —$OR^{20}$, —$SO_3R^{20}$, —$SR^{20}$, —$NR^{21a}R^{21b}$, —OC(=O)$R^{20}$, —OC(=O)$OR^{20}$, —OC(=O)$SR^{20}$, and —OC(=O)$NHR^{20}$;

wherein $R^{20}$, $R^{21a}$, and $R^{21b}$, when present, is independently selected from hydrogen, C1-C8 alkyl, C1-C8 alkenyl, and $Ar^3$; and wherein $Ar^3$, when present, is selected from aryl and heteroaryl, and substituted with 0, 1, 2, or 3 groups independently selected from halogen, —CN, —$NO_2$, —OH, —SH, —$NH_2$, —CHO, C1-C4 alkyl, C1-C4 haloalkyl, C1-C4 cyanoalkyl, C1-C4 alkoxy, C1-C4 hydroxy, C1-C4 thioalkoxy, C1-C4 alkylthiol, C1-C4 aminoalkyl, C1-C4 alkylamino, and (C1-C4)(C1-C4) dialkylamino, with a nucleophile selected from a halide, a cyanide, and an amine, in the presence of a visible light source and a catalytically effective amount of an acridinium photocatalyst, and under anaerobic conditions, thereby forming the compound.

2. The method of claim 1, wherein Z contains a radioisotope.

3. The method of claim 1, wherein Z is selected from halogen and —CN.

4. The method of claim 1, wherein the electron donating group is —$OR^{20}$.

5. The method of claim 1, wherein the nucleophile is isotopically-labeled.

6. The method of claim 1, wherein the nucleophile is a halide.

7. The method of claim 1, wherein the acridinium photocatalyst has a structure represented by a formula:

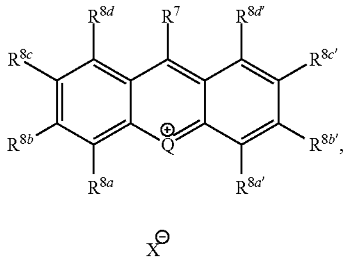

wherein Q is $NR^9$;

wherein $R^9$ is selected from C1-C4 alkyl, aryl, and heteroaryl, and is substituted with 0, 1, 2, or 3 groups independently selected from halogen, —$CF_3$, —$NH_2$, C1-C4 alkyl, C1-C4 alkoxy, C1-C4 alkylamino, (C1-C4)(C1-C4) dialkylamino;

wherein X is selected from $BF_4$, TfO, $PF_6$, and $ClO_4$;

wherein $R^7$ is selected from C1-C4 alkyl and phenyl substituted with 0, 1, 2, or 3 groups independently selected from halogen and C1-C4 alkyl; and wherein each of $R^{8a}$, $R^{8b}$, $R^{8c}$, $R^{8d}$, $R^{8a'}$, $R^{8b'}$, $R^{8c'}$, and $R^{8d'}$ is independently selected from hydrogen, halogen, —$CF_3$, —$NH_2$, C1-C4 alkyl, C1-C4 alkoxy, C1-C4 alkylamino, C1-C4 dialkylamino, and phenyl substituted with 0, 1, 2, or 3 groups independently selected from halogen, —$CF_3$, —$NH_2$, C1-C4 alkyl, C1-C4 alkoxy, C1-C4 alkylamino, and (C1-C4)(C1-C4) dialkylamino.

8. The method of claim 7, wherein the acridinium photocatalyst has a structure:

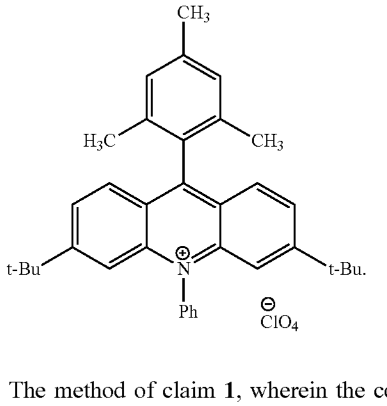

9. The method of claim 1, wherein the compound has a structure selected from:

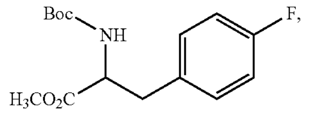

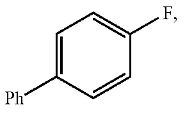

-continued
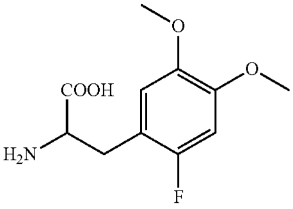, and 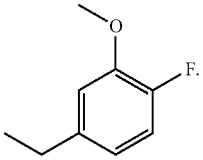
10. The method of claim 2, wherein the radioisotope is $^{18}F$.
11. The method of claim 1, wherein the compound has a structure selected from:
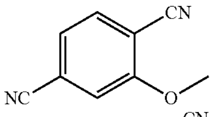, 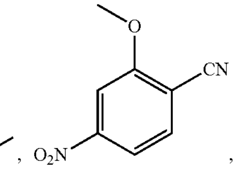,
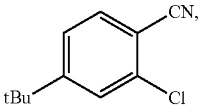
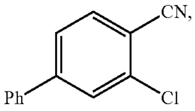
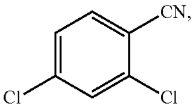
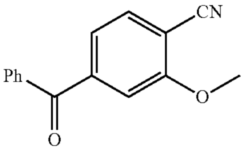,
-continued
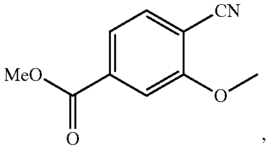, 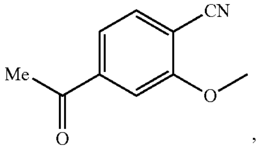,
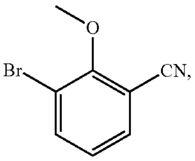
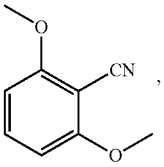,
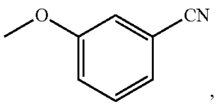, 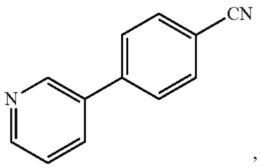, and
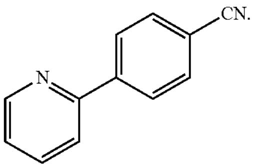
12. The method of claim 11, wherein the cyanide is $^{11}CN$.
* * * * *